(12) United States Patent
Schwarz et al.

(10) Patent No.: US 7,115,639 B2
(45) Date of Patent: Oct. 3, 2006

(54) PYRROLIDINE OXADIAZOLE- AND THIADIAZOLE OXIME DERIVATIVES BEING OXYTOCIN RECEPTOR ANTAGONISTS

(75) Inventors: Matthias Schwarz, Thonex (CH); Anna Quattropani, Geneva (CH); Patrick Page, Saint-Julien-en-Genevois (FR); Russell J. Thomas, Oxfordshire (GB); Vincent Pomel, Groisy (FR)

(73) Assignee: Applied Research Systems ARS Holding N.V., Curacao (AN)

( * ) Notice: Subject to any disclaimer, the term of this patent is extended or adjusted under 35 U.S.C. 154(b) by 49 days.

(21) Appl. No.: 10/480,992

(22) PCT Filed: Jun. 14, 2002

(86) PCT No.: PCT/EP02/06629

§ 371 (c)(1),
(2), (4) Date: May 19, 2004

(87) PCT Pub. No.: WO02/102799

PCT Pub. Date: Dec. 27, 2002

(65) Prior Publication Data

US 2004/0220238 A1    Nov. 4, 2004

(30) Foreign Application Priority Data

Jun. 18, 2001 (EP) .................................. 01113632

(51) Int. Cl.
```
A61K 31/433    (2006.01)
A61K 31/4245   (2006.01)
C07D 271/113   (2006.01)
C07D 285/125   (2006.01)
```

(52) U.S. Cl. ................. 514/364; 514/254.03; 514/343; 514/363; 544/367; 546/209; 548/125; 548/128; 548/131; 548/132; 548/144

(58) Field of Classification Search ................ None
See application file for complete search history.

(56) References Cited

U.S. PATENT DOCUMENTS 5,756,497 A      5/1998  Bell et al.
2004/0220238 A1  11/2004 Schwarz et al.

FOREIGN PATENT DOCUMENTS

| EP | 0 694 536  | 1/1996  |
|----|------------|---------|
| WO | 96/22775   | 8/1996  |
| WO | 98 25901   | 6/1998  |
| WO | 00 66119   | 11/2000 |
| WO | WO 0066119 A | * 11/2000 |
| WO | 01 72705   | 10/2001 |
| WO | 01 74769   | 10/2001 |
| WO | WO 200172705 A1 | * 10/2001 |

OTHER PUBLICATIONS

E.D. Nicolaides et al.: "Modified di- and tripeptides of the c-terminal portion of oxytocin and vasopressin as possible cognition activation agents" Journal of Medicinal Chemistry, vol. 29, No. 6, pp. 959-971, 1986.
D.F. Cunningham et al.: "Proline specific peptidases" Biochimica et Biophysica Acta. Protein Structure and Molecular Encymology, vol. 1343, No. 2, pp. 160-186, Dec. 5, 1997.
M. Maggi et al. J. Clin. Endocrinol. Metabol., vol. 70, pp. 1142-1154, 1990.
M. Maggi et al. J. Reprod. Fertil., vol. 101, No. 2, pp. 345-352, 1994.
T.M. Goodwin et al. Am. J. Obstet. Gynecol., vol. 170, No. 2, pp. 474-478, 1994.
Evans et al. J. Med. Chem., vol. 35, pp. 3919-3927, 1992.

* cited by examiner

Primary Examiner—Joseph K. McKane
Assistant Examiner—Nyeemah A. Grazier
(74) Attorney, Agent, or Firm—Oblon, Spivak, McClelland, Maier & Neustadt, P.C.

(57) ABSTRACT

The present invention is related to pyrrolidine oxadiazole and thiadiazole derivatives for use as pharmaceutically active compounds, as well as pharmaceutical formulations containing such pyrrolidine oxadiazole derivatives. Said pyrrolidine derivatives are useful in the treatment and/or prevention of preterm labor, premature birth and dysmenorrhea. In particular, the present invention is related to pyrrolidine derivatives displaying a substantial modulatory, notably an antagonist activity of the oxytocin receptor. More preferably, said compounds are useful in the treatment and/or prevention of disease states mediated by oxytocin, including preterm labor, premature birth and dysmenorrhea. The present invention is furthermore related to novel pyrrolidine derivatives as well as to methods of their preparation. (I) B is a oxadiazole or thiadiazole group

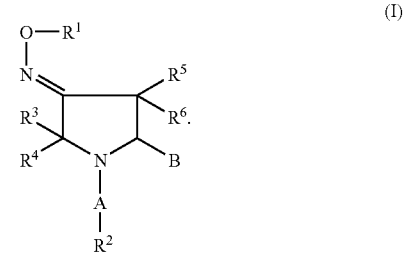

(I)

26 Claims, No Drawings

US 7,115,639 B2

PYRROLIDINE OXADIAZOLE- AND THIADIAZOLE OXIME DERIVATIVES BEING OXYTOCIN RECEPTOR ANTAGONISTS

This application is a 371 of PCT/EP02/06629, filed on Jun. 14, 2002. This application claims priority under 35 U.S.C. 119 (a–d) to foreign application EPO 01113632.2 filed on Jun. 18, 2001.

FIELD OF THE INVENTION

The present invention is related to new pyrrolidine oxadiazole and pyrrolidine thiadiazole derivatives, in particular for use as medicaments, as well as pharmaceutical formulations containing such pyrrolidine derivatives. Said pyrrolidine derivatives are useful in the treatment and/or prevention of preterm labor, premature birth and dysmenorrhea. Preferably, the pyrrolidine derivatives display a modulatory, notably an antagonist activity of the oxytocin receptor. More preferably, said compounds are useful in the treatment and/or prevention of disease states mediated by oxytocin, including preterm labor, premature birth and dysmenorrhea.

BACKGROUND OF THE INVENTION

In the field of obstetrics, one of the most important problems is the management of preterm labor and premature birth as they represent a major cause of perinatal morbidity and mortality.

For the treatment of preterm labor the use of magnesium sulfate and ethanol has been suggested. However, magnesium sulfate at plasma concentrations above the therapeutic range of 4 to 8 mg/dL can cause inhibition of cardiac conduction and neuromuscular transmission, respiratory depression and cardiac arrest, thus making this agent unsuitable notably when the renal function is impaired.

Ethanol is effective in preventing premature labor, but it does not produce a corresponding reduction in the incidence of fetal respiratory distress. Also, ethanol is assumed to have a negative impact on the fetus.

Two further therapeutic agents fall into either of the groups of:
a) β2-adrenergic agonists, or
b) oxytocin antagonists.

The β2-adrenergic receptor generally causes an inhibitory action within the cells wherein it is expressed (muscles, heart, uterus etc). β2-adrenergic agonists are used to activate said inhibitory action of the receptor. Hence, β2-adrenergic agonists are sympathomimetics which—among others—inhibit uterine contractility. Known β2-adrenergic agonists for the treatment of preterm labor are Ritodrine, Terbutaline and Albuterol.

Ritodrine (i.e. (R*,S*)-4-Hydroxy-.alpha.-[1-[[2-(4-hydroxyphenyl)ethyl]amino]ethyl]benzenemethanol; see U.S. Pat. No. 3,410,944 of N. V. Philips) is the leading $\beta_2$-adrenergic agonist but causes a number of cardiovascular and metabolic side effects in the mother, including tachycardia, increased renin secretion, hyperglycemia (and reactive hypoglycemia in the infant).

Terbutaline (i.e. 5-[2-[(1,1-Dimethylethyl)amino]-1-hydroxyethyl]-1,3-benzenediol, U.S. Pat. No. 3,937,838, Draco) and Albuterol ($\alpha^1$-[[(1,1-Dimethylethyl)amino]methyl]-4-hydroxy-1,3-benzenedimethanol; U.S. Pat. No. 3,644,353, Allen and Hanburys) are further $\beta_2$-adrenergic agonists and have side effects similar to those of Ritodrine.

A more recent approach of treating preterm labor consists in the use of oxytocin antagonists.

Oxytocin (OT) is a peptide hormone and causes the contraction of the uterus of mammals during labor. The corresponding oxytocin receptor is similar to $V_{1a}$ and $V_2$ vasopressin receptors and acts via a G protein-coupled receptor, coupled to activation of phospholipase C and increases in $IP_3$ that release $Ca^{2+}$ from intracellular stores. The increases in intracellular calcium that ensue lead to increased contraction of smooth muscle via activation of myosin light chain kinase. Oxytocin (OT) receptors increase dramatically during the course of pregnancy. The concentration of OT receptors has been shown to correlate with spontaneous uterine activity (M. Maggi et al. *J. Clin. Endocrinol Metabol;* 70; 1142, 1990). In the last few years, evidence has accumulated to strongly suggest that the hormone oxytocin may be a physiological initiator of labor in several mammalian species including humans. Furthermore, oxytocin is believed to exert this effect in two different parts:
  by directly contracting the uterine myometrium and
  by enhancing the synthesis and release of contractile prostaglandins from the uterine endometrium/decidua. These prostaglandins may, in addition, be important in the cervical ripening process.

By these mechanisms, the process of labor (term and preterm) is initiated by a heightened sensitivity of the uterus to oxytocin, resulting in part as a result of an increase in the number of oxytocin receptors in this tissue.

By blocking oxytocin, the direct (contractile) and indirect (enhanced prostaglandin synthesis) effects of oxytocin on the uterus may be achieved. An oxytocin blocker, or antagonist, is therefore assumed to be more efficacious for treating preterm labor than current regimens.

Atosiban (i.e. oxytocin, 1-(3-mercaptopropanoic acid)-2-(O-ethyl-D-tyrosine)-4-L-threonine-8-L-ornithine) is a cyclic pentapeptide which is the best known OT antagonist (WO 9501368, Ferring A B; *J. Reprod. Fertil.*, 101(2), 345–52 (English) 1994; *Am. J. Obstet. Gynecol.*, 170(2), 474–8 (English) 1994). The principal drawback to the use of peptide antagonists like atosiban is the problem of low oral bioavailability resulting from intestinal degradation. Hence, they must be administered parenterally.

Also, WO 96/22775 and U.S. Pat. No. 5,756,497 (Merck) disclose benzoxazinyl-piperidines or benzoxazinones as OT receptor antagonists. Indanylpiperidines and tolyl-piperazines are reported by Evans et al. in *J. Med. Chem.*, 35, 3919 (1992) as being orally deliverable OT antagonists It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. The compounds of the present invention are therefore useful in the treatment and prevention of preterm labor and premature birth. The compounds are also useful for stoppage of labor preparatory to cesarean delivery. In particular the compounds of the present invention are useful in the treatment and prevention of oxytocin-related disorders of animals, preferably mammals and especially humans. It is another purpose of this invention to provide a method of antagonizing the functions of oxytocin in disease states in mammals. It is also a purpose of this invention to develop a method of preventing or treating the oxytocin-related disorders of preterm labor by antagonizing the binding of oxytocin to its receptor.

The compounds of the present invention are also useful in the treatment of dysmenorrhea which may be defined as a cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, an oxytocin antagonist is more efficacious for treating dysmenorrhea than current regimens.

DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"$C_2$–$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$–$C_6$-alkenyl aryl" refers to $C_2$–$C_6$-alkenyl groups having an aryl substituent, including 2-phenylvinyl and the like.

"$C_2$–$C_6$-alkenyl heteroaryl" refers to $C_2$–$C_6$-alkenyl groups having a heteroaryl substituent, including 2-(3-pyridinyl)vinyl and the like.

"$C_2$–$C_6$-alkynyl" refers to alkynyl groups preferably having from 2 to 6 carbon atoms and having at least 1–2 sites of alkynyl unsaturation, preferred alkynyl groups include ethynyl (—C≡CH), propargyl (—$CH_2$C≡CH), and the like.

"$C_2$–$C_6$-alkynyl aryl" refers to $C_2$–$C_6$-alkynyl groups having an aryl substituent, including phenylethynyl and the like.

"$C_2$–$C_6$-alkynyl heteroaryl" refers to $C_2$–$C_6$-alkynyl groups having a heteroaryl substituent, including 2-thienylethynyl and the like.

"$C_3$–$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$–$C_6$-alkyl cycloalkyl" refers to $C_1$–$C_6$-alkyl groups having a cycloalkyl substituent, including cyclohexylmethyl, cyclopentylpropyl, and the like.

"heterocycloalkyl" refers to a C3–C8-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$–$C_6$-alkyl heterocycloalkyl" refers to $C_1$–$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$–$C_6$-alkyl carboxy" refers to $C_1$–$C_6$-alkyl groups having an carboxy substituent, including 2-carboxyethyl and the like.

"Acyl" refers to the group —C(O)R where R includes H, "$C_1$–$C_6$-alkyl", "$C_2$–$C_6$-alkenyl", "$C_2$–$C_6$-alkynyl", "$C_3$–$C_8$-cycloalkyl", heterocycloalkyl"heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl acyl" refers to $C_1$–$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$–$C_8$-(hetero)cycloalkyl acyl" refers to 3 to 8 memebered cycloalkyl or heterocycloalkyl groups having an acyl substituent.

"Acyloxy" refers to the group —OC(O)R where R includes H, "$C_1$–$C_6$-alkyl", "$C_2$–$C_6$-alkenyl", "$C_2$–$C_6$-alkynyl", "$C_3$–$C_8$-cycloalkyl", heterocycloalkyl"heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl acyloxy" refers to $C_1$–$C_6$-alkyl groups having an acyloxy substituent, including 2-(acetyloxy)ethyl and the like.

"Alkoxy" refers to the group —O—R where R includes "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl alkoxy" refers to $C_1$–$C_6$-alkyl groups having an alkoxy substituent, including 2-ethoxyethyl and the like.

"Alkoxycarbonyl" refers to the group —C(O)OR where R includes "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl alkoxycarbonyl" refers to $C_1$–$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl aminocarbonyl" refers to $C_1$–$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$–$C_6$-alkyl", "$C_2$–$C_6$-alkenyl", "$C_2$–$C_6$-alkynyl", "$C_3$–$C_8$-cycloalkyl", "heterocloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl acylamino" refers to $C_1$–$C_6$-alkyl groups having an acylamino substituent, including 2-(propionylamino)ethyl and the like.

"Ureido" refers to the group —NRC(O)NR'R" where each R, R', R" is independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl", and where R' and R", together with the nitrogen atom to which they are attached, can optionally form a 3–8-membered heterocycloalkyl ring.

"$C_1$–$C_6$-alkyl ureido" refers to $C_1$–$C_6$-alkyl groups having an ureido substituent, including 2-(N'-methylureido)ethyl and the like.

"Carbamate" refers to the group —NRC(O)OR' where each R, R' is independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"Amino" refers to the group —NRR' where each R, R' is independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl", and where R and R', together with the nitrogen atom to which they are attached, can optionally form a 3–8-membered heterocycloalkyl ring.

"$C_1$–$C_6$-alkyl amino" refers to $C_1$–$C_6$-alkyl groups having an amino substituent, including 2-(1-pyrrolidinyl)ethyl and the like.

"Ammonium" refers to a positively charged group —N$^+$RR'R", where each R, R', R" is independently, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl", and where R and R', together with the nitrogen atom to which they are attached, can optionally form a 3–8-membered heterocycloalkyl ring.

"$C_1$–$C_6$-alkyl ammonium" refers to $C_1$–$C_6$-alkyl groups having an ammonium substituent, including 2-(1-pyrrolidinyl)ethyl and the like.

"Ionisable moiety" refers to a moiety which may be transformed into a salt, e.g. by protonation Amino or sulfonyl moieties are examples for ionisable/protonable moities.

"Halogen" refers to fluoro, chloro, bromo and iodo atoms.

"Sulfonyloxy" refers to a group —OSO$_2$—R wherein R is selected from H, "$C_1$–$C_6$-alkyl", "$C_1$–$C_6$-alkyl" substituted with halogens, e.g., an —OSO$_2$—CF$_3$$^-$ group, "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl sulfonyloxy" refers to $C_1$–$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$–$C_6$-alkyl", "$C_1$–$C_6$-alkyl" substituted with halogens, e.g., an —SO$_2$—CF$_3$ group, "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl sulfonyl" refers to $C_1$–$C_6$-alkyl groups having a sulfonyl substituent, including 2-(methylsulfonyl)ethyl and the like.

"Sulfinyl" refers to a group "—S(O)—R" wherein R is selected from H, "$C_1$–$C_6$-alkyl", "$C_1$–$C_6$-alkyl" substituted with halogens, e.g., an —SO—CF$_3$ group, "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl sulfinyl" refers to $C_1$–$C_6$-alkyl groups having a sulfinyl substituent, including 2-(methylsulfinyl)ethyl and the like.

"Sulfanyl" refers to groups —S—R where R includes H, "$C_1$–$C_6$-alkyl", "$C_1$–$C_6$-alkyl" substituted with halogens, e.g., an —SO—CF$_3$ group, "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl". Preferred sulfanyl groups include methylsulfanyl, ethylsulfanyl, and the like.

"$C_1$–$C_6$-alkyl sulfanyl" refers to $C_1$–$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl sulfonylamino" refers to $C_1$–$C_6$-alkyl groups having a sulfonylamino substituent, including 2-(ethylsulfonylamino)ethyl and the like.

"Aminosulfonyl" refers to a group —$SO_2$—NRR' where each R, R' includes independently hydrogen, "$C_1$–$C_6$-alkyl", "$C_2$–$C_6$-alkenyl", "$C_2$–$C_6$-alkynyl", "$C_3$–$C_8$-cycloalkyl", "heterocycloalkyl", "aryl", "heteroaryl", "$C_1$–$C_6$-alkyl aryl" or "$C_1$–$C_6$-alkyl heteroaryl", "$C_2$–$C_6$-alkenyl aryl", "$C_2$–$C_6$-alkenyl heteroaryl", "$C_2$–$C_6$-alkynyl aryl", "$C_2$–$C_6$-alkynylheteroaryl", "$C_1$–$C_6$-alkyl cycloalkyl", "$C_1$–$C_6$-alkyl heterocycloalkyl".

"$C_1$–$C_6$-alkyl aminosulfonyl" refers to $C_1$–$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$–$C_6$-alkyl", "$C_2$–$C_6$-alkenyl", "$C_2$–$C_6$-alkynyl", "cycloalkyl", "heterocycloalkyl", "$C_1$–$C_6$-alkyl aryl", "$C_1$–$C_6$-alkyl heteroaryl", "$C_1$–$C_6$-alkyl cycloalkyl", "$C_1$–$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quarternary ammonium salt of the formula —NR,R',R"+Z−, wherein R, R', R" is independently hydrogen, alkyl, or benzyl, $C_1$–$C_6$-alkyl, $C_2$–$C_6$-alkenyl, $C_2$–$C_6$-alkynyl, $C_1$–$C_6$-alkyl aryl, $C_1$–$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have the inventive set out activity as OT-R antagonists.

General formula (I) of the present invention also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

One aspect of the present invention consists in the pyrrolidine oxadiazole and thiadiazole compounds of formula (I).

Pyrrolidine oxadiazole and thiadiazole derivatives according to formula I are suitable to modulate, in particular to inhibit the OT-R function and more specifically to antagonise the oxytocin receptor. When the oxytocin receptor is bound by the compounds according to formula I, oxytocin is antagonised by being blocked from its receptor and is therefore unable to exert its biologic or pharmacological effects. The compounds of the present invention are therefore in particular useful in the treatment and/or prevention of oxytocin-related disorders of mammals and in particular of humans.

The compounds according to the present invention are those of formula I.

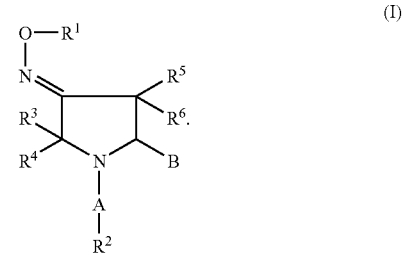

(I)

Said formula also comprises its geometrical isomers, its optically active forms as enantiomers, diastereomers and its racemate forms, as well as pharmaceutically acceptable salts thereof. Preferred pharmaceutically acceptable salts of the compound I are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate (mesylate), benzenesulfonate, and para-toluenesulfonate salts.

In said formula (I), A is selected from the group consisting of —(C=O)—, —(C=O)—O—, —$SO_2$—, —$SO_2$NH—, —C(=NH)—, —(C=O)—NH—, —(C=S)—NH, —$CH_2$—. Most preferred is A being a carbonyl group.

B is an unsubstituted or substituted oxadiazole or thiadiazole ring.

$R^1$ is selected from the group comprising or consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted $C_1$–$C_6$-alkyl aryl, unsubstituted or substituted $C_1$–$C_6$-alkyl heteroaryl, $R^1$ can form with the O atom to which it is attached a 3–8 membered substituted or unsubstituted, saturated or unsaturated heterocyclic ring which may contain 1–2 further heteroatoms selected from N, S and O and which is optionally fused with an aryl, heteroaryl or 3–8 membered saturated or unsaturated cycloalkyl ring. Preferably, $R^1$ is H or a $C_1$–$C_3$-alkyl, most preferred a methyl group.

$R^2$ is selected from the group comprising or consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl group. More a preferred is an aryl, in particular a phenyl group which is optionally substituted, e.g. by a further phenyl group (thus providing a biphenyl moiety).

$R^3$, $R^4$, $R^5$ and $R^6$ are independently selected from each other from the group consisting of hydrogen, halogen, $C_1$–$C_6$-alkyl, $C_1$–$C_6$-alkoxy. Preferably each of them is H.

Preferred pyrrolidine derivatives are those compounds according to formula I wherein $R^1$ is selected from the group consisting of H or —$C_1$–$C_6$ alkyl, in particular —$CH_3$, A is —(C=O)—, $R^2$ is a substituted or unsubstituted aryl, a substituted or unsubstituted heteroaryl group, particularly a biphenyl group.

According to a preferred embodiment, the substituent B is a 1,2,4 oxadiazole substituent which may be attached to the pyrrolidine ring according to the following modes (IIa) or (IIb):

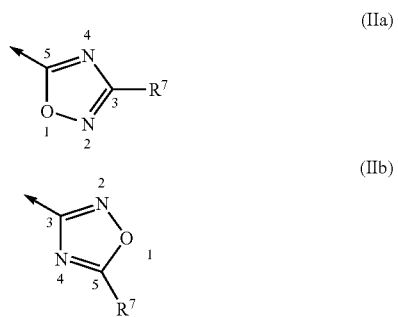

(IIa)

(IIb)

In said formulae (IIa) and (IIb), $R_7$ is selected from the group comprising or consisting of hydrogen, sulfonyl, amino, unsubstituted or substituted $C_1$–$C_6$-alkyl, unsubstituted or substituted $C_2$–$C_6$-alkenyl, unsubstituted or substituted $C_2$–$C_6$-alkynyl, wherein said alkyl, alkenyl, alkynyl chains may be interrupted by a heteroatom selected from N, O or S, unsubstituted or substituted aryl, unsubstituted or substituted heteroaryl, unsubstituted or substituted saturated or unsaturated 3–8-membered cycloalkyl, unsubstituted or substituted heterocycloalkyl, wherein said cycloalkyl, heterocycloalkyl, aryl or heteroaryl groups may be fused with 1–2 further cycloalkyl, heterocycloalkyl, aryl or heteroaryl group, an acyl moiety, unsubstituted or substituted $C_1$–$C_6$-alkyl aryl, unsubstituted or substituted $C_1$–$C_6$-alkyl heteroaryl, unsubstituted or substituted $C_1$–$C_6$-alkenyl aryl, unsubstituted or substituted $C_1$–$C_6$-alkenyl heteroaryl, unsubstituted or substituted $C_1$–$C_6$-alkynyl aryl, unsubstituted or substituted $C_1$–$C_6$-alkynyl heteroaryl, unsubstituted or substituted $C_1$–$C_6$-alkyl cycloalkyl, unsubstituted or substituted $C_1$–$C_6$-alkyl heterocycloalkyl, unsubstituted or substituted $C_1$–$C_6$-alkenyl cycloalkyl, unsubstituted or substituted $C_1$–$C_6$-alkenyl heterocycloalkyl, unsubstituted or substituted $C_1$–$C_6$-alkynyl cycloalkyl, unsubstituted or substituted $C_1$–$C_6$-alkynyl heterocycloalkyl, substituted or unsubstituted alkoxycarbonyl, substituted or unsubstituted aminocarbonyl, substituted or unsubstituted $C_1$–$C_6$-alkyl carboxy, substituted or unsubstituted $C_1$–$C_6$-alkyl acyl, substituted or unsubstituted aryl acyl, substituted or unsubstituted heteroaryl acyl, substituted or unsubstituted $C_3$–$C_8$-(hetero)cycloalkyl acyl, unsubstituted or substituted $C_1$–$C_6$-alkyl acyloxy, unsubstituted or substituted $C_1$–$C_6$-alkyl alkoxy, unsubstituted or substituted $C_1$–$C_6$-alkyl alkoxycarbonyl, unsubstituted or substituted $C_1$–$C_6$-alkyl aminocarbonyl, unsubstituted or substituted $C_1$–$C_6$-alkyl acylamino, acylamino, unsubstituted or substituted $C_1$–$C_6$-alkyl ureido, substituted or unsubstituted $C_1$–$C_6$-alkyl carbamate, unsubstituted or substituted $C_1$–$C_6$-alkyl amino, unsubstituted or substituted $C_1$–$C_6$-alkyl ammonium, unsubstituted or substituted $C_1$–$C_6$-alkyl sulfonyloxy, unsubstituted or substituted $C_1$–$C_6$-alkyl sulfonyl, unsubstituted or substituted $C_1$–$C_6$-alkyl sulfinyl, unsubstituted or substituted $C_1$–$C_6$-alkyl sulfanyl, unsubstituted or substituted $C_1$–$C_6$-alkyl sulfonylamino, unsubstituted or substituted $C_1$–$C_6$-alkyl aminosulfonyl, hydroxy, halogen, cyano.

According to a preferred embodiment, $R^7$ is a substituent comprising an ionisable (notably a protonable) moiety.

Specifically, $R^7$ may be selected from the group consisting of a carboxy or an amino moiety.

Alternatively, $R^7$ may be selected from the group consisting of from any of the above mentioned substituents which carries at least one carboxy or an amino moiety. A preferred ionisable (protonable) moiety is a cyclic tertiary amine (being a hetereocycloalkyl).

More preferred are $C_1$–$C_6$-alkyl amino, heterocycloalkyl like piperazines or piperidines, $C_1$–$C_6$-alkyl heterocycloalkyl, aminocarbonyl, $C_1$–$C_6$-alkyl aminocarbonyl, $C_1$–$C_6$-alkyl acylamino, $C_1$–$C_6$-alkyl sulfonyl, $C_1$–$C_6$-alkyl carboxy. Most preferred are dimethylaminomethyl, 2-(dimethylamino)ethyl, 1-methyl-3-piperidinyl, (4-acetyl-1-piperazinyl)methyl.

According to another embodiment, the substituent B is a 1,3,4-oxadiazole of formula (IV) or its tautomer of formula (III):

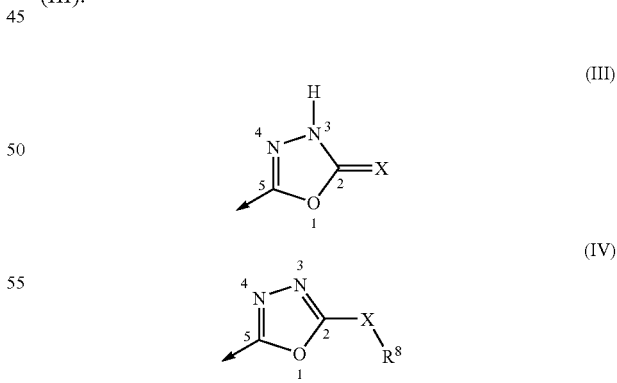

(III)

(IV)

X in said formulae (III) and (IV) is O or S, whereby in case the case of formula IV, X may also be a bond. In the case where X is O or S, and $R_8$ is hydrogen, compounds of formula IV represent the corresponding tautomers of formula III.

$R_8$ of formula (IV) is selected from the group comprising or consisting of hydrogen unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, optionally containing at least one heteroatom (e.g. 1 to 3) selected from N, O, S, an acyl moiety, unsubstituted or substituted $C_1$–$C_6$-alkyl aryl, unsubstituted or substituted $C_1$–$C_6$-alkyl heteroaryl, unsubstituted or substituted $C_1$–$C_6$-alkenyl aryl, unsubstituted or substituted $C_1$–$C_6$-alkenyl heteroaryl, substituted or unsubstituted alkoxycarbonyl, carboxylic amide, substituted or unsubstituted $C_1$–$C_6$-alkoxy, substituted or unsubstituted aryloxy, substituted or unsubstituted heteroaryloxy, halogen, cyano, substituted or unsubstituted $C_1$–$C_6$-alkyl carbonyl, substituted or unsubstituted arylcarbonyl or heteroarylcarbonyl, substituted or unsubstituted saturated or unsaturated $C_4$–$C_8$-cycloalkylcarbonyl, wherein said cycloalkyl or aryl or heteroaryl groups may be fused with 1–2 further cycloalkyl or aryl or heteroaryl group and wherein said alkyl, alkenyl, alkynyl chain may be interrupted by an heteroatom selected from N, O or S Particularly more preferred pyrrolidine derivatives are those compounds according to formula I wherein A is —(C=O), $R^1$ is a $C_1$–$C_6$ alkyl group, $R^2$ is either a aryl group or a heteroaryl, each of $R^3$, $R^4$, $R^5$ and $R^6$ is H and B is an oxadiazole according to formulae IIa, IIb, III or IV.

Most preferred pyrrolidine derivatives are those compounds according to formula I, wherein A is —(C=O), $R^1$ is a methyl group, $R^2$ is either an (un)substituted aryl group or an (un)substituted heteroaryl, each of $R^3$, $R^4$, $R^5$ and $R^6$ is H and B is an oxadiazole according to formulae IIa, IIb, III and IV, particularly a 1,2,4 oxadiazole of formulae IIa or IIb.

Most preferred pyrrolidine derivatives are those compounds according to formula I wherein A is —(C=O), $R^1$ is a methyl group, $R^2$ is a biphenyl group, each of $R^3$, $R^4$, $R^5$ and $R^6$ is H and B is an oxadiazole according to formulae IIa, IIb, III and IV, particularly a 1,2,4 oxadiazole of formula IIa or IIb.

The compounds of formula I may contain one or more asymmetric centers and may therefore exist as enantiomers or diasteroisomers. It is to be understood that the invention includes both mixtures and separate individual isomers or enantiomers of the compounds of formula I. In a particularly preferred embodiment the pyrrolidine derivatives according to formula I are obtained in an enantiomeric excess of at least 52% ee, preferably of at least 92–98% ee.

Specific examples of compounds of formula I include the following:

(3EZ,5S)-1-([1,1'-biphenyl]-4-ylcarbonyl)-5-(3-methyl-1,2,4-oxadiazol-5-yl)-3-pyrrolidinone O-methyloxime (3EZ,5S)-1-[(2'-methyl[1,1'-biphenyl]-4-yl)carbonyl]-5-(3-methyl-1,2,4-oxadiazol-5-yl)-3-pyrrolidinone O-methyloxime (3EZ,5S)-1-([1,1'-biphenyl]-4-ylcarbonyl)-5-(1,3,4-oxadiazol-2-yl)-3-pyrrolidinone O-methyloxime (3EZ,5S)-1-([1,1'-biphenyl]-4-ylcarbonyl)-5-(5-oxo-1,2,4-oxadiazol-5-yl)-3-pyrrolidinone O-methyloxime (3EZ,5S)-1-([1,1'-biphenyl]-4-ylcarbonyl)-5-(5-thioxo-4,5-dihydro-1,3,4-oxadiazol-2-yl)-3-pyrrolidinone O-methyloxime (3EZ,5S)-5-(3-benzyl-1,2,4-oxadiazol-5-yl)-1-([1,1'-biphenyl]-4-ylcarbonyl)-3-pyrrolidinone O-methyloxime (3EZ,5S)-1-([1,1'-biphenyl]-4-ylcarbonyl)-5-(3-{[(2-furylmethyl)sulfanyl]methyl}-1,2,4-oxadiazol-5-yl)-3-pyrrolidinone O-methyloxime (3EZ,5S)-1-([1,1'-biphenyl]-4-ylcarbonyl)-5-{3-[2-oxo-2-(1-pyrrolidinyl)ethyl]-1,2,4-oxadiazol-5-yl}-3-pyrrolidinone O-methyloxime (3EZ,5S)-1-([1,1'-biphenyl]-4-ylcarbonyl)-5-{3-[(2-pyridinylsulfanyl)methyl]-1,2,4-oxadiazol-5-yl}-3-pyrrolidinone O-methyloxime (3EZ,5S)-1-([1,1'-biphenyl]-4-ylcarbonyl)-5-[3-(4-fluorophenyl)-1,2,4-oxadiazol-5-yl]-3-pyrrolidinone O-methyloxime (3EZ,5S)-1-([1,1'-biphenyl]-4-ylcarbonyl)-5-{3-[(2-thienylsulfanyl)methyl]-1,2,4-oxadiazol-5-yl}-3-pyrrolidinone O-methyloxime (3EZ,5S)-1-([1,1'-biphenyl]-4-ylcarbonyl)-5-{3-[2-(3,5-dimethyl-1H-pyrazol-1-yl)ethyl]-1,2,4-oxadiazol-5-yl}-3-pyrrolidinone O-methyloxime (3EZ,5S)-1-([1,1'-biphenyl]-4-ylcarbonyl)-5-{3-[(methylsulfonyl)methyl]-1,2,4-oxadiazol-5-yl}-3-pyrrolidinone O-methyloxime (3EZ,5S)-1-([1,1'-biphenyl]-4-ylcarbonyl)-5-[3-(5-methyl-3-isoxazolyl)-1,2,4-oxadiazol-5-yl]-3-pyrrolidinone O-methyloxime (3EZ,5S)-1-([1,1'-biphenyl]-4-ylcarbonyl)-5-[3-(2-thienylmethyl)-1,2,4-oxadiazol-5-yl]-3-pyrrolidinone O-methyloxime (3EZ,5S)-1-([1,1'-biphenyl]-4-ylcarbonyl)-5-(3-phenyl-1,2,4-oxadiazol-5-yl)-3-pyrrolidinone O-methyloxime (3EZ,5S)-1-([1,1'-biphenyl]-4-ylcarbonyl)-5-(3-{[(2-furylmethyl)sulfonyl]methyl}-1,2,4-oxadiazol-5-yl)-3-pyrrolidinone O-methyloxime (3EZ,5S)-5-[3-(aminomethyl)-1,2,4-oxadiazol-5-yl]-1-([1,1'-biphenyl]-4-ylcarbonyl)-3-pyrrolidinone O-methyloxime (3EZ,5S)-1-([1,1'-biphenyl]-4-ylcarbonyl)-5-{3-[(RS)-hydroxy(phenyl)methyl]-1,2,4-oxadiazol-5-yl}-3-pyrrolidinone O-methyloxime (3EZ,5S)-1-([1,1'-biphenyl]-4-ylcarbonyl)-5-{3-[(1RS)-1-hydroxypropyl]-1,2,4-oxadiazol-5-yl}-3-pyrrolidinone O-methyloxime (3EZ,5S)-1-([1,1'-biphenyl]-4-ylcarbonyl)-5-[3-hydroxymethyl)-1,2,4-oxadiazol-5-yl]-3-pyrrolidinone O-methyloxime (3EZ,5S)-1-([1,1'-biphenyl]-4-ylcarbonyl)-5-{3-[(1S,2R)-2-hydroxycyclohexyl]-1,2,4-oxadiazol-5-yl}-3-pyrrolidinone O-methyloxime (3EZ,5S)-1-([1,1'-biphenyl]-4-ylcarbonyl)-5-[3-(2-hydroxyethyl)-1,2,4-oxadiazol-5-yl]-3-pyrrolidinone O-methyloxime (3Z,5RS)-1-([1,1'-biphenyl]-4-ylcarbonyl)-5-[3-(2-hydroxyethyl)-1,2,4-oxadiazol-5-yl]-3-pyrrolidinone O-methyloxime (3EZ,5S)-1-([1,1'-biphenyl]-4-ylcarbonyl)-5-[3-(4-piperidinyl)-1,2,4-oxadiazol-5-yl]-3-pyrrolidinone O-methyloxime (3EZ,5S)-1-([1,1'-biphenyl]-4-ylcarbonyl)-5-{3-[(3RS)-piperidinyl]-1,2,4-oxadiazol-5-yl}-3-pyrrolidinone O-methyloxime (3EZ,5S)-1-([1,1'-biphenyl]-4-ylcarbonyl)-5-{3-[(2RS)-piperidinyl]-1,2,4-oxadiazol-5-yl}-3-pyrrolidinone O-methyloxime (3EZ,5S)-1-[(2'-chloro[1,1'-biphenyl]-4-yl)carbonyl]-5-(3-methyl-1,2,4-oxadiazol-5-yl)-3-pyrrolidinone O-methyloxime (3EZ,5S)-5-(3-methyl-1,2,4-oxadiazol-5-yl)-1-{[2'-(trifluoromethyl)[1,1'-biphenyl]-4-yl]carbonyl}-3-pyrrolidinone O-methyloxime (3Z,5S)-1-[(2'-fluoro[1,1'-biphenyl]-4-yl)carbonyl]-5-(3-methyl-1,2,4-oxadiazol-5-yl)-3-pyrrolidinone O-methyloxime
(3EZ,5S)-1-[(4'-fluoro[1,1'-biphenyl]-4-yl)carbonyl]-5-(3-methyl-1,2,4-oxadiazol-5-yl)-3-pyrrolidinone O-methyloxime
(3EZ,5S)-1-([1,1'-biphenyl]-4-ylcarbonyl)-5-(1,2,4-oxadiazol-3-yl)-3-pyrrolidinone O-methyloxime
(3E,5S)-1-[(2'-fluoro[1,1'-biphenyl]-4-yl)carbonyl]-5-(3-methyl-1,2,4-oxadiazol-5-yl)-3-pyrrolidinone O-methyloxime
(3E,5S)-1-[(2'-methyl[1,1'-biphenyl]-4-yl)carbonyl]-5-(3-methyl-1,2,4-oxadiazol-5-yl)-3-pyrrolidinone O-methyloxime
(3Z,5S)-1-[(2'-methyl[1,1'-biphenyl]-4-yl)carbonyl]-5-(3-methyl-1,2,4-oxadiazol-5-yl)-3-pyrrolidinone O-methyloxime
(3EZ,5S)-1-([1,1'-biphenyl]-4-ylcarbonyl)-5-[5-(phenoxymethyl)-1,2,4-oxadiazol-3-yl]-3-pyrrolidinone O-methyloxime
(3EZ,5S)-1-([1,1'-biphenyl]-4-ylcarbonyl)-5-(5-phenyl-1,2,4-oxadiazol-3-yl)-3-pyrrolidinone O-methyloxime
N-({3-[(2S,4EZ)-1-([1,1'-biphenyl]-4-ylcarbonyl)-4-(methoxyimino)pyrrolidinyl]-1,2,4-oxadiazol-5-yl}methyl)acetamide
(3EZ,5S)-1-([1,1'-biphenyl]-4-ylcarbonyl)-5-{5-[4-(hydroxymethyl)phenyl]-1,2,4-oxadiazol-3-yl}-3-pyrrolidinone O-methyloxime
(3EZ,5S)-1-([1,1'-biphenyl]-4-ylcarbonyl)-5-[5-(2-hydroxyethyl)-1,2,4-oxadiazol-3-yl]-3-pyrrolidinone O-methyloxime
(3EZ,5S)-1-([1,1'-biphenyl]-4-ylcarbonyl)-5-{5-[(2S)-2-hydroxy-2-phenylethyl]-1,2,4-oxadiazol-3-yl}-3-pyrrolidinone O-methyloxime
{3-[(2S,4EZ)-1-([1,1'-biphenyl]-4-ylcarbonyl)-4-(methoxyimino)pyrrolidinyl]-1,2,4-oxadiazol-5-yl}methylformamide
(3EZ,5S)-1-([1,1'-biphenyl]-4-ylcarbonyl)-5-[5-(methoxymethyl)-1,2,4-oxadiazol-3-yl]-3-pyrrolidinone O-methyloxime
(3EZ,5S)-1-([1,1'-biphenyl]-4-ylcarbonyl)-5-[5-(2-phenoxyethyl)-1,2,4-oxadiazol-3-yl]-3-pyrrolidinone O-methyloxime
(3EZ,5S)-1-([1,1'-biphenyl]-4-ylcarbonyl)-5-[5-(2-methoxyethyl)-1,2,4-oxadiazol-3-yl]-3-pyrrolidinone O-methyloxime
(3EZ,5S)-5-[5-(1-acetyl-4-piperidinyl)-1,2,4-oxadiazol-3-yl]-1-([1,1'-biphenyl]-4-ylcarbonyl)-3-pyrrolidinone O-methyloxime
(3EZ,5S)-1-([1,1'-biphenyl]-4-ylcarbonyl)-5-[5-(2-pyridinyl)-1,2,4-oxadiazol-3-yl]-3-pyrrolidinone O-methyloxime
(3EZ,5S)-1-([1,1'-biphenyl]-4-ylcarbonyl)-5-[5-(3-thienyl)-1,2,4-oxadiazol-3-yl]-3-pyrrolidinone O-methyloxime
(3EZ,5S)-1-([1,1'-biphenyl]-4-ylcarbonyl)-5-(5-ethyl-1,2,4-oxadiazol-3-yl)-3-pyrrolidinone O-methyloxime
(3EZ,5S)-1-([1,1'-biphenyl]-4-ylcarbonyl)-5-(5-cyclopentyl-1,2,4-oxadiazol-3-yl)-3-pyrrolidinone O-methyloxime
(3EZ,5S)-1-([1,1'-biphenyl]-4-ylcarbonyl)-5-(5-methyl-1,2,4-oxadiazol-3-yl)-3-pyrrolidinone O-methyloxime
(3EZ,5S)-1-([1,1'-biphenyl]-4-ylcarbonyl)-5-{5-[(RS)-hydroxy(phenyl)methyl]-1,2,4-oxadiazol-3-yl}-3-pyrrolidinone O-methyloxime
(3EZ,5S)-1-([1,1'-biphenyl]-4-ylcarbonyl)-5-{5-[(1RS)-1-hydroxy-2-phenylethyl]-1,2,4-oxadiazol-3-yl}-3-pyrrolidinone O-methyloxime
(3EZ,5S)-1-([1,1'-biphenyl]-4-ylcarbonyl)-5-{5-[(1R)-1-(dimethylamino)-2-phenylethyl]-1,2,4-oxadiazol-3-yl}-3-pyrrolidinone O-methyloxime.
(3EZ,5S)-1-([1,1'-biphenyl]-4-ylcarbonyl)-5-[5-(3-pyridinyl)-1,2,4-oxadiazol-3-yl]-3-pyrrolidinone O-methyloxime
(3EZ,5S)-1-([1,1'-biphenyl]-4-ylcarbonyl)-5-[5-(4-pyridinyl)-1,2,4-oxadiazol-3-yl]-3-pyrrolidinone O-methyloxime
(3Z,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime
(3EZ,5S)-5-[3-(1-acetyl-4-piperidinyl)-1,2,4-oxadiazol-5-yl]-1-([1,1'-biphenyl]-4-ylcarbonyl)-3-pyrrolidinone O-methyloxime
(3EZ,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime
N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(1-piperidinyl)propanamide
(3EZ,5S)-1-([1,1'-biphenyl]-4-ylcarbonyl)-5-{5-[(3)-1-methylpiperidinyl]-1,2,4-oxadiazol-3-yl}-3-pyrrolidinone O-methyloxime
(3EZ,5S)-1-([1,1'-biphenyl]-4-ylcarbonyl)-5-{5-[(3R)-1-methylpiperidinyl]-1,2,4-oxadiazol-3-yl}-3-pyrrolidinone O-methyloxime
(3EZ,5S)-1-([1,1'-biphenyl]-4-ylcarbonyl)-5-[5-(6-hydroxy-3-pyridinyl)-1,2,4-oxadiazol-3-yl]-3-pyrrolidinone O-methyloxime
(3Z,5S)-1-([1,1'-biphenyl]-4-ylcarbonyl)-5-{5-[(dimethylamino)methyl]-1,2,4-oxadiazol-3-yl}-3-pyrrolidinone O-methyloxime
(3EZ,5S)-5-{5-[(1S,2R)-1-amino-2-hydroxypropyl]-1,2,4-oxadiazol-3-yl}-1-([1,1'-biphenyl]-4-ylcarbonyl)-3-pyrrolidinone O-methyloxime
(3EZ,5S)-1-([1,1'-biphenyl]-4-ylcarbonyl)-5-{5-[(3S)-piperidinyl]-1,2,4-oxadiazol-3-yl}-3-pyrrolidinone O-methyloxime
(3EZ,5S)-1-([1,1'-biphenyl]-4-ylcarbonyl)-5-{5-[(3R)-piperidinyl]-1,2,4-oxadiazol-3-yl}-3-pyrrolidinone O-methyloxime
(3EZ,5RS)-1-([1,1'-biphenyl]-4-ylcarbonyl)-5-[5-(1-methyl-3-piperidinyl)-1,2,4-oxadiazol-3-yl]-3-pyrrolidinone O-methyloxime
tert-butyl (3R)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate
4-({3-[(2S,4EZ)-1-([1,1'-biphenyl]-4-ylcarbonyl)-4-(methoxyimino)pyrrolidinyl]-1,2,4-oxadiazol-5-yl}methyl)-2,6-piperazinedione
(3Z,5S)-1-([1,1'-biphenyl]-4-ylcarbonyl)-5-[3-(2-hydroxyethyl)-1,2,4-oxadiazol-5-yl]-3-pyrrolidinone O-methyloxime
(3Z,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime
(3EZ,5S)-1-([1,1'-biphenyl]-4-ylcarbonyl)-5-[5-(1-methyl-4-piperidinyl)-1,2,4-oxadiazol-3-yl]-3-pyrrolidinone O-methyloxime
(3EZ,5S)-1-([1,1'-biphenyl]-4-ylcarbonyl)-5-{5-[(dimethylamino)methyl]-1,2,4-oxadiazol-3-yl}-3-pyrrolidinone O-methyloxime
(3EZ,5S)-1-([1,1'-biphenyl]-4-ylcarbonyl)-5-[3-(1-methyl-4-piperidinyl)-1,2,4-oxadiazol-5-yl]-3-pyrrolidinone O-methyloxime (3EZ,5S)-5-{5-[(1S)-1-amino-2-hydroxyethyl]-1,2,4-oxadiazol-3-yl}-1-([1,1'-biphenyl]-4-ylcarbonyl)-3-pyrrolidinone O-methyloxime 5-[(2S,4EZ)-1-([1,1'-biphenyl]-4-ylcarbonyl)-4-(methoxyimino)pyrrolidinyl]-N-[3-(dimethylamino)propyl]-1,2,4-oxadiazole-3-carboxamide (3E,5S)-1-([1,1'-biphenyl]-4-ylcarbonyl)-5-{5-[(dimethylamino)methyl]-1,2,4-oxadiazol-3-yl}-3-pyrrolidinone O-methyloxime tert-butyl (3S)-3-{3-[(2S,4EZ)-1-([1,1'-biphenyl]-4-ylcarbonyl)-4-(methoxyimino)pyrrolidinyl]-1,2,4-oxadiazol-5-yl)}-1-piperidinecarboxylate (3EZ,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime (3Z,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime ethyl 5-[(2S,4EZ)-1-([1,1'-biphenyl]-4-ylcarbonyl)-4-(methoxyimino)pyrrolidinyl]-1,2,4-oxadiazole-3-carboxylate (3E,5S)-1-([1,1'-biphenyl]-4-ylcarbonyl)-5-[3-(2-hydroxyethyl)-1,2,4-oxadiazol-5-yl]-3-pyrrolidinone O-methyloxime N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(dimethylamino)propanamide tert-butyl 4-(2-{3-[(2S,4EZ)-1-([1,1'-biphenyl]-4-ylcarbonyl)-4-(methoxyimino)pyrrolidinyl]-1,2,4-oxadiazol-5-yl}ethyl)-1-piperazinecarboxylate (3EZ,5S)-1-[(2'-chloro-4'-fluoro[1,1'-biphenyl]-4-yl)carbonyl]-5-[3-(2-hydroxyethyl)-1,2,4-oxadiazol-5-yl]-3-pyrrolidinone O-methyloxime (3EZ,5S)-1-[(4'-fluoro-2'-methyl[1,1'-biphenyl]-4-yl)carbonyl]-5-(3-methyl-1,2,4-oxadiazol-5-yl)-3-pyrrolidinone O-methyloxime (3EZ,5S)-1-([1,1'-biphenyl]-4-ylcarbonyl)-5-{5-[2-(dimethylamino)ethyl]-1,2,4-oxadiazol-3-yl}-3-pyrrolidinone O-methyloxime 2-{5-[(2S,4EZ)-1-([1,1'-biphenyl]-4-ylcarbonyl)-4-(methoxyimino)pyrrolidinyl]-1,2,4-oxadiazol-3-yl}ethyl[(tert-butoxycarbonyl)amino]acetate N-({3-[(2S,4EZ)-1-([1,1'-biphenyl]-4-ylcarbonyl)-4-(methoxyimino)pyrrolidinyl]-1,2,4-oxadiazol-5-yl}methyl)-2-(dimethylamino)acetamide (3EZ,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime (3EZ,5S)-5-{5-[(1S)-1-amino-2-tert-butoxyethyl]-1,2,4-oxadiazol-3-yl}-1-([1,1'-biphenyl]-4-ylcarbonyl)-3-pyrrolidinone O-methyloxime tert-butyl 4-{5-[(2S,4EZ)-1-([1,1'-biphenyl]-4-ylcarbonyl)-4-(methoxyimino)pyrrolidinyl]-1,2,4-oxadiazol-3-yl)}-1-piperidinecarboxylate (3EZ,5S)-1-([1,1'-biphenyl]-4-ylcarbonyl)-5-[5-(1-piperazinylmethyl)-1,2,4-oxadiazol-3-yl]-3-pyrrolidinone O-methyloxime tert-butyl(4S)-4-{3-[(2S,4EZ)-1-([1,1'-biphenyl]-4-ylcarbonyl)-4-(methoxyimino)pyrrolidinyl]-1,2,4-oxadiazol-5-yl}-4-[(tert-butoxycarbonyl)amino]butanoate 4-{[(2S,4EZ)-2-(5-{([(tert-butoxycarbonyl)amino]methyl}-1,2,4-oxadiazol-3-yl)-4-(methoxyimino)pyrrolidinyl]carbonyl}-1,1'-biphenyl tert-butyl 2-{3-[(2S,4EZ)-1-([1,1'-biphenyl]-4-ylcarbonyl)-4-(methoxyimino)pyrrolidinyl]-1,2,4-oxadiazol-5-yl}ethylcarbamate 2-{5-[(2S,4EZ)-1-([1,1'-biphenyl]-4-ylcarbonyl)-4-(methoxyimino)pyrrolidinyl]-1,2,4-oxadiazol-3-yl}ethyl aminoacetate (3E,5S)-1-[(2',4'-difluoro[1,1'-biphenyl]-4-yl)carbonyl]-5-(3-methyl-1,2,4-oxadiazol-5-yl)-3-pyrrolidinone O-methyloxime (3EZ,5S)-1-[(2',4'-difluoro[1,1'-biphenyl]-4-yl)carbonyl]-5-(3-methyl-1,2,4-oxadiazol-5-yl)-3-pyrrolidinone O-methyloxime 4-{[(2S,4EZ)-2-(5-{(1S)-2-tert-butoxy-1-[(tert-butoxycarbonyl)amino]ethyl}-1,2,4-oxadiazol-3-yl)-4-(methoxyimino)pyrrolidinyl]carbonyl}-1,1'-biphenyl (3EZ,5S)-1-([1,1'-biphenyl]-4-ylcarbonyl)-5-(5-vinyl-1,2,4-oxadiazol-3-yl)-3-pyrrolidinone O-methyloxime 4-{[(2S,4EZ)-2-(5-{(1S,2R)-2-tert-butoxy-1-[(tert-butoxycarbonyl)amino]propyl}-1,2,4-oxadiazol-3-yl)-4-(methoxyimino)pyrrolidinyl]carbonyl}-1,1'-biphenyl (3Z,5S)-1-[(2',4'-difluoro[1,1'-biphenyl]-4-yl)carbonyl]-5-(3-methyl-1,2,4-oxadiazol-5-yl)-3-pyrrolidinone O-methyloxime tert-butyl 4-({3-[(2S,4EZ)-1-([1,1'-biphenyl]-4-ylcarbonyl)-4-(methoxyimino)pyrrolidinyl]-1,2,4-oxadiazol-5-yl}methyl)-1-piperazinecarboxylate A further aspect of the present invention is related to the use of the pyrrolidine oxadiazole or thiadiazole derivatives according to formula I as a medicament in particular for the treatment and/or prevention of preterm labor, premature birth, for stopping labor prior to cesarean delivery and dysmenorrhea. Preferably, the compounds according to formula I are suitable for the modulation of the OT function, thus specifically allowing the treatment and/or prevention of disorders which are mediated by the oxytocin receptor. Said treatment involves the modulation—notably the down regulation or the antagonisation—of the oxytocin receptor.

More specifically, the compounds of the present invention are useful for the treatment of preterm labor, dysmenorrhea and for stopping labor prior to cesarean delivery.

Still a further object of the present invention is a process for preparing the pyrrolidine derivatives according to formula I.

The pyrrolidine derivatives exemplified in this invention can be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Generally, the pyrrolidine derivatives according to the general formula I could be obtained by several processes, using both solution-phase and solid-phase chemistry protocols.

According to one process, pyrrolidine derivatives according to the general formula I, whereby the substituent B is a 1,2,4 oxadiazole of formula (IIa), are prepared from the corresponding carboxylic acid compounds V and amidoximes VI, whereby the substituents $R^1$–$R^7$, and A, are as above defined, by well known solution-phase chemistry protocols, such as those described in the Examples and shown in Scheme 1, below.

Scheme 1

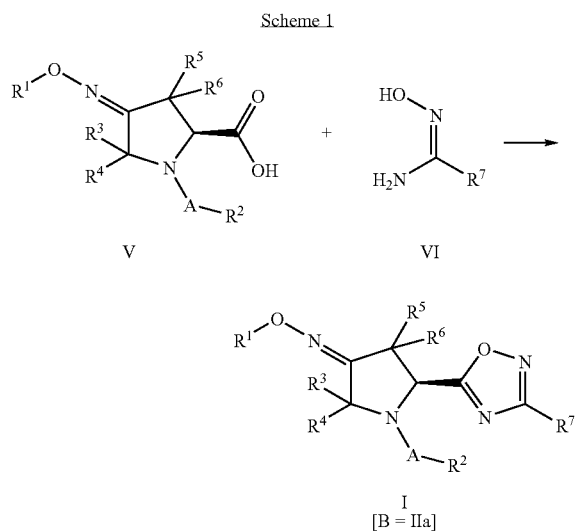

The amidoxime components VI are either obtained from commercial sources or made from the corresponding nitrites VII, by treatment of the latter with hydroxylamine under standard conditions well known to the person skilled in the art, such as those described in the Examples and shown in Scheme 2 below.

Scheme 2

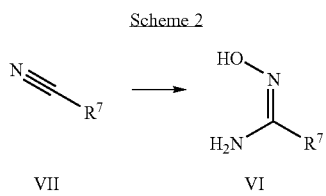

The nitrile components VII are either obtained from commercial sources or made from, e.g. the corresponding carboxylic acids VIII, as shown in Scheme 3, by any of the functional group interconversion methods well known to the person skilled in the art, used to transform a carboxylic acid into the corresponding nitrile. Examples include (i) the reduction of the carboxylic acid VIII into the corresponding carbaldehyde, followed by transformation to the corresponding oxime, and dehydratation of the latter to the corresponding nitrile VII using, e.g. N,N'-carbonyldiimidazole or similar reagents, or (ii) the transformation of the carboxylic acid VIII into the corresponding primary carboxamide, followed by dehydratation to the corresponding nitrile VII, using standard conditions well known to the person skilled in the art, such as those described hereinafter in the Examples.

Scheme 3

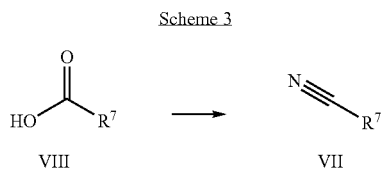

The pyrrolidine-2-carboxylic acids V (see Scheme 1), whereby the substituents $R^1$–$R^7$, and A, are as above defined, can be prepared from compounds of general formula IX by reaction with substituted hydroxylamines X using standard synthetic techniques as hereinafter described in the Examples and shown in Scheme 4.

Scheme 4

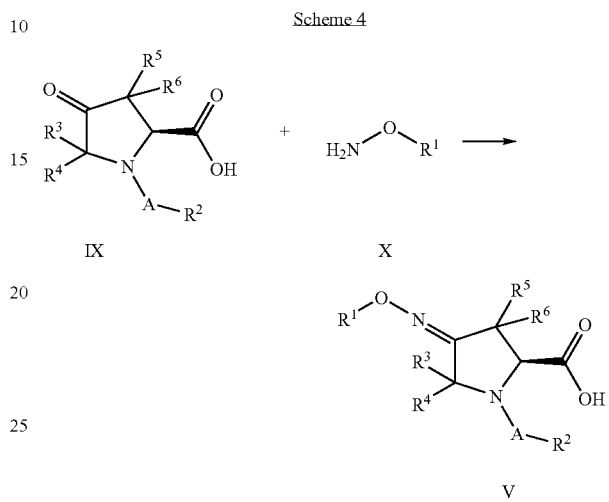

Compounds of formula X are either obtained from commercial sources or prepared from N-Boc-hydroxylamine XI and alkylating agents XII (X=Cl, Br, I), by standard synthetic techniques, as shown in Scheme 5 and described hereinafter in the Examples.

Scheme 5

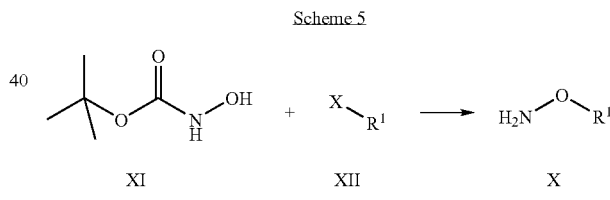

The keto compounds of general formula IX, wherein the substituents $R^1$–$R^7$, and A, are as above defined, can be prepared by oxidation of commercially available, suitably N-protected, 4-hydroxyproline XIII, using standard synthetic techniques as hereinafter described in the Examples and shown in Scheme 6. Alternatively, the compounds of general formula IX can, themselves, be obtained from compounds of formula V through transformation of the oximether into the ketone moiety, e.g. under mild hydrolysis conditions as described hereinafter in the Examples. If, in this scenario, the keto compounds IX are subsequently re-exposed to a different hydroxylamine component X*, such as shown in Scheme 6, then the overall transformation V→IX→V* will correspond to an interchange of $R^1$ within the oximether moiety of compounds of general formula V. The analogous oximether interconversion is possible on the level of the final compounds of general formula I (I→XIV→I*), as shown as well in Scheme 6.

Scheme 6

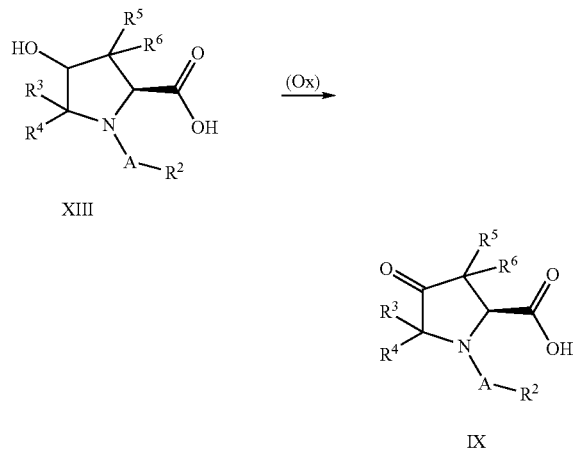

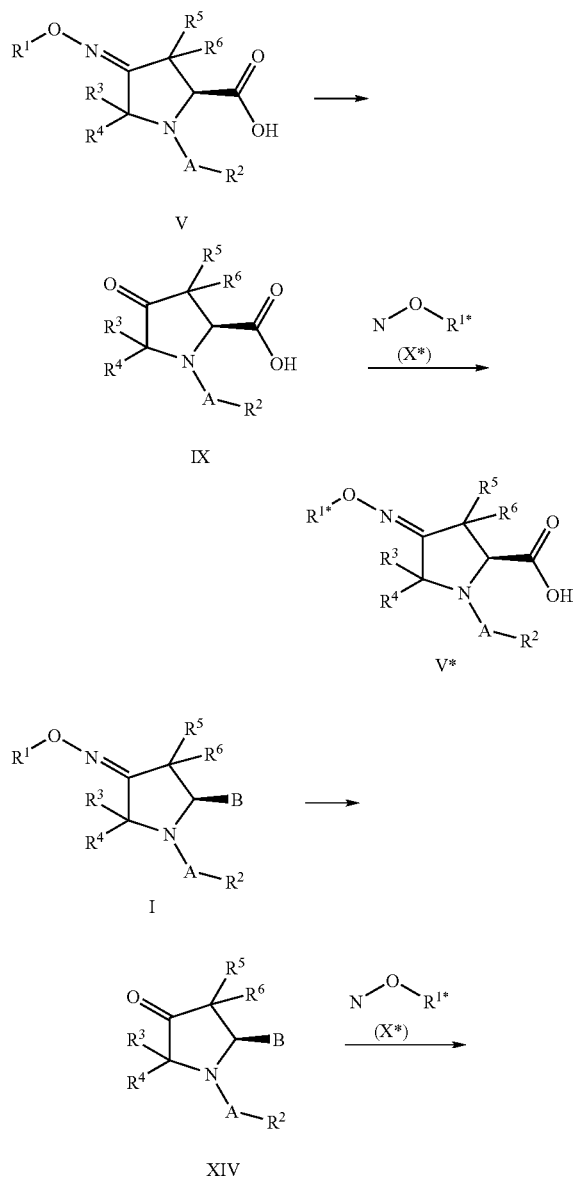

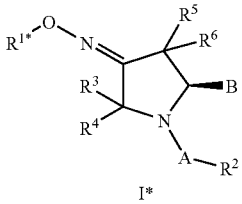

According to another process, pyrrolidine derivatives according to the general formula I, whereby the substituent B is a 1,2,4 oxadiazole of formula (IIb), are prepared from the corresponding amidoxime acid compounds XV, whereby the substituents $R^1$–$R^7$, and A, are as above defined, and carboxylic acids VIII, by well known solution-phase chemistry protocols, such as those described in the Examples and shown in Scheme 7, below.

Scheme 7

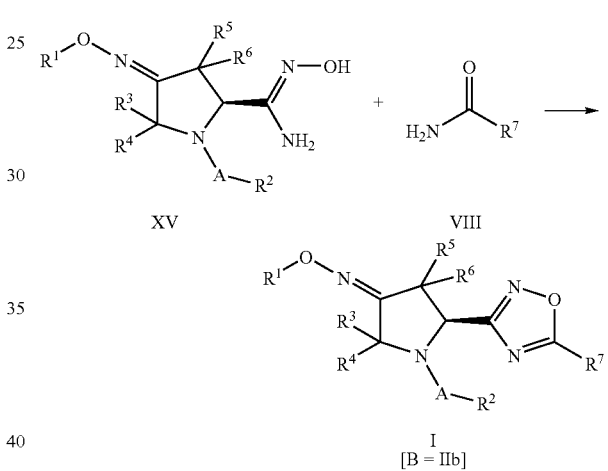

The amidoxime components XV are obtained from the corresponding nitrites XVI, whereby the substituents $R^1$–$R^7$, and A, are as above defined, by treatment of the latter with hydroxylamine under standard conditions well known to the person skilled in the art, such as those described in the Examples and shown in Scheme 8 below. The nitrile components XVI, themselves, are prepared from, e.g. the corresponding carboxylic acids V, wherein the substituents $R^1$–$R^7$, and A, are as above defined, by any of the functional group interconversion methods well known to the person skilled in the art, used to transform, a carboxylic acid into the corresponding nitrile. Examples include (i) the reduction of the carboxylic acid V into the corresponding carbaldehyde, followed by transformation to the corresponding oxime, and dehydratation of the latter to the corresponding nitrile XVI using, e.g. N,N'-carbonyldiimidazole or similar reagents, or (ii) the transformation of the carboxylic acid V into the corresponding primary carboxamide, followed by dehydratation to the corresponding nitrile XVI, using standard conditions well known to the person skilled in the art, such as those described hereinafter in the Examples.

Scheme 8

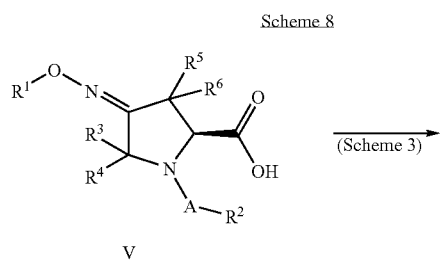

V

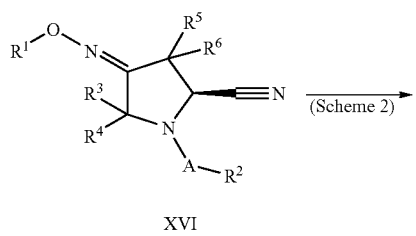

XVI

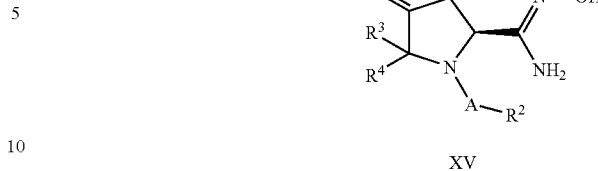

XV

Pyrrolidine derivatives according to the general formula I, wherein the substituent B is a 1,3,4 oxadiazole of formula III and/or IV, may be prepared from the corresponding hydrazide compounds XVII, whereby the substituents $R^1$–$R^7$, and A, are as above defined, by solution-phase chemistry protocols well known to the practicioner skilled in the art, such as those described in the Examples and shown in Scheme 9, below. For example, compounds of formula I wherein substituent B is a 1,3,4 oxadiazole of formula III may be obtained by treatment of XVII with CDI or $CS_2$, under basic conditions, to afford the corresponding products wherein X is O or S, respectively. Alternatively, the hydrazide intermediate XVII can be treated with TMOF, followed by $P_2O_5$ in refluxing toluene, to afford compounds of formula I wherein B is IV.

Scheme 9

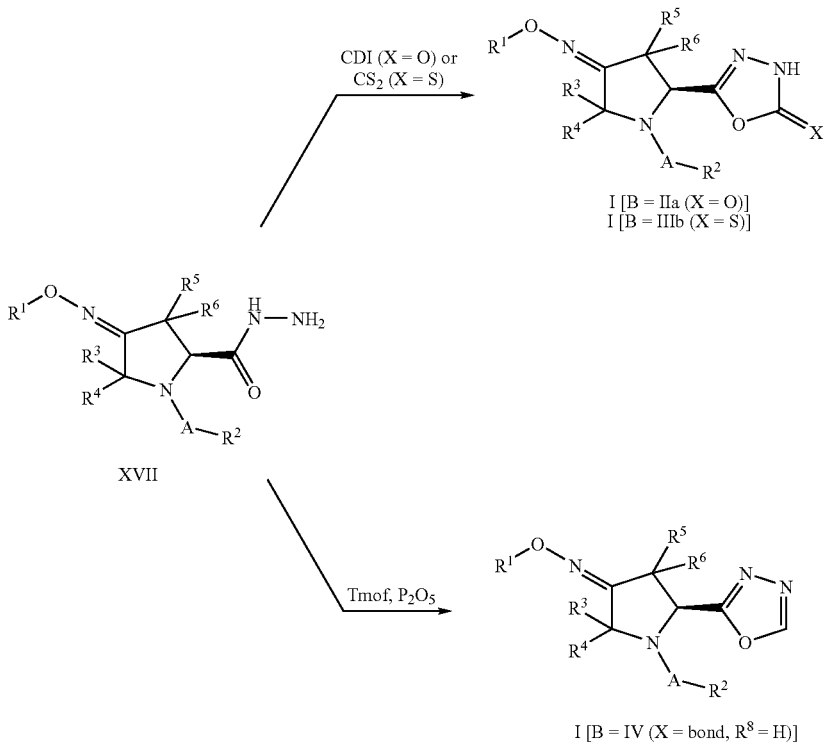

The hydrazide compounds XVII are obtained, e.g., from the corresponding carboxylic acids V, whereby the substituents $R^1$–$R^7$, and A, are as above defined, via the corresponding methylesters XVIII, and subsequent treatment of the latter with hydrazine, under standard conditions well known to the person skilled in the art, such as those described in the Examples and shown in Scheme 10 below.

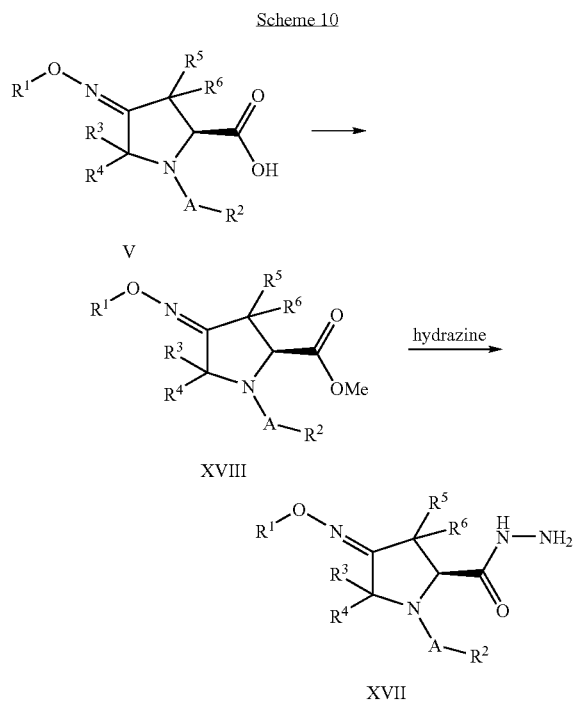

Compounds of general formula I, whereby the substituents $R^1$–$R^8$, and A, are as above defined, are thus accessible from precursors of general formula V/XVIII (see Schemes 1, 7–10 above). Usually, said precursors of formula V/XVIII will initially carry a protecting group for the nitrogen atom of the pyrrolidine ring, such as Boc, Fmoc, or others, hence V' and/or XVIII' (-A-$R^2$=protecting group, PG), as shown in Scheme 11. For the synthesis of the final compounds I, the N-protecting groups of V' and/or XVIII' is typically removed and replaced by a suitable N-substituent, such as, e.g., an acyl group, —C(O)—$R^2$ or a —$SO_2$—$R^2$ group, e.g. by treatment with an acylating agent or sulfonating agent XX. Further compounds of formula (XX) are carboxylating agents, sulfonating agents, sulfonamidating agents, imidating agents, amidating agents, thioamidating agents, or an alkylating agents. The attachment of the desired moiety (-A-$R^2$) at the pyrrolidine nitrogen atom may be performd either after or before the formation of the oxadiazole, or thiadiazole ring, as shown in Scheme 11 (A or B, respectively), and described hereinafter in the Examples. The most appropriate choice of the synthetic sequence protocole will depend on the nature of the substituents $R^1$–$R^8$ (in particular of $R^7$). Preferred acylating agents XX are acid chlorides (XXa), usually employed in conjunction with a suitable tertiary amine base, or a carboxylic acid (XXb), used in conjunction with a peptide coupling agent, e.g. DIC or EDC.

Compounds of formula I wherein A is —(C=O)—O—, —$SO_2$—, —$SO_2$NH—, —C(=NH)—, —(C=O)—NH, —(C=S)—NH, —$CH_2$— may be prepared by using a correspondingly adapted carboxylating agents, sulfonating agents, sulfonamidating agents, imidating agents, amidating agents, thioamidating agents, or alkylating agents, e.g. sulfonyl chlorides, isocyanates, isothiocyanates, chloroformates, substituted alkyl halides, or others to yield sulfonamide, urea, thiourea, carbamate, substituted alkyl derivatives, or others respectively.

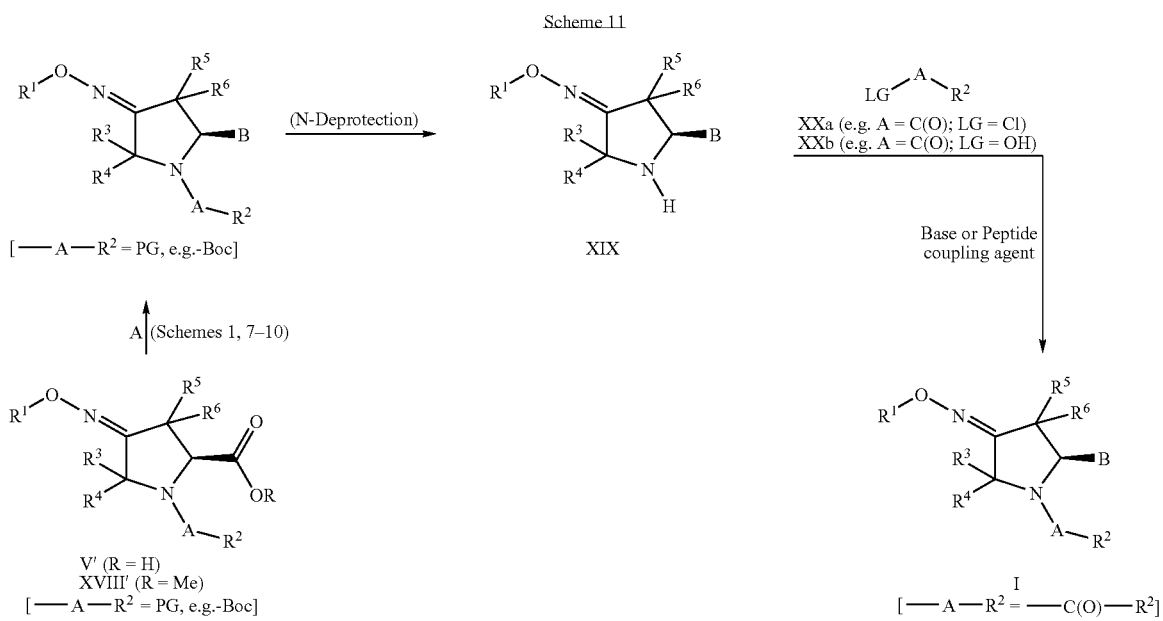

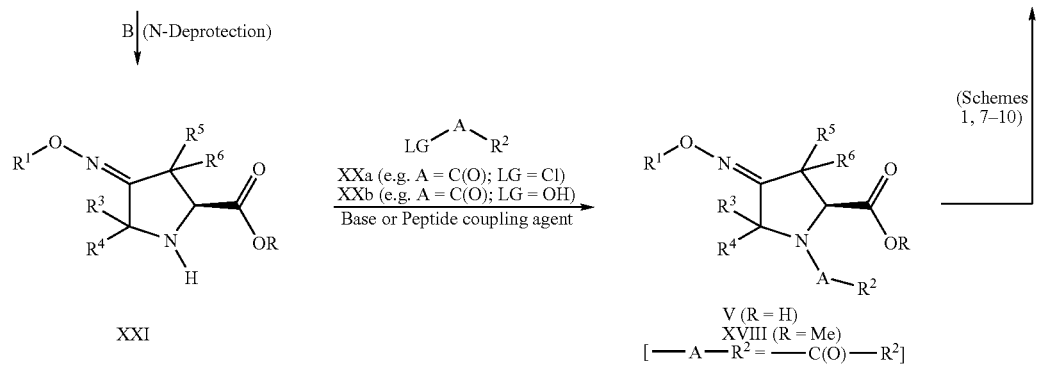

According to a further general process, compounds of formula I can be converted to alternative compounds of formula I', by suitable protection/deprotection/functional group interconversion techniques, well known to the person skilled in the art, as shown in Scheme 12 and described hereinafter in the Examples.

Scheme 12

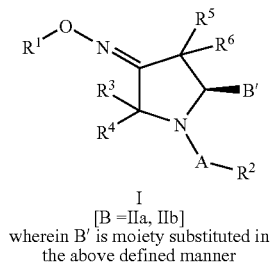

I
[B =IIa, IIb]
wherein B' is moiety substituted in
the above defined manner

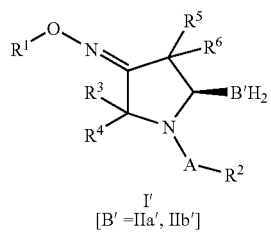

I'
[B' =IIa', IIb']

Examples include:

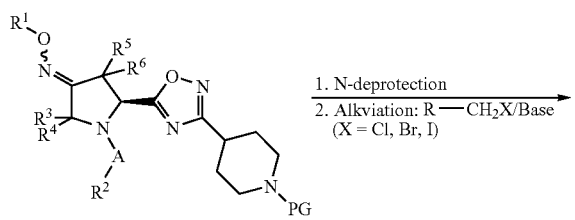

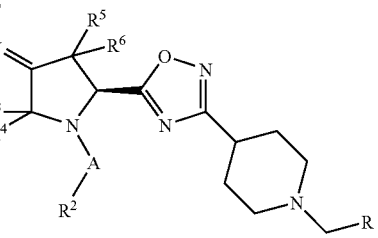

-continued

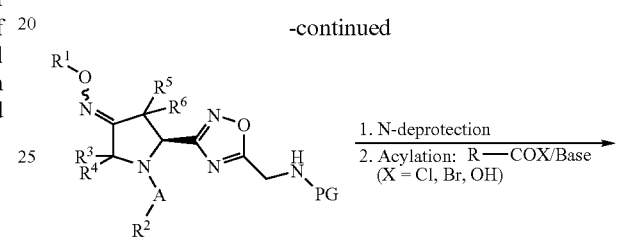

1. N-deprotection
2. Acylation: R—COX/Base
   (X = Cl, Br, OH)

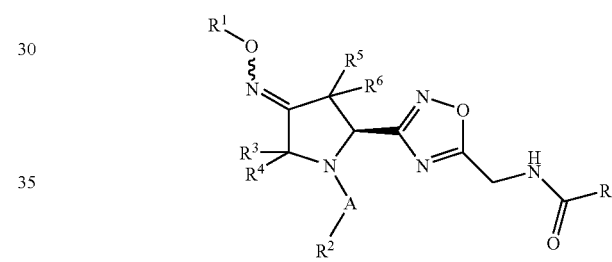

1. Saponification
2. Amide-formation: HNR'R'',
   coupling agent

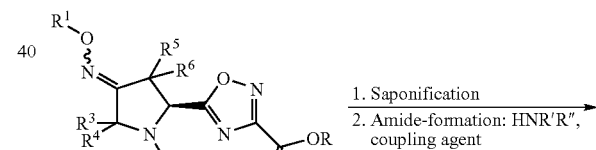

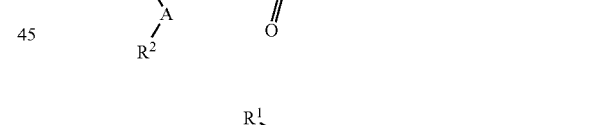

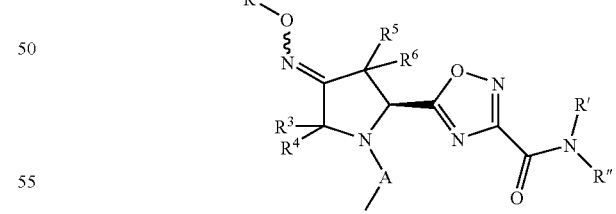

1. Ester-formation: e.g.,
   N-protected amino acid,
   coupling agent
2. N-deprotection

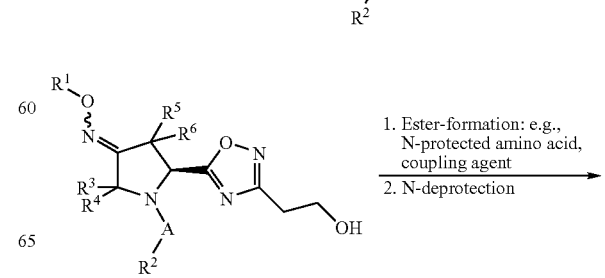

-continued

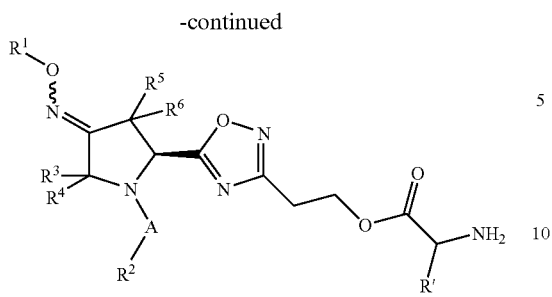

According to yet another process, pyrrolidine derivatives according to the general formula I, are prepared by a novel solid-phase protocol, as outlined in Scheme 13 and described hereinafter in the Examples. For example, for the solid-phase synthesis of compounds of general structure I with B=IIa, the N-Boc-protected pyrrolidine derivative V is reacted with a resin carrying a linker prone to cleavage by nucleophiles, e.g. with Kaiser oxime resin, using standard carbodiimide-mediated coupling conditions well known to the practitioner skilled in the art. Boc-deprotection with dilute TFA in DCM, or with $BF_3 \cdot OEt_2$ in dilute HOAc in DCM, affords compounds of formula XXIV. The latter compound can be treated with acylating agents of general formula XX, whereby the substituents A and $R^2$ are as above defined, and LG could be an appropriate leaving group. Preferred acylating agents XX are acid chlorides (XXa), used in conjunction with a tertiary amine base, or carboxylic acids (XXb), used in conjunction with a peptide coupling agent, such as e.g. DIC, EDC, TBTU, DECP, or others, to yield products of general formula XXIII. Compounds of formula I wherein A is different from the carbonyl functionality are prepared by replacing formula XX with compounds containing the appropriate-functional groups, e.g. sulfonyl chlorides, isocyanates, isothiocyanates, chloroformates, substituted alkyl halides, or others to yield sulfonamide, urea, thiourea, carbamate, substituted alkyl derivatives, or others respectively. In order to obtain the final compounds of general formula I, the linkage to the resin is cleaved by prolonged treatment with amidoximes VI, followed by heating with, e.g., pyridine. The circles in Scheme 13 symbolize the resin beads to which the corresponding compounds are linked during the solid phase synthesis. Other derivatives of formula I are prepared using known modifications to, or variations of, the Scheme 13 reaction sequence. Further to the abovementioned Kaiser oxime resin, other suitable reagents, notably resins, known to a person skilled in the art, could be employed for the solid-phase synthesis of compounds of general formula I.

Scheme 13

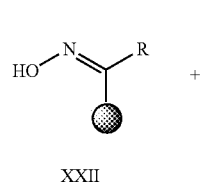

XXII

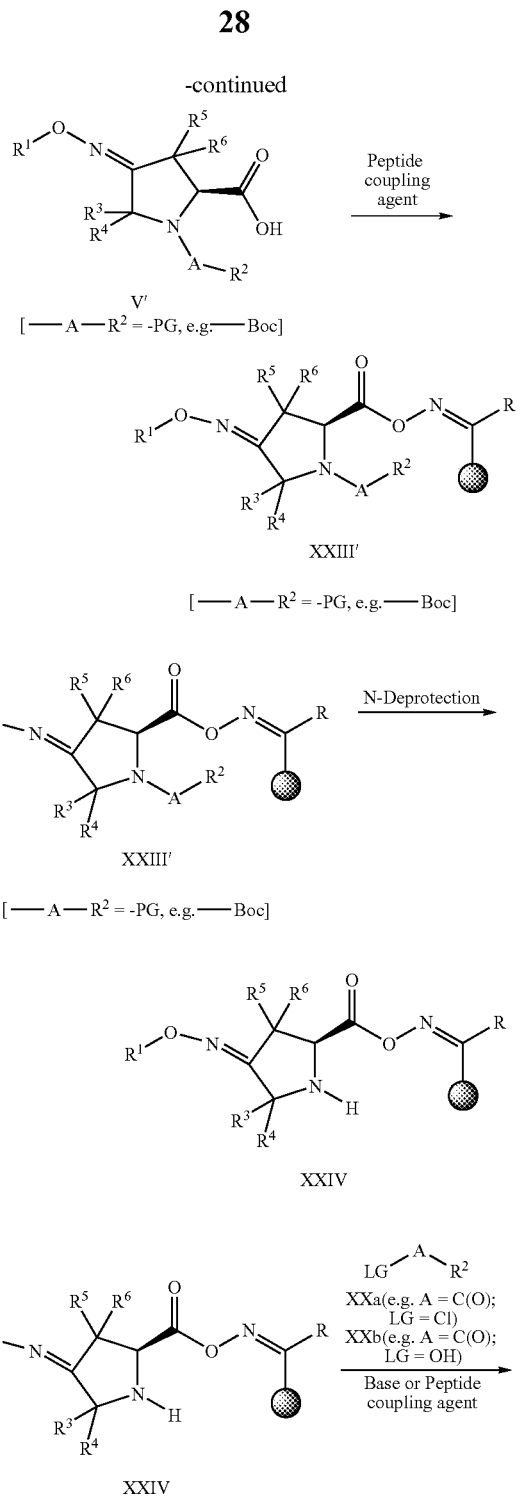

-continued

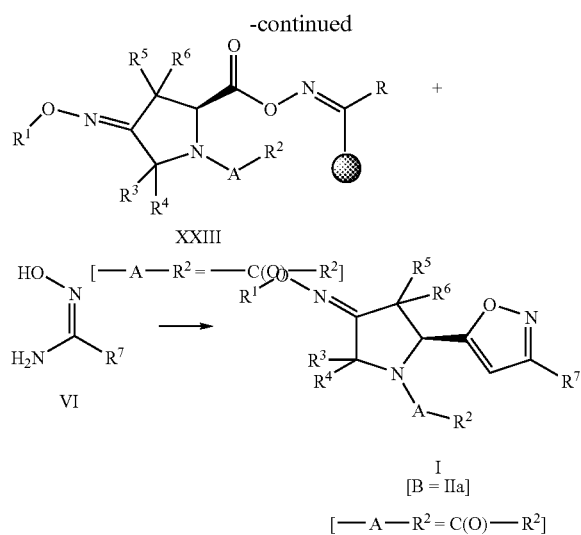

XXIII

I
[B = IIa]

[—A—R² = C(O)—R²]

The reaction sequences outlined in the above Schemes provide enantiomerically pure compounds of formula I, if enantiomerically pure starting materials are used. (R)- as well as (S)-enantiomers can be obtained depending upon whether (R)- or (S)-forms of commercially available compounds of formulas V–VIII, X, and/or XX were used as the starting materials.

However, the reaction sequences outlined in the above Schemes usually provide mixtures of (E)- and (Z)-isomers with respect to the substituents on the exocyclic double bond of the pyrrolidine ring. In all cases studied, these (E)/(Z)-isomers could be separated by standard chromatography techniques well known to the person skilled in the art, such as by reversed phase high-pressure liquid chromatography (HPLC) or silica gel flash chromatography (FC). Alternatively, either one of the (E)/(Z)-isomers could successively be enriched by selective crystallisation in appropriate solvents or solvent mixtures. The assignment of the absolute configuration of the exocyclic double bond was performed using NMR-techniques well described in the literature as will be known to the practitioner skilled in the art (for configurational assignments of e.g. oxime functionalities, see e.g. E. Breitmaier, W. Voelter Carbon-13 NMR Spectroscopy, 3rd Ed, VCH, 1987, p. 240). In order to increase the overall yields of the preferred isomer (usually the (Z)-isomer), the less preferred isomer (usually the (E)-isomer) could be recycled by deliberate re-isomerization in organic solvents containing traces of acid, such as HCl, followed again by (E)/(Z)-separation through chromatography and/or crystallization, as illustrated in Scheme 14.

Scheme 14

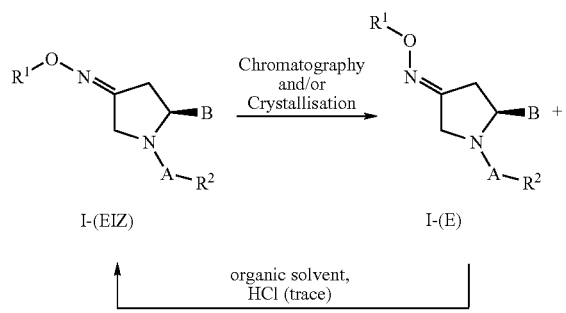

-continued

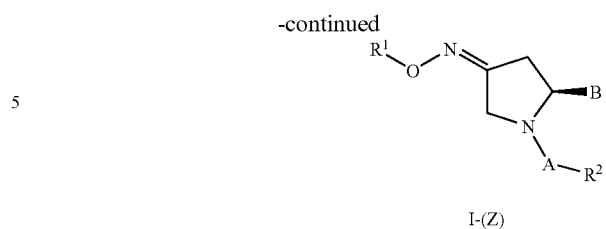

I-(Z)

If the above set out general synthetic methods are not applicable for obtaining compounds according to formula I and/or necessary intermediates for the synthesis of compounds of formula I, suitable methods of preparation known by a person skilled on the art should be used. In general, the synthesis pathways for any individual compound of formula I will depend on the specific substitutents of each molecule and upon the ready availability of intermediates necessary; again such factors being appreciated by those of ordinary skill in the art. For all the protection, deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley-Interscience, 1991.

Compounds of this invention can be isolated in association with solvent molecules by crystallization from evaporation of an appropriate solvent. The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salt may be formed or interconverted using ion-exchange resin techniques.

A final aspect of the present invention is related to the use of the compounds according to formula I for the treatment of preterm labor, premature birth, dysmenorrhea, preferably the compounds of formula (I) are suitable for the modulation of the Oxytocin receptor, the use of said compounds for the preparation of pharmaceutical compositions for the modulation of the oxytocin receptor as well as the formulations containing the active compounds according to formula I. Said modulation of the oxytocin receptor is viewed as a suitable approach for the treatment of preterm labor, premature birth and dysmenorrhea. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides; compounds for use as a medicament.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine oxadiazole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a desintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrrolidine derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, 17th Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The HPLC, NMR and MS data provided in the examples described below were obtained as followed. The following abbreviations are hereinafter used in the accompanying examples: min (minute), hr (hour), g (gram), mmol (millimole), m.p. (melting point), eq (equivalents), mL (milliliter), μL (microliters), mL (milliliters), ACN (Acetonitrile), Boc (butoxycarbonyl), $CDCl_3$ (deuterated chloroform), CDI (carbonyldiimidazole), cHex (Cyclohexanes), DCM (Dichloromethane), DECP (Diethylcyanophos-phonate), DIC (Diisopropyl carbodiimide), DMAP (4-Dimethylaminopyridine) DMF (Dimethylformamide), DMSO (Dimethylsulfoxide), $DMSO-d_6$ (deuterated dimethylsulfoxide), EDC (1-(3-Dimethyl-amino-propyl)-3-ethylcarbodiimide), EtOAc (Ethyl acetate), $Et_2O$ (Diethyl ether), Fmoc (9-fluorenylmethoxycarbonyl), HOBt (1-Hydroxybenzotriazole), Kaiser oxime resin (4-Nitrobenzophenone oxime resin); $K_2CO_3$ (potassium carbonate), NaH (Sodium hydride), $NaHCO_3$ (Sodium bicarbonate), nBuLi (n Butyllithium), TBTU (O-Benzotriazolyl-N,N,N',N'-tetramethyluronium-tetrafluoroborate), TEA (Triethyl amine), TFA (Trifluoroacetic acid), THF (Tetrahydrofuran), TMOF (trimethylorthoformate), $MgSO_4$ (Magnesium sulfate), PetEther (Petroleum ether), rt (room temperature).

EXAMPLES

Intermediate 1: (2S)-1-(tert-butoxycarbonyl)-4-oxo-2-pyrrolidinecarboxylic acid (cf. Scheme 6, compound XIII)

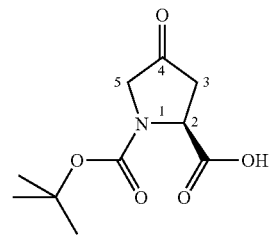

Commercial (2S,4R)-1-(tert-butoxycarbonyl)-4-hydroxy-2-pyrrolidinecarboxylic acid (30 g, 0.13 mol) was dissolved in acetone (500 ml). A mechanical stirrer was placed in the flask and the solution stirred vigorously. A freshly made solution of 8N chromic acid was prepared by dissolving chromium trioxide (66.7 g, 0.667 mol) in water (40 ml), adding concentrated sulphuric acid (53.3 ml) and adding enough water to bring the solution volume to 115 ml. The 8N chromic acid solution (115 ml) was then added dropwise over a period of 30 minutes with continued vigorous stirring, the reaction's exotherm being maintained at the optimal temperature of 25° C. by the use of an ice bath. After the complete addition of the chromic acid, the reaction mixture was stirred for a further 15 minutes—maintaining the optimal temperature of 25° C. The reaction mixture was then quenched by the addition of methanol (20 ml). Exotherm controlled by the use of an ice bath and, if necessary, direct addition of a small amount of crushed ice to the reaction mixture itself. The reaction mixture was filtered through a Celite pad and then concentrated in vacuo. The resulting acidic solution was then extracted with ethyl acetate (3×300 ml) and the combined organic layers washed with brine (2×100 ml). Organics then dried with magnesium sulfate and concentrated in vacuo. Crude product recrystallised from ethyl acetate to give the white crystalline product, (2S)-1-(tert-butoxycarbonyl)-4-oxo-2-pyrrolidinecarboxylic acid (22.55 g, 76%). The antipodal intermediate, (2R)-1-(tert-butoxycarbonyl)-4-oxo-2-pyrrolidinecarboxylic acid, was made according to the same protocol, starting from commercial (2R,4S)-1-(tert-butoxycarbonyl)-4-hydroxy-2-pyrrolidinecarboxylic acid.

1H NMR (360 MHz, CDCl3); 1.4 (m, 9H), 2.5–3.0 (m, 2H), 3.7–3.9 (m, 2H), 4.75 (dd, 1H)

Intermediate 2: (2S,4EZ)-1-(tert-butoxycarbonyl)-4-(methoxyimino)-2-pyrrolidine-carboxylic acid (cf. Scheme 4, compound V)

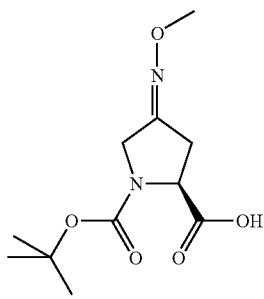

A solution was made containing (2S)-1-(tert-butoxycarbonyl)-4-oxo-2-pyrrolidinecarboxylic acid (Intermediate 1, 5.0 g, 21 mmol) and O-methylhydroxylamine hydrochloride (2.7 g, 32.8 mmol) in chloroform (100 ml) containing triethylamine (5.5 g, 55 mmol). The reaction mixture was then stirred at ambient temperature overnight, prior to removal of solvent. The resultant crude reaction mixture was dissolved in ethyl acetate (150 ml) and washed rapidly with 1N HCl (40 ml). The acidic layer was then extracted with ethyl acetate (3×20 ml) and the combined organic layers washed with brine before drying over magnesiom sulfate, filtering and removal of solvent in vacuo. The desired product (5.3 g, 94%) was isolated as a pale yellow oil.

$^1$H NMR (400 MHz, CDCl$_3$); 1.45 (m, 9H), 2.8–3.2 (m, 2H), 3.9 (s, 3H), 4.2 (m, 2H), 4.5–4.7 (m, 1H).

Intermediate 3: (2S,4EZ)-1-(tert-butoxycarbonyl)-4-(ethoxyimino)-2-pyrrolidinecarboxylic acid (cf. Scheme 4, compound V)

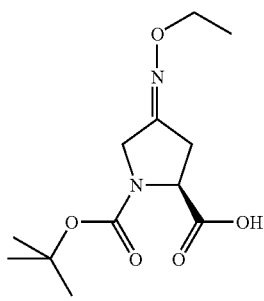

A solution was made containing (2S)-(tert-butoxycarbonyl)-4-oxo-2-pyrrolidinecarboxylic acid (Intermediate 1, 5.0 g, 22 mmol) and O-ethylhydroxylamine hydrochloride (6.4 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesiom sulfate, filtering and removal of solvent in vacuo. The desired product (5.5 g, 93%) was isolated as a pale yellow oil.

$^1$H NMR (400 MHz, DMSO); 1.3 (t, 3H), 1.55 (m, 9H), 2.9–2.7 (m, 1H), 3.4–3.1 (m, 1H), 4.1–4.3 (m, 4H), 4.6 (m, 1H), 12–13.5 (br, 1H).

Intermediate 4: (2S,4EZ)-4-[(allyloxy)imino]-1-(tert-butoxycarbonyl)-2-pyrrolidinecarboxylic acid (cf. Scheme 4, compound V)

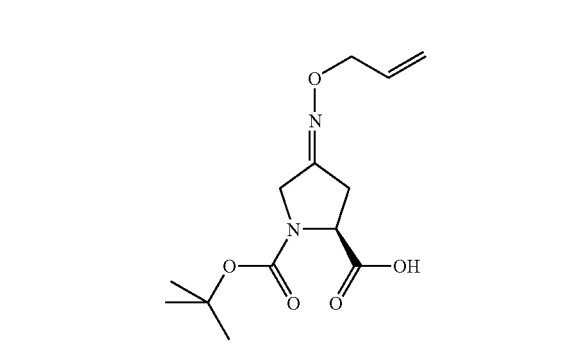

A solution was made containing (2S)-1-(tert-butoxycarbonyl)-4-oxo-2-pyrrolidinecarboxylic acid (Intermediate 1, 5.0 g, 22 mmol) and O-allylhydroxylamine hydrochloride monohydrate (7.2 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesium sulfate, filtering and removal of solvent in vacuo. The desired product (5.9 g, 94%) was isolated as a pale yellow oil.

$^1$H NMR (400 MHz, CDCl$_3$); 1.5 (m, 9H), 2.8–3.2 (m, 2H), 4.2 (m, 2H), 4.5–4.7 (m, 3H), 5.25 (m, 2H), 5.9 (m, 1H), 11.1 (broad S, 1H).

Intermediate 5: (2S,4EZ)-1-(tert-butoxycarbonyl)-4-{[(4-methoxybenzyl)oxy]imino}-2-pyrrolidine-carboxylic acid (cf. Scheme 4, compound V)

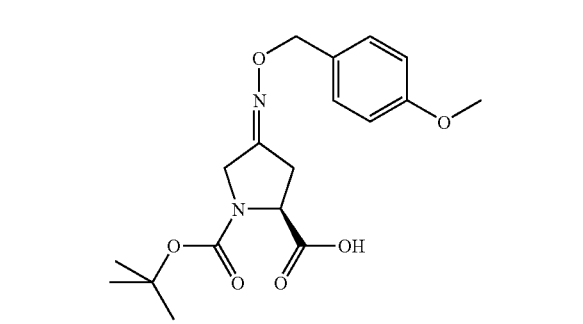

The same method as employed in the preparation of Intermediate 2, but starting from (2S)-1-(tert-butoxycarbonyl)-4-oxo-2-pyrrolidinecarboxylic acid (Intermediate 1) and 1-[(aminooxy)methyl]-4-methoxybenzene (intermediate 6), gave the title compound as a gum in a 85% yield.

$^1$H NMR (400 MHz, DMSO); 1.5 (m, 9H), 2.7–2.9 (m, 1H) 3.9 (s, 3H), 4.2 (m, 3H), 4.6 (m, 1H), 5.15 (s, 2H), 7.1 (d, 2H), 7.45 (d, 2H).

Intermediate 6: 1-[(aminooxy)methyl]-4-methoxybenzene (cf. Scheme 5, compound X)

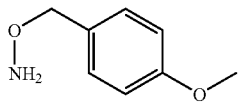

A solution was made of N-Boc-hydroxylamine (2.0 g, 17.1 mmol) in dry THF (60 ml). Sodium hydride (1.1 g of a 60% suspension in paraffin oil, 25.7 mmol) was then added and the suspension stirred. A catalytic amount of KI was then added to the reaction prior to the cautious addition of 4-methoxybenzyl chloride (3.2 g, 20.4 mmol). The reaction was then allowed to stir overnight before removal of solvent in vacuo. The residue was taken up with diethyl ether (100 ml) and HCl gas bubbled in for 20 minutes, causing the start of precipitation of the product. The flask was stoppered and left to stand overnight. The product was then filtered off as a off-white wax (39–52% yield according to varying batches).

$^1$H NMR (400 MHz, D$_2$O); 3.8 (s, 3H), 5 (s, 2H), 7.0 (d, 2H), 7.4 (d, 2H).

Intermediate 7: Non-commercial Amidoximes

Method A: e.g. N'-hydroxyethanimidamide (acetamidoxime) (cf. Scheme 2, compound VI)

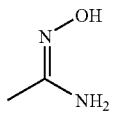

45 ml of high purity acetonitrile was added to 90 ml of 50% hydroxylamine/50% water (w/w), and stirred with a magnetic stirrer at 25° C. Most of the time, crystalline N'-hydroxyethanimidamide separated. The mixture was stirred 24 h at room temperature to complete formation of crystals and filtered the next day. In cases, where no solid separated initially, a small amount of solution was taken out, evaporated, and the crystals formed used to seed the bulk solution. The product was purified as follows: the crystals were filtered and then dissolved in a non-polar solvent (perfluorohexane) by heating, and cooled overnight at ambient temperature for recrystallization. The crystalline material was then filtered and washed with perfluorohexane. The desired product, N'-hydroxyethanimidamide, had a melting point of 136° C.–138° C., and the yield approximately 56%.

Method B: e.g. tert-butyl-2-amino-2-(hydroxyimino)ethyl-carbamate (Scheme 2, compound XI)

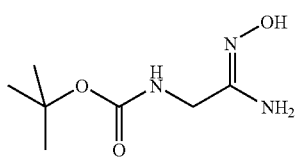

Triethylamine (535 µl, 3.84 mmol) was added to a solution of tert-butyl cyanomethyl-carbamate (500 mg, 3.20 mmol) and hydroxylamine hydrochloride (227 mg, 3.84 mmol) in ethanol (10 ml). The reaction mixture was heated overnight at 80° C. The resultant solution was then evaporated in vacuo. Ethylacetate (10 ml) was added to the residue and triethylamine hydrochloride was removed by filtration. The solution was then evaporated in vacuo to give the crude product.

$^1$H NMR (360 MHz, DMSO); 1.53 (s, 9H), 3.62–3.63 (d, 2H), 5.33–5.44 (s, 2H) 7.10(t, 1H), 8.94(s, 1H).

Similarly, using Method B, and starting from the appropriate commercial carbonitriles and hydroxylamine hydrochloride, the following, related amidoxime intermediates were obtained: (2RS)-N',2-dihydroxybutanimidamide, (1S, 2R)-N',2-dihydroxycyclohexane-carboximidamide, N',3-dihydroxypropanimidamide, N',2-dihydroxyethanimidamide, (2RS)-N',2-dihydroxy-2-phenylethanimidamide, tert-butyl 4-[amino(hydroxyimino)methyl]-1-piperidinecarboxylate, tert-butyl (3RS)-3-[aminohydroxyimino)methyl]-1-piperidinecarboxylate, tert-butyl (2RS)-2-[amino(hydroxyimino)methyl]-1-piperidinecarboxylate, ethyl aminohydroxyimino)ethanoate.

Intermediate 8: (2S,4EZ)-1-([1,1'-biphenyl]-4-ylcarbonyl)-N'-hydroxy-4-(methoxyimino)-2-pyrrolidinecarboximidamide (Scheme 8, compound XV)

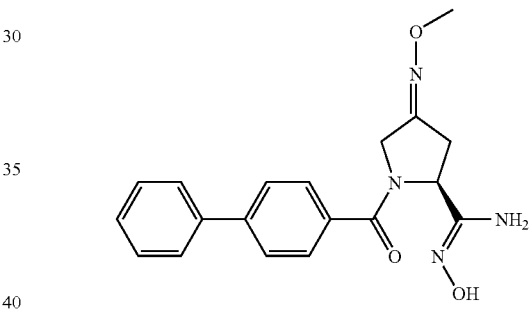

1-(tert-butoxycarbonyl)-4-(methoxyimino)-2-pyrrolidine carboxylic acid (Intermediate 2, 95.9 g, 0.371 mol) was charged into a 3 L flange flask, fitted with an overhead stirrer, nitrogen inlet/outlet and temperature probe. Dry THF (1.15 L) was then added to the flask, and the solution was cooled to –20° C. prior to adding triethylamine (52 mL, 0.371 mol). The solution was then stirred for 10 minutes. Ethyl chloroformate (35 ml, 0.371 mol) was added to the solution over 10 minutes, maintaining the temperature around –20° C. The reaction was then stirred for a further 30 minutes at this temperature. A solution of ammonia saturated THF solution was prepared by bubbling ammonia through 250 mL of dry THF for 15 minutes at –78° C. The ammonia solution was added to the reaction flask via cannula over 10 minutes, maintaining the reaction temperature below –25° C. to control the exotherm. The solution was allowed to attain room temperature over 2 hours, and was then stirred for a further hour. The solvent was removed from the reaction in vacuo and the residue was partitioned between dichloromethane (500 mL) and water (500 mL). After separation, the organic layer was washed with 3×250 mL of water, the combined aqueous layers were then washed with 2×250 mL of DCM and this DCM was back-washed with 100 ml of water. The combined organic layers were then dried over sodium sulphate, filtered and the solvent removed in vacuo. The desired product, tert-butyl (2S,4EZ)-2-(aminocarbonyl)-4-(methoxyimino)-1-pyrrolidinecarboxylate, was obtained as a white amorphous solid (85.8 g, 90%).

¹H NMR (400 MHz, DMSO); 1.5 (s, 9H), 2.65 (m, 1H), 3.15 (m, 1H), 3.9 (s, 3H), 4.2 (m, 2H), 4.5 (m, 1H), 7.2 (m, 1H), 7.65 (m, 1H).

tert-butyl (2S,4EZ)-2-(aminocarbonyl)-4-(methoxyimino)-1-pyrrolidinecarboxylate (20 g, 77.7 mmol) was charged into a 1 L round bottomed flask under an inert atmosphere. Dry dichloromethane (140 mL) was then added to the flask, followed by TFA (60 mL). The reaction was stirred at room temperature for 90 minutes, monitoring the disappearance of starting material by tlc (10% MeOH in DCM). Toluene (200 mL) was then added to the reaction mixture, and the solvents removed in vacuo. The residue was re-dissolved in DCM (200 mL), cooled to −5° C. and triethylamine (43 mL, 311 mmol) was added (exotherm). [1,1'-biphenyl]-4-carbonyl chloride (16.8 g, 77.7 mmol) was added to the reaction mixture, which was stirred at room temperature for 1.5 h. At this point, further DCM (500 mL) and 1M HCl (250 mL) was added. The mixture was stirred vigorously and the precipitate filtered off. The filtrate layers were separated, the organic layer being washed with 1M HCl (250 mL) and saturated bicarbonate (250 mL). The basic aqueous layer was back washed with DCM (250 mL), and the combined organics were dried over magnesium sulphate, filtered and the filtrate was concentrated to ca. 200 mL. The resulting slurry was filtered to give the desired product, (2S,4EZ)-1-([1,1'-biphenyl]-4-ylcarbonyl)-4-(methoxyimino)-2-pyrrolidinecarboxamide as an off-white solid (7.3 g, 28%). A further quantity of less pure material (7.9 g, 30%) could be obtained by adding hexane (125 mL) to the filtrate.

¹H NMR (400 MHz, DMSO); 2.6 (m, 1H), 3.2 (m, 1H), 3.8 (m, 3H), 4.1–4.5 (m, 2H), 4.9 (m, 1H), 7.2–8.0 (m, 11H).

(2S,4EZ)-1-([1,1'-biphenyl]-4-ylcarbonyl)-4-(methoxyimino)-2-pyrrolidinecarboxamide (7.46 g, 22.1 mmol) was charged into a round bottomed flask, pyridine (400 mL) and p-toluenesulfonyl chloride (4.21 g, 22.1 mmol) was added. The resulting suspension was heated to 80° C., for 4 hours. The solvent was removed in vacuo and the residue dissolved in DCM (400 mL), the solution being washed with 1M HCl (2×75 mL) and saturated bicarbonate (70 mL) before drying over sodium sulphate, filtration and removal of solvent in vacuo. Purification by short path silica gel chromatography, eluting initially with dichloromethane to remove less polar material and subsequently with 1% MEOH in DCM, gave the desired compound, (2S,4EZ)-1-([1,1'-biphenyl]-4-ylcarbonyl)-4-(methoxyimino)-2-pyrrolidinecarbonitrile, as an off-white solid (4.2 g, 60%).

¹H NMR (400 MHz, DMSO); 3.0 (m, 1H), 3.2 (m, 1H), 3.7 (m, 3H), 4.2 (m, 1H), 4.5 (m, 1H), 5.4 (m, 1H), 7.4–7.8 (m, 9H).

According to the general method outlined above for the synthesis of Intermediates 8, triethylamine (1.94 ml, 13.94 mmol) was slowly added to a suspension of (2S,4EZ)-1-([1, 1'-biphenyl]-4-ylcarbonyl)-4-(methoxyimino)-2-pyrrolidinecarbonitrile (3.71 g, 11.62 mmol) and hydroxylamine.hydrochloride (0.97 g, 13.94 mmol) in ethanol (150 ml), under stirring. The reaction mixture was allowed to stir at 80° C. for 16 h, and then cooled to ambient temperatures. The solvent was removed by evaporation and the solid was suspended in water (100 ml) then filtered. The solid was washed with diethyl ether (2×100 ml) whilst on the sinter and then dried in vacuo at 40° C., to give the desired product, (2S,4EZ)-1-([1,1'-biphenyl]-4-ylcarbonyl)-N'-hydroxy-4-(methoxyimino)-2-pyrrolidinecarboximidamide (3.35 g, 82%).

¹H-NMR (400 MHz, DMSO): 2.6–2.7 (m, 1H), 2.9–3.1 (m, 1H), 3.6–3.75 (m, 3H), 4.0–4.2 (m, 1H), 4.2–4.4 (m, 1H), 4.6 (m, 0.5H), 5.1 (m, 0.5H), 5.5 (m, 2H), 7.4–7.8 (m, 9H), 9.2–9.4 (m, 1H).

Intermediate 9: tert-butyl (2S,4EZ)-2-(hydrazinocarbonyl)-4-(methoxyimino)-1-pyrrolidinecarboxylate (Scheme 10, compound XVII)

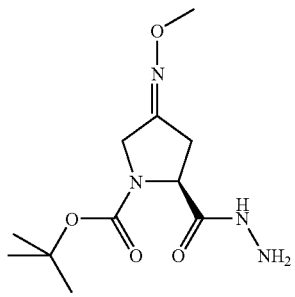

A solution was made containing, e.g., (4EZ)-1-(tert-butoxycarbonyl)-4-(methoxyimino)-2-pyrrolidinecarboxylic acid (Intermediate 2, 17.81 mmoles; 4.6 gr) in a 1:1 mixture of methanol and toluene (250 mL). Trimethylsilyl diazomethane (32.5 mL of a 2M solution in hexanes, 59 mmol) was then added dropwise to the sirred solution at room temperature under nitrogen. After completion of the evolution of nitrogen gas, the resulting yellow solution was evaporated in vacuo, and the residue re-dissolved in DCM and washed with NH₄Clsat and 10% NaHCO₃, and brine, dried over Na₂SO₄ and evaporated in vacuo, giving the desired compound, 1-tert-butyl 2-methyl (2S,4EZ)-4-(methoxyimino)-1,2-pyrrolidinedicarboxylate, as a yellow oil (4.0 g, 83%).

1-tert-butyl 2-methyl (2S,4EZ)-4-(methoxyimino)-1,2-pyrrolidinedicarboxylate (1.95 mmoles; 530 mg) was dissolved in 4 mL of MeOH and a solution of 4 mL of MeOH and 1.5 mL (d=1.03; 30.86 mmoles) of 80% hydrazine.hydrate was added (final c(NH₂NH₂)=13%). The reaction mixture was agitated for 2 days. Solvents were evaporated in vacuo and the residue re-dissolved in MeOH and evaporated (3×). The desired compound, tert-butyl (2S,4EZ)-2-(hydrazinocarbonyl)-4-(methoxyimino)-1-pyrrolidinecarboxylate, was isolated as a yellow oil (500 mg; 94%).

¹H-NMR (CDCl₃): 1.47 (s, 9H, CH3), 2.8–3.2 (m, 2H, CH2), 3.87 (s, 3H, CH3-O), 3.95–4.3 (m, 2H, CH2), 4.52 (m, 1H, CH—N). MS(APCI⁺): 273.0, 545.4(2M⁺¹).

Intermediate 10: 2'-methyl[1,1'-biphenyl]-4-carboxylic acid

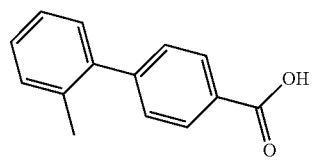

To a mixture of 4-bromobenzoic acid (30 g, 0.15 mol), 2-methylphenylboronic acid (24 g, 0.15 mol), sodium carbonate (250 g) in toluene (500 mL) and water (500 mL) was added tetrakis-triphenylphosphine palladium(0) (9 g, 0.0074 mol) under nitrogen atmosphere. The reaction mixture was refluxed for 10 h. After this time, 100 ml of 10% NaOH were added to the reaction mixture, the aqueous layer was separated and washed with toluene (2×200 mL). Acidification of the aqueous layer with 3N HCl solution gave a solid product, which was filtered, washed with water and dried. The crude product was then crystallised from toluene to yield 2'-methyl [1,1'-biphenyl]-4-carboxylic acid (20 g, 62.5%). Conversely, the product could also be obtained from 1-bromo-2-methylbenzene and 4-carboxybenzeneboronic acid, using analogous conditions.

$^1$H NMR (300 MHz, DMSO); 2.2 (s, 3H), 7.2–7.4 (m, 4H), 7.43 (d, J=9 Hz, 2H), 7.99 (d, J=9 Hz, 2H), 13 (b, 1H).

Similarly, using the appropriate commercial boronic acids and arylbromides, the following, related intermediate 1,1'-biphenyl derivatives (12) were obtained: 4'-methyl[1,1'-biphenyl]-4-carboxylic acid; 2',3-dimethyl[1,1'-biphenyl]-4-carboxylic acid; 2',6'-dimethyl[1,1'-biphenyl]-4-carboxylic acid; 2-methyl[1,1'-biphenyl]-4-carboxylic acid; 3-methyl [1,1'-biphenyl]-4-carboxylic acid; 2,2'-dimethyl[1,1'-biphenyl]-4-carboxylic acid; 2'-methoxy[1,1'-biphenyl]-4-carboxylic acid; 3'-methoxy[1,1'-biphenyl]-4-carboxylic acid; 4'-methoxy[1,1'-biphenyl]-4-carboxylic acid; 2'-chloro[1,1'-biphenyl]-4-carboxylic acid; 3'-chloro[1,1'-biphenyl]-4-carboxylic acid; 4'-chloro[1,1'-biphenyl]-4-carboxylic acid; 3',4'-dichloro[1,1'-biphenyl]-4-carboxylic acid; 2'-(trifluoromethyl)[1,1'-biphenyl]-4-carboxylic acid; 3'-(trifluoromethyl)[1,1'-biphenyl]-4-carboxylic acid; 2'-cyano[1,1'-biphenyl]-4-carboxylic acid; 2',4'-difluoro[1,1'-biphenyl]-4-carboxylic acid; 4-(2-pyridinyl)benzoic acid; 4-(3-pyridinyl)benzoic acid; 4-(4-pyridinyl)benzoic acid; 4-(5-pyrimidinyl)benzoic acid; and others.

Intermediate 11: 4-(3-methyl-2-pyridinyl)benzoic acid

A mixture of 2-bromo-3-methylpyridine (22.5 g, 0.1312 mol), 4-(hydroxymethyl)phenylboronic acid (25 g, 0.164 mol), Pd(PPh$_3$)$_4$ (9.5 g, 0.0082 mol), and sodium carbonate (200 g in 500 ml of water) in toluene (750 ml) were refluxed under nitrogen atmosphere for 15 h. Separated the toluene layer and distilled under reduced pressure to give a residue. The residue was then purified by column chromatography to yield [4-(3-methyl-2-pyridinyl)phenyl]methanol (12 g, 47%).

To a solution of [4-(3-methyl-2-pyridinyl)phenyl]methanol (12 g, 0.06 mol) in dry DMF (150 mL) was added pyridiniumdichromate (91 g, 0.24 mol) and stirred at RT for 3 days. The reaction mixture was poured into water and extracted with ethyl acetate (250 mL). The organic layer was washed with water, brine, dried and concentrated. The crude was purified by column chromatography over silica gel to give 4-(3-methyl-2-pyridinyl)benzoic acid (3 g, 25%) as white solid.

$^1$H NMR (300 MHz, DMSO); 2.3 (s, 3H), 7.33 (dd, J=7.5 Hz, 5 Hz, 1H), 7.67 (d, J=8 Hz, 2H), 7.75 (d, J=7.5 Hz, 1H), 8.01 (d, J=8 Hz, 2H), 8.50 (d, J=5 Hz, 1H), 13 (b, 1H).

Intermediate 12: 4-(1-oxido-3-pyridinyl)benzoic acid

To a mixture of 4-tolylboronic acid (38 g, 0.28 mol), 3-bromopyridine (44 g, 0.28 mol), Na$_2$CO$_3$ (200 g) in toluene (500 ml) and water (500 ml) was added Pd(PPh$_3$)$_4$ (16 g, 0.014 mol), and refluxed for 16 h. The reaction mixture was cooled, and the separated organic layer was washed with water and brine, and dried. The solvent was removed to give 4-(3-pyridyl)toluene (42 g, 90%).

To a mixture of 4-(3-pyridyl)toluene (35 g, 0.207 mol) in pyridine (400 ml) and water (400 ml) was added KMnO$_4$ (163 g, 1.03 mol) in portions and refluxed for 12 h. The reaction mixture was filtered through celite and acidified with conc. HCl. The product was washed with water and dried to give 4-(3-pyridyl)benzoic acid (32 g, 76%) as a white solid. To a mixture of 4-(3-pyridyl)benzoic acid (22 g, 0.11 mol) in THF (2.51), mCPBA (152 g, 0.44 mol, 50%) was added and stirred at RT for 12 h. The solid was filtered, and washed with THF to give 4-(1-oxido-3-pyridinyl)benzoic acid (20 g, 86%).

$^1$H NMR (300 MHz, DMSO); 7.5–7.8 (m, 5H), 7.9 (d, J=8 Hz, 2H), 8.33 (d, J=5 Hz, 2H).

Similarly, starting from 4-tolylboronic acid (45 g, 0.33 mol) and 2-bromopyridine (52 g, 0.33 mol), the related intermediate 4-(1-oxido-2-pyridinyl)benzoic acid was obtained.

Example 1

General procedure for the solution-phase synthesis of pyrrolidine oxadiazole derivatives of general formula I, with B=IIa (Schemes 1,11): (3EZ,5S)-1-([1,1'-biphenyl]-4-ylcarbonyl)-5-(3-methyl-1,2,4-oxadiazol-5-yl)-3-pyrrolidinone O-methyloxime; (3E,5S)-1-[(2'-methyl[1,1'-biphenyl]-4-yl)carbonyl]-5-(3-methyl-1,2,4-oxadiazol-5-yl)-3-pyrrolidinone O-methyloxime and (3Z,5S)-1-[(2'-methyl[1,1'-biphenyl]-4-yl)carbonyl]-5-(3-methyl-1,2,4-oxadiazol-5-yl)-3-pyrrolidinone O-methyloxime

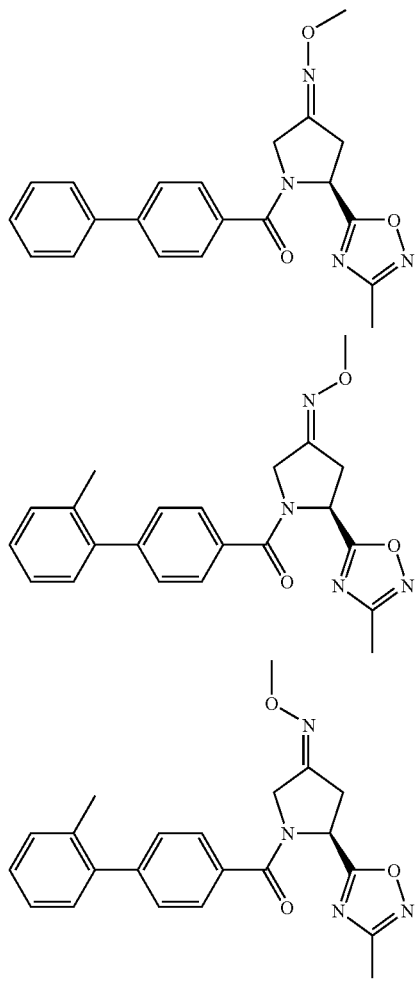

a) Protocol for the Formation of the Oxadiazole Ring

Diisopropylcarbodiimide (3.16 g, 25.17 mmol) was added to a solution of (2S,4EZ)-1-(tert-butoxycarbonyl)-4-(methoxyimino)-2-pyrrolidine-carboxylic acid (Intermediate 2, 6.50 g, 25.17 mmol) and acetamidoxime (Intermediate 7, 1.86 g, 25.17 mmol) in DCM (55 ml) and stirred overnight at room temperature (DCM-insoluble amidoximes were pre-dissolved in THF, to which was added a solution of DIC and Intermediate 2 in DCM). After filtering at the pump, and evaporation in vacuo, the residue was dissolved in pyridine (60 ml) and refluxed for one hour, then cooled and allowed to stand overnight, then evaporated in vacuo. The crude product was then dissolved in DCM (50 ml) and washed with sat. NaHCO$_3$(aq) (2×50 ml) and then 1M HCl(aq) (2×50 ml), dried over magnesium sulphate and evaporated in vacuo (crude yield 70%). Silica gel chromatography, eluting with 15% ethyl acetate in hexanes gave the desired compound, tert-butyl (2S,4EZ)-4-(methoxyimino)-2-(3-methyl-1,2,4-oxadiazol-5-yl)-1-pyrrolidinecarboxylate (4.4 g, 60% yield).

$^1$H NMR (360 MHz, DMSO); 1.3–1.6 (d, 9H), 2.4 (s, 3H), 2.8–3.4 (m, 2H), 3.9 (s, 3H), 4.3 (s, 2H), 5.2–5.4 (m, 1H).

b) Protocol for the N-deprotection Step

A solution was made containing tert-butyl (2S,4EZ)-4-(methoxyimino)-2-(3-methyl-1,2,4-oxadiazol-5-yl)-1-pyrrolidinecarboxylate (1.26 g, 4.25 mmol) in anhydrous DCM (120 ml). At 0° C., HCl gas, previously dried with a H$_2$SO$_4$ cc trap, was bubbled slowly through the reaction and deprotection was monitored by TLC using cyclohexane/ethyl acetate (1/1) and stained with a pancaldi solution. After approximately 45 minutes, TLC showed no remaining starting materiel and DCM was then evaporated under vacuo without heating to avoid pyrolidine salt decomposition. More DCM (20 ml) was then added and evaporated again under vacuo to remove remaining potential HCl (2–3 times). The desired product, (3EZ,5S)-5-(3-methyl-1,2,4-oxadiazol-5-yl)-3-pyrrolidinone O-methyloxime, hydrochloride salt, was isolated as a white solid and used without further purification and characterization c) Protocols for the N-capping Step Method A: To a solution of (3EZ,5S)-5-(3-methyl-1,2,4-oxadiazol-5-yl)-3-pyrrolidinone O-methyloxime, hydrochloride salt (200 mg, 0.86 mmol) in DCM (5 ml) was added [1,1'-biphenyl]-4-carbonyl chloride (205 mg, 0.95 mmol) followed by diisopropylethylamine (314 μl, 1.81 mmol) and stirred overnight at room temperature. Aminomethyl polystyrene resin (250 mg) was added to the reaction mixture and stirred for one hour before filtering at the pump. The solution was washed with citric acid(aq) (2×5 ml) and then dried over MgSO$_4$, and evaporated in vacuo. The product, (3EZ,5S)-1-([1,1'-biphenyl]-4-ylcarbonyl)-5-(3-methyl-1,2,4-oxadiazol-5-yl)-3-pyrrolidinone O-methyloxime, was purified by silica gel chromatography, eluting with 20% ethylacetate in hexanes (60 mg, 19% yield)

Method B: A solution was made containing (3EZ,5S)-5-(3-methyl-1,2,4-oxadiazol-5-yl)-3-pyrrolidinone O-methyloxime, hydrochloride salt, 2'-methyl[1,1'-biphenyl]-4-carboxylic acid (0.857 g, 4.04 mmol, 0.95 eq) and, optionally, DMAP (1.03 g, 8.50 mmol. 2.0 eq) in dry DCM (120 ml). The reaction was stirred at RT for 10 minutes before being cooled down to 0° C. At 0° C., EDC, HCl (815 mg, 4.25 mmol) was slowly added portion wise over a 30 minute period. The reaction mixture was stirred at 0° C. for 2 hours and gently warmed to RT overnight. Once the reaction was completed, the organic phase was washed twice with citric acid (10%) and sodium carbonate (10%). The organic phase was dried and evaporated. The crude product was purified and separated into the (E)- and (Z)-isomers by column chromatography (Biotage system, column 40M, 90 g SiO2, using cyclohexane/ethyl acetate (1/1) as eluent affording (3E,5S)-1-[(2'-methyl[1,1'-biphenyl]-4-yl)carbonyl]-5-(3-methyl-1,2,4-oxadiazol-5-yl)-3-pyrrolidinone O-methyloxime (770 mg, 34%) colorless oil, 97.5% purity by HPLC) and (3Z,5S)-1-[(2'-methyl[1,1'-biphenyl]-4-yl)carbonyl]-5-(3-methyl-1,2,4-oxadiazol-5-yl)-3-pyrrolidinone O-methyloxime (740 mg, 33%), colorless oil, 98.3% purity by HPLC).

(3E,5S)-1-[(2'-methyl[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.28 (s, 3H, ArCH$_3$), 2.42 (s, 3H, CH$_3$), 3.03–3.32 (m, 2H), 3.88 (s, 3H, NOCH$_3$), 4.38–4.59 (m, 2H), 6.03 (m, 1H), 7.22–7.29 (m, 5H, H arom.), 7.40–7.44 (m, 2H, H arom.), 7.55 (m, 1H); MS(APCI$^+$): 391.5; MS(APCI$^-$): 389.2.

(3Z,5S)-1-[(2'-methyl[1,1'-biphenyl]-4-yl)carbonyl]-5-(3-methyl-1,2,4-oxadiazol-5-yl)-3-pyrrolidinone O-methyloxime: white solid, m.p. 146.5° C.; IR (neat) ν 2936, 1645, 1583, 1408, 1323, 1047, 890 cm$^{-1}$; $^1$H NMR (300 MHz, CDCl$_3$): 2.28 (s, 3H, ArCH$_3$), 2.42 (s, 3H, CH$_3$), 3.03–3.32 (m, 2H), 3.88 (s, 3H, NOCH$_3$), 4.38–4.59 (m, 2H), 6.03 (m, 1H), 7.22–7.29 (m, 5H, H arom.), 7.40–7.44 (m, 2H, H arom.), 7.55 (m, 1H); MS(APCI$^+$): 391.5; MS(APCI$^-$): 389.2

Example 2

(3EZ,5S)-1-[(2'-chloro[1,1'-biphenyl]-4-yl)carbonyl]-5-(3-methyl-1,2,4-oxadiazol-5-yl)-3-pyrrolidinone O-methyloxime

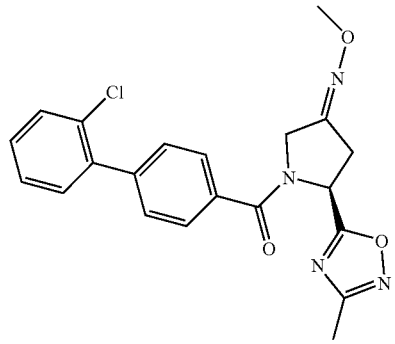

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 2'-chloro[1,1'-biphenyl]-4-carboxylic acid (Intermediate 10), the title compound was isolated, after flash-chromatography, as a mixture of E-/Z-isomers as an oil in 31% yield (98.5% purity by HPLC).

Oil; $^1$H NMR (300 MHz, CDCl$_3$): 2.41 (s, 3H, CH$_3$), 2.96–3.31 (m, 2H, CH$_2$), 3.87 (s, 3H, NOCH$_3$), 4.31–4.59 (m, 2H, CH$_2$), 6.03 (m, 1H), 7.30 (s, 3H, H arom.), 7.50–7.64 (m, 5H, H arom.); MS(ESI$^+$): 411.2; MS(ESI$^-$): 408.9.

Example 3

(3EZ,5S)-5-(3-methyl-1,2,4-oxadiazol-5-yl)-1-{[2'-(trifluoromethyl)[1,1'-biphenyl]-4-yl]carbonyl}-3-pyrrolidinone O-methyloxime

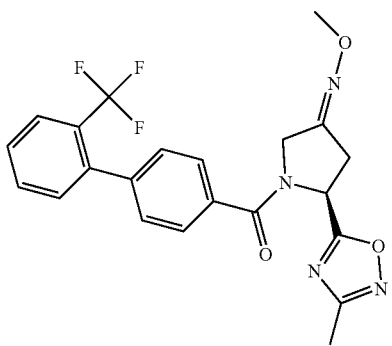

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 2'-(trifluoromethyl) [1,1'-biphenyl]-4-carboxylic acid (Intermediate 10), the title compound was isolated, after flash-chromatography, as a mixture of E-/Z-isomers as an oil in 44% yield (88.2% purity by HPLC).

Oil; $^1$H NMR (300 MHz, CDCl$_3$): 2.40 (s, 3H, CH$_3$), 2.88–3.31 (m, 2H, CH$_2$), 3.87 (s, 3H, NOCH$_3$), 4.27–4.53 (m, 2H, CH$_2$), 6.03 (m, 1H), 7.27–7.70 (m, 7H, H arom.), 7.77 (m, 1H, H arom.); MS(ESI$^+$): 445.4; MS(ESI$^-$): 443.1.

Example 4

(3E,5S)-1-[(2'-fluoro[1,1'-biphenyl]-4-yl)carbonyl]-5-(3-methyl-1,2,4-oxadiazol-5-yl)-3-pyrrolidinone O-methyloxime and (3Z,5S)-1-[(2'-fluoro[1,1'-biphenyl]-4-yl)carbonyl]-5-(3-methyl-1,2,4-oxadiazol-5-yl)-3-pyrrolidinone O-methyloxime

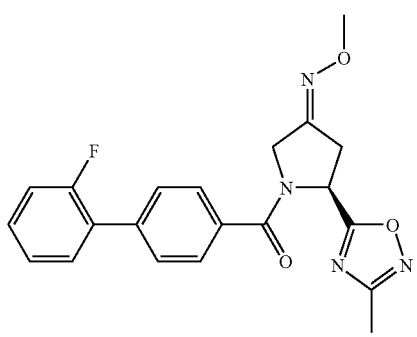

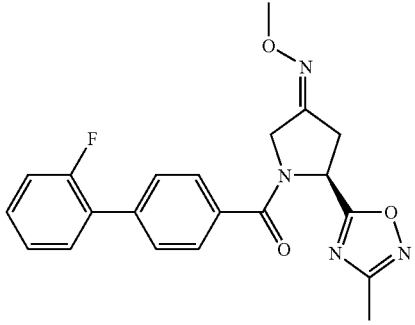

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 2'-fluoro[1,1'-biphenyl]-4-carboxylic acid (Intermediate 10), the title compounds were obtained as a mixture of E-/Z-isomers and subsequently separated by flash-chromatography, to afford (3E,5S)-1-[(2'-fluoro[1,1'-biphenyl]-4-yl)carbonyl]-5-(3-methyl-1,2,4-oxadiazol-5-yl)-3-pyrrolidinone O-methyloxime in 11% yield (95.0% purity by HPLC) and (3Z,5S)-1-[(2'-fluoro[1,1'-biphenyl]-4-yl)carbonyl]-5-(3-methyl-1,2,4-oxadiazol-5-yl)-3-pyrrolidinone O-methyloxime in 11% yield (98.2% purity by HPLC).

(3E,5S)-1-[(2'-fluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.42 (s, 3H, CH$_3$), 3.07–3.25 (m, 2H, CH$_2$), 3.87 (s, 3H, NOCH$_3$), 4.42–4.52 (m, 2H, CH$_2$), 6.04 (m, 1H), 7.15–7.29 (m, 2H, H arom.), 7.30–7.44 (m, 2H, H arom.), 7.70 (m, 4H); MS(ESI$^+$): 395.0; MS(ESI$^-$): 393.0.

(3Z,5S)-1-[(2'-fluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.42 (s, 3H, CH$_3$), 3.02 (m, 1H, CH), 3.25 (m, 1H, CH), 3.87 (s, 3H, NOCH$_3$), 4.34–4.58 (m, 2H, CH$_2$), 6.04 (m, 1H), 7.15–7.29 (m, 2H, H arom.), 7.30–7.44 (m, 2H, H arom.), 7.70 (m, 4H); MS(ESI$^+$): 395.0; MS(ESI$^-$): 393.0.

Example 5

(3EZ,5S)-1-[(4'-fluoro[1,1'-biphenyl]-4-yl)carbonyl]-5-(3-methyl-1,2,4-oxadiazol-5-yl)-3-pyrrolidinone O-methyloxime

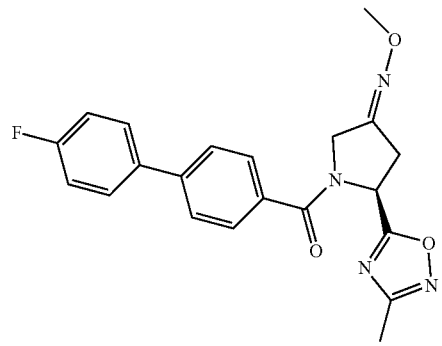

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 4'-fluoro[1,1'-biphenyl]-4-carboxylic acid (Intermediate 10), the title compound was isolated, after flash-chromatography, as a mixture of E-/Z-isomers as an oil in 32% yield (94.1% purity by HPLC).

Oil; $^1$H NMR (300 MHz, CDCl$_3$): 2.42 (s, 3H, CH$_3$), 2.95–3.30 (m, 2H, CH$_2$), 3.87 (s, 3H, NOCH$_3$), 4.27–4.55 (m, 2H, CH$_2$), 6.02 (m, 1H), 7.12 (m, 2H, H arom.), 7.27–7.61 (m, 6H, H arom.); MS(ESI$^+$): 395.5; MS(ESI$^-$): 393.4.

Example 6

(3EZ,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime; (3Z,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime

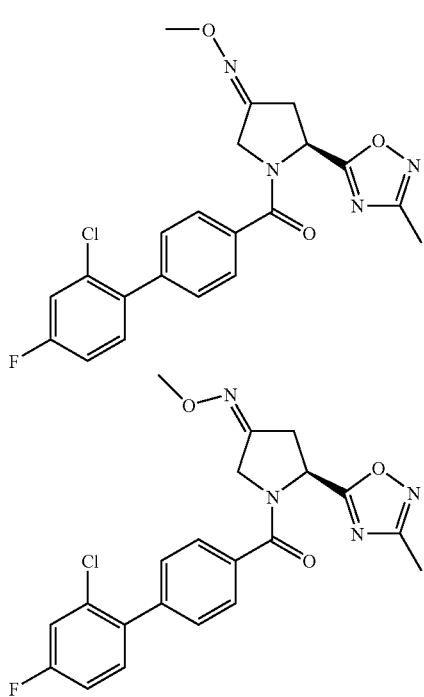

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 2'-chloro-4'-fluoro [1,1'-biphenyl]-4-carboxylic acid (Intermediate 10), the title compound was isolated, after flash-chromatography, as a mixture of E-/Z-isomers as an oil in 60% overall yield (95.20% purity by HPLC). Subsequent flash-chromatography afforded (3Z,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime in 30% yield (97.5% purity by HPLC).

(3EZ,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.31 (s, 3H, CH$_3$), 2.78–3.24 (m, 2H, CH$_2$), 3.77 (s, 3H, NOCH$_3$), 4.30–4.52 (m, 2H, CH$_2$); 5.93 (m, 1H), 6.88–7.60 (m, 7H, H arom.); MS(ESI$^+$): 429.20.

(3Z,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.31 (s, 3H, CH$_3$), 2.78–3.24 (m, 2H, CH$_2$), 3.77 (s, 3H, NOCH$_3$), 4.30–4.52 (m, 2H, CH$_2$), 5.93 (m, 1H), 6.88–7.60 (m, 7H, H arom.); MS(ES): 429.20.

Example 7

(3EZ,5S)-1-[(2',4'-difluoro[1,1'-biphenyl]-4-yl)carbonyl]-5-(3-methyl-1,2,4-oxadiazol-5-yl)-3-pyrrolidinone O-methyloxime; (3Z,5S)-1-[(2',4'-difluoro[1,1'-biphenyl]-4-yl)carbonyl]-5-(3-methyl-1,2,4-oxadiazol-5-yl)-3-pyrrolidinone O-methyloxime; (3E,5S)-1-[(2',4'-difluoro[1,1'-biphenyl]-4-yl)carbonyl]-5-(3-methyl-1,2,4-oxadiazol-5-yl)-3-pyrrolidinone O-methyloxime

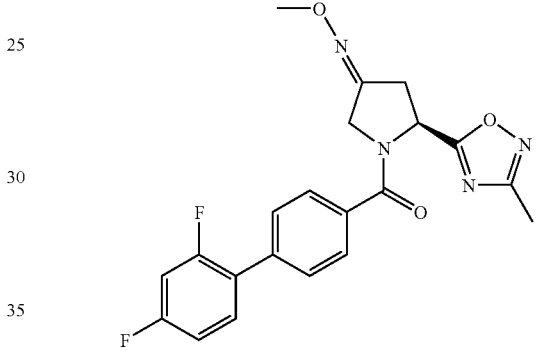

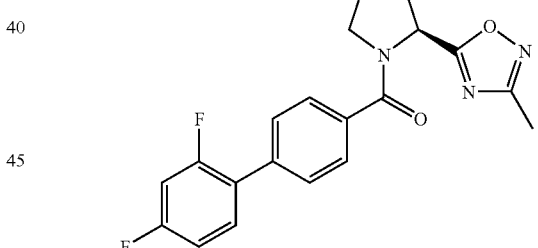

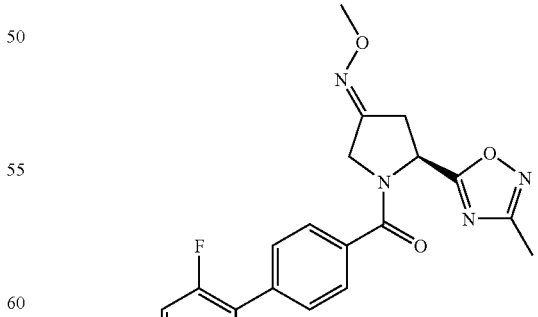

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 2',4'-difluoro [1,1'-biphenyl]-4-carboxylic acid (Intermediate 10), the title compound was isolated, after flash-chromatography, as a mixture of E-/Z-isomers as an oil in a 37% overall yield (98.6% purity by HPLC). Subsequent flash-chromatographic separation of E- and Z-isomers afforded (3Z,5S)-1-[(2',4'-difluoro[1,1'-biphenyl]-4-yl)carbonyl]-5-(3-methyl-1,2,4-oxadiazol-5-yl)-3-pyrrolidinone O-methyloxime in 15% yield (98.5% purity by HPLC), and (3E,5S)-1-[(2',4'-difluoro[1,1'-biphenyl]-4-yl)carbonyl]-5-(3-methyl-1,2,4-oxadiazol-5-yl)-3-pyrrolidinone O-methyloxime in 13% yield (97.5% purity by HPLC).

(3EZ,5S)-1-[(2',4'-difluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.34 (s, 3H, CH$_3$), 2.86–3.25 (m, 2H, CH$_2$), 3.79 (s, 3H, NOCH$_3$), 4.30–4.52 (m, 2H, CH$_2$), 5.96 (m, 1H), 6.82–7.01 (m, 2H, H arom), 7.32–7.66 (m, 5H, H arom); MS(ESI$^+$): 413.40; MS(ESI$^-$): 411.20.

(3Z,5S)-1-[(2',4'-difluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.31 (s, 3H, CH$_3$), 2.78–3.24 (m, 2H, CH$_2$), 3.77 (s, 3H, NOCH$_3$), 4.30–4.52 (m, 2H, CH$_2$), 5.93 (m, 1H), 6.88–7.60 (m, 7H, H arom.); MS(ESI$^+$): 413.40; MS(ESI$^-$): 411.20.

(3E,5S)-1-[(2',4'-difluoro[1,1'-biphenyl]-4-yl)carbonyl]-5-(3-methyl-1,2,4-oxadiazol-5-yl)-3-pyrrolidinone O-methyloxime: oil; $^1$H NMR (300 MHz, CDCl$_3$): 2.31 (s, 3H, CH$_3$), 2.78–3.24 (m, 2H, CH$_2$), 3.77 (s, 3H, NOCH$_3$), 4.30–4.52 (m, 2H, CH$_2$), 5.93 (m, 1H), 6.88–7.60 (m, 7H, H arom.); MS(ESI$^+$): 413.40; MS(ESI$^-$): 411.20.

Example 8

(3EZ,5S)-1-[(4'-fluoro-2'-methyl[1,1'-biphenyl]-4-yl)carbonyl]-5-(3-methyl-1,2,4-oxadiazol-5-yl)-3-pyrrolidinone O-methyloxime

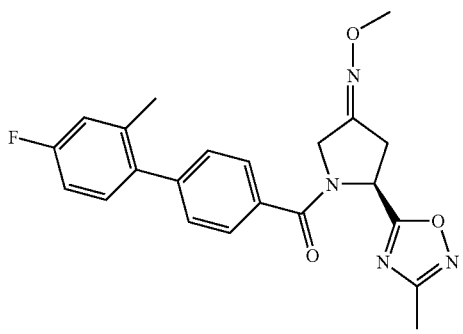

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N'-hydroxyethanimidamide (Intermediate 7) and 4'-fluoro-2'-methyl[1,1'-biphenyl]-4-carboxylic acid (Intermediate 10), the title compound was isolated, after flash-chromatography, as a mixture of E-/Z-isomers as an oil in a 14% overall yield (95.2% purity by HPLC).

Oil; $^1$H NMR (300 MHz, CDCl$_3$): 2.17 (s, 3H, CH$_3$), 2.34 (s, 3H, CH$_3$), 2.86–3.26 (m, 2H, CH$_2$), 3.80 (s, 3H, NOCH$_3$), 4.33–4.45 (m, 2H, CH$_2$), 5.97 (m, 1H), 6.82–6.95 (m, 2H, H arom), 7.10–7.66 (m, 5H, H arom); MS(ESI$^+$): 409.33; MS(ESI$^-$): 407.11.

Example 9

(3E,5S)-1-([1,1'-biphenyl]-4-ylcarbonyl)-5-[3-(2-hydroxyethyl)-1,2,4-oxadiazol-5-yl]-3-pyrrolidinone O-methyloxime; (3Z,5S)-1-([1,1'-biphenyl]-4-ylcarbonyl)-5-[3-(2-hydroxyethyl)-1,2,4-oxadiazol-5-yl]-3-pyrrolidinone O-methyloxime

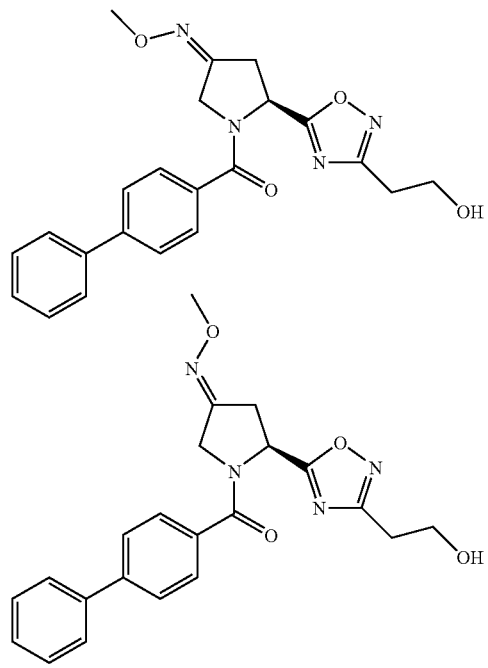

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N',3-dihydroxypropanimidamide (Intermediate 7) and [1,1'-biphenyl]-4-carboxylic acid (Intermediate 10), the title compound was isolated, after flash-chromatography, as a mixture of E-/Z-isomers as an oil in 64% overall yield (90% purity by HPLC). At this stage, a scavenging purification using pol-trisamine in DCM (Novabiochem) was carried out to remove excess acid by-products which turned out to be difficult to remove by flash chromatography column. The E- and Z-isomers were finally deparated by flash column chromatography (Biotage system, column 40M, 90 g SiO$_2$, using cyclohexane/ethyl acetate (2/8) as eluent, affording (3E,5S)-1-([1,1'-biphenyl]-4-ylcarbonyl)-5-[3-(2-hydroxyethyl)-1,2,4-oxadiazol-5-yl]-3-pyrrolidinone O-methyloxime in 25% yield (98.0% purity by HPLC), and (3Z,5S)-1-([1,1'-biphenyl]-4-ylcarbonyl)-5-[3-(2-hydroxyethyl)-1,2,4-oxadiazol-5-yl]-3-pyrrolidinone O-methyloxime in 25% yield (99.5% purity by HPLC).

(3E,5S)-1-([1,1'-biphenyl]-4-ylcarbonyl)-5-[3-(2-hydroxyethyl)-1,2,4-oxadiazol-5-yl]-3-pyrrolidinone O-methyloxime: white solid, mp. 140.5° C.; $^1$H NMR (300 MHz, CDCl$_3$): 2.98–3.05 (m, 3H, CH$_2$), 3.33 (m, 1H, CH$_2$), 3.86 (s, 3H, OCH$_3$), 4.35–4.57 (m, 2H, CH$_2$), 6.04 (m, 1H, CH), 7.38–7.51 (m, 3H, H$_{Ar'}$), 7.51–7.61 (m, 6H, H$_{Ar'}$); M$^+$(ESI$^+$): 407.31; M(ESI$^-$): 405.13.

(3Z,5S)-1-([1,1'-biphenyl]-4-ylcarbonyl)-5-[3-(2-hydroxyethyl)-1,2,4-oxadiazol-5-yl]-3-pyrrolidinone O-methyloxime: white solid, m.p. 141° C.; $^1$H NMR (300 MHz, CDCl$_3$): 2.98–3.05 (m, 3H, CH$_2$), 3.33 (m, 1H, CH$_2$), 3.86 (s, 3H, OCH$_3$), 4.35–4.57 (m, 2H, CH$_2$), 6.04 (m, 1H, CH), 7.38–7.51 (m, 3H, H$_{Ar'}$), 7.51–7.61 (m, 6H, H$_{Ar'}$); M$^+$(ESI$^+$): 407.31; M(ESI$^-$): 405.13.

Example 10

2-{5-[(2S,4EZ)-1-([1,1'-biphenyl]-4-ylcarbonyl)-4-(methoxyimino)pyrrolidinyl]-1,2,4-oxadiazol-3-yl}ethyl[(tert-butoxycarbonyl)amino]acetate; 2-{5-[(2S,4EZ)-1-([1,1'-biphenyl]-4-ylcarbonyl)-4-(methoxyimino)pyrrolidinyl]-1,2,4-oxadiazol-3-yl}ethyl aminoacetate

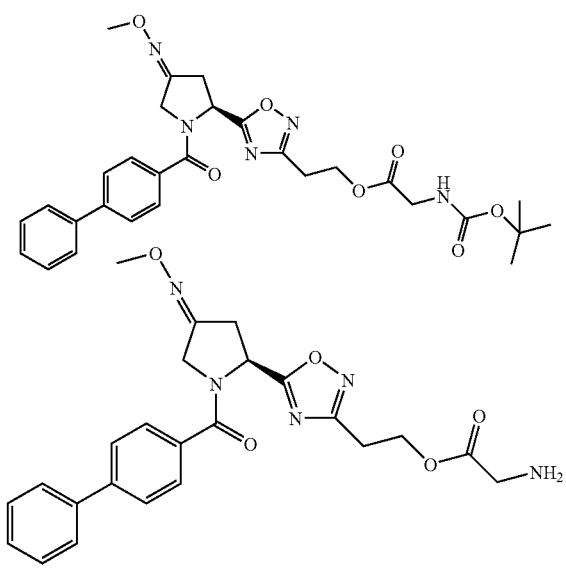

EDC (290 mg, 1.51 mmol) was added portion-wise (over 15 minutes) to a stirred solution of (3Z,5S)-1-([1,1'-biphenyl]-4-ylcarbonyl)-5-[3-(2-hydroxyethyl)-1,2,4-oxadiazol-5-yl]-3-pyrrolidinone O-methyloxime (1.59 mmol, Example 9), dimethylamino pyridine (185 mg, 1.51 mmol), and [(tert-butoxycarbonyl)amino]acetic acid (264 mg, 1.51 mmol) in DCM (50 ml) at 0° C. After stirring for 1 hour at 0° C., the reaction mixture was allowed to warm to room temperature. The reaction was monitored by TLC and LC/MS. After a further hour stirring at RT, the reaction mixture was hydrolyzed with water, washed with citric acid 10% (2×10 ml) then Na$_2$CO$_3$ (aq) (2×10 ml), dried over MgSO$_4$ and evaporated in vacuo to give the crude product. Silica gel chromatography, eluting with 40% EtOAc in cyclohexane gave the desired compound, (2-{5-[(2S,4EZ)-1-([1,1'-biphenyl]-4-ylcarbonyl)-4-(methoxyimino)pyrrolidinyl]-1,2,4-oxadiazol-3-yl}ethyl[(tert-butoxycarbonyl)amino]acetate) as a mixture of E- and Z-isomers in 90% yield (purity by HPLC: 93.6%).

M$^+$(ESI$^+$): 564.61; M(ESI$^-$): 562.60

(2-{5-[(2S,4EZ)-1-([1,1'-biphenyl]-4-ylcarbonyl)-4-(methoxyimino)pyrrolidinyl]-1,2,4-oxadiazol-3-yl}ethyl[(tert-butoxycarbonyl)amino]acetate) (100 mg, 0.178 mmol) was treated with a 25% TFA/DCM solution at 0° C. for 1 hour. The reaction was then slowly made basic at 0° C. with sodium carbonate solution (10%) and extracted with DCM. The organic phases were combined and dried over magnesium sulfate and solvent removal afforded the desired compound, 2-{5-[(2S,4EZ)-1-([1,1'-biphenyl]-4-ylcarbonyl)-4-(methoxyimino)pyrrolidinyl]-1,2,4-oxadiazol-3-yl}ethyl aminoacetate, as an oil in a 70% yield (94.6% purity by HPLC).

M$^+$(ESI$^+$): 464.17; M(ESI$^-$): 462.86

Example 11

(3EZ,5S)-1-[(2'-chloro-4'-fluoro[1,1'-biphenyl]-4-yl)carbonyl]-5-[3-(2-hydroxyethyl)-1,2,4-oxadiazol-5-yl]-3-pyrrolidinone O-methyloxime

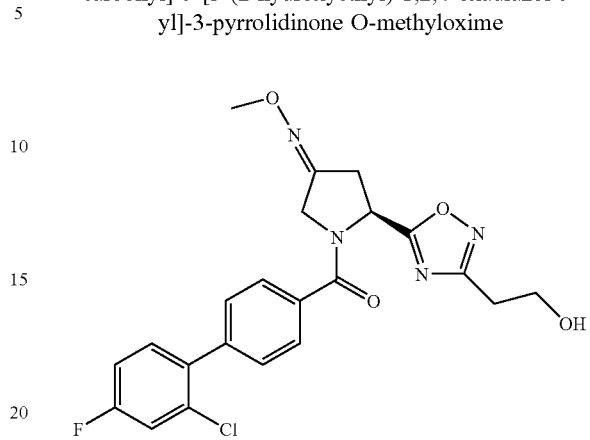

Following the general methods as outlined in Example 1 (Method B), starting from (2S,4EZ)-1-(tert-butoxycarbonyl)-4-(methoxyimino)-2-pyrrolidine-carboxylic acid (Intermediate 2), N',3-dihydroxypropanidamide (Intermediate 7) and 2'-chloro-4'-fluoro[1,1'-biphenyl]-4-carboxylic acid (Intermediate 10), the title compound was isolated, after flash-chromatography, as a mixture of E-/Z-isomers as an oil in 8% overall yield (78.7% purity by HPLC).

Oil; $^1$H NMR (300 MHz, CDCl$_3$): 2.93 (m, 2H, CH$_2$), 3.10–3.25 (m, 2H, CH$_2$), 3.80 (s, 3H, NOCH$_3$), 4.34–4.45 (m, 2H, CH$_2$), 5.98 (m, 1H), 6.90–7.05 (m, 2H, H arom), 7.20–7.66 (m, 5H, H arom); MS(ESI$^+$): 459.12; MS(ESI$^-$): 457.07.

Example 12 tert-butyl 4-{5-[(2S,4EZ)-1-([1,1'-biphenyl]-4-ylcarbonyl)-4-(methoxyimino)pyrrolidinyl]-1,2,4-oxadiazol-3-yl}-1-piperidinecarboxylate; (3EZ,5S)-1-([1,1'-biphenyl]-4-ylcarbonyl)-5-[3-(4-piperidinyl)-1,2,4-oxadiazol-5-yl]-3-pyrrolidinone O-methyloxime

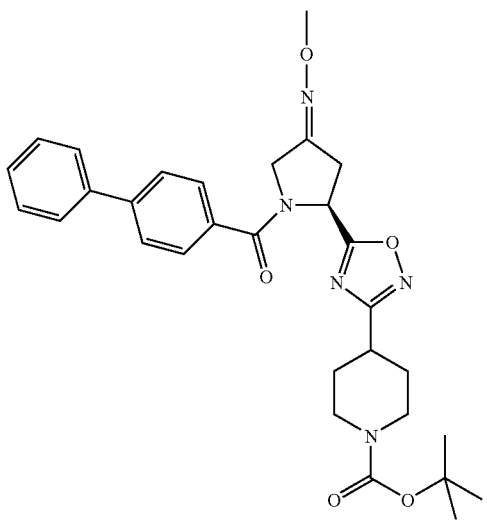

-continued

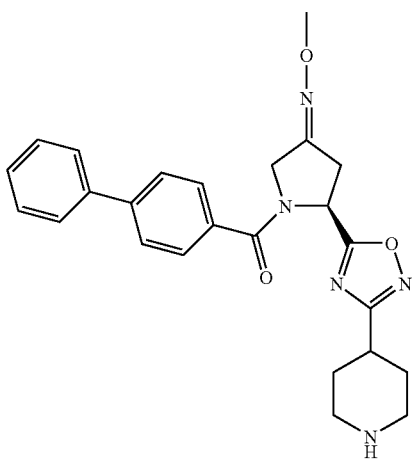

Following the general methods as outlined in Example 1 (Method A), starting from (2S,4EZ)-1-(tert-butoxycarbonyl)-4-(methoxyimino)-2-pyrrolidine-carboxylic acid (intermediate 2), tert-butyl 4-[amino(hydroxyimino)methyl]-1-piperidinecarboxylate (Intermediate 7) and [1,1'-biphenyl]-4-carbonyl chloride, the desired compound, tert-butyl 4-{5-[(2S,4EZ)-1-([1,1'-biphenyl]-4-ylcarbonyl)-4-(methoxyimino)pyrrolidinyl]-1,2,4-oxadiazol-3-yl}-1-piperidinecarboxylate, was isolated, after flash-chromatography (cyclohexane/ethylacetate 6/4), as a mixture of E-/Z-isomers in 60% yield (97.9% purity by HPLC).

Oil; $^1$H NMR (300 MHz, CDCl$_3$): 1.47 (s, 9H, CH$_3$), 1.60–2.10 (m, 4H, CH$_2$), 2.90–3.02 (m, 2H, CH$_2$), 3.30–3.40 (m, 1H, CH), 3.86 (s, 3H, NOCH$_3$), 4.01–4.55 (m, 6H, CH$_2$N), 6.03 (m, 1H), 7.48–7.64 (m, 9H, H arom.); MS(ESI$^+$): 546.4; MS(ESI$^-$): 544.2.

tert-butyl 4-{5-[(2S,4EZ)-1-([1,1'-biphenyl]-4-ylcarbonyl)-4-(methoxyimino)pyrrolidinyl]-1,2,4-oxadiazol-3-yl}-1-piperidinecarboxylate) (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded a residue which was purified by flash-chromatography using cyclohexane/ethylacetate (2/8) as eluent to give (3EZ,5S)-1-([1,1'-biphenyl]-4-ylcarbonyl)-5-[3-(4-piperidinyl)-1,2,4-oxadiazol-5-yl]-3-pyrrolidinone O-methyloxime as a mixture of E-/Z-isomers in 80% yield (96.1% purity by HPLC).

Oil; $^1$H NMR (300 MHz, CDCl$_3$): 1.80–2.20 (m, 4H, CH$_2$), 2.90–3.50 (m, 8H, CH$_2$), 3.87 (s, 3H, NOCH$_3$), 4.30–4.60 (m, 2H, CH$_2$), 6.04 (m, 1H, CH), 7.48–7.64 (m, 9H, H arom.); MS(ESI$^+$): 446.4.

Example 13

(3EZ,5S)-5-[3-(1-acetyl-4-piperidinyl)-1,2,4-oxadiazol-5-yl]-1-([1,1'-biphenyl]-4-ylcarbonyl)-3-pyrrolidinone O-methyloxime

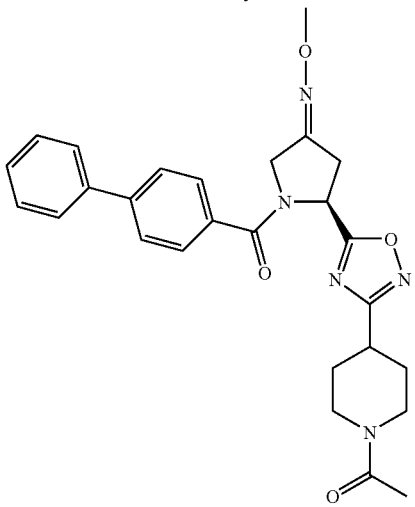

(3EZ,5S)-1-([1,1'-biphenyl]-4-ylcarbonyl)-5-[3-(4-piperidinyl)-1,2,4-oxadiazol-5-yl]-3-pyrrolidinone O-methyloxime (Example 12) was dissolved in dry DCM at 0° C. in presence of 1.5 equivalent of triethyl amine and treated with 1 equivalent of acetyl chloride. The reaction mixture was stirred at this temperature for 30 minutes and then hydrolyzed with ice. The reaction was then made basic with a sodium carbonate solution (10%) and extracted with DCM. It was then dried with magnesium sulfate and solvent removal afforded a residue which was purified by flash-chromatography using cyclohexane/ethylacetate (1/1) as eluent to give (3EZ,5S)-5-[3-(1-acetyl-4-piperidinyl)-1,2,4-oxadiazol-5-yl]-1-([1,1'-biphenyl]-4-ylcarbonyl)-3-pyrrolidinone O-methyloxime as a mixture of E-/Z-isomers in 95% yield (100% purity by HPLC).

Oil; $^1$H NMR (300 MHz, CDCl$_3$): 1.70–2.20 (m, 8H, CH$_3$CO, CH$_2$), 2.89–3.40 (m, 6H, CH$_2$), 3.88 (s, 3H, NOCH$_3$), 4.40–4.60 (m, 2H, CH$_2$), 6.04 (m, 1H, CH), 7.48–7.64 (m, 9H), H arom.); MS(ESI$^+$): 488.37; MS(ESI$^-$): 486.17.

Example 14

(3EZ,5S)-1-([1,1'-biphenyl]-4-ylcarbonyl)-5-[3-(1-methyl-4-piperidinyl)-1,2,4-oxadiazol-5-yl]-3-pyrrolidinone O-methyloxime

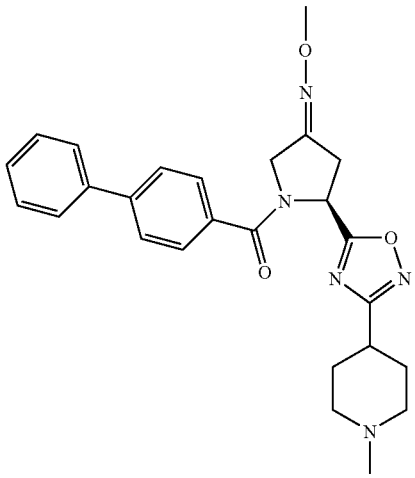

(3EZ,5S)-1-([1,1'-biphenyl]-4-ylcarbonyl)-5-[3-(4-piperidinyl)-1,2,4-oxadiazol-5-yl]-3-pyrrolidinone O-methyloxime (Example 12) was dissolved in dry DCM at 0° C. in presence of 1.5 equivalent of triethyl amine and treated with 1 equivalent of methyl iodide. The reaction mixture was stirred at room temperature for 12 hours. The reaction was hydrolysed and then made basic with a sodium carbonate solution (10%) and extracted with DCM. It was then dried with magnesium sulfate and solvent removal afforded a residue, which was purified by flash-chromatography using dichloromethane/methanol (98/2) as eluent to give (3EZ,5S)-1-([1,1'-biphenyl]-4-ylcarbonyl)-5-[3-(1-methyl-4-piperidinyl)-1,2,4-oxadiazol-5-yl]-3-pyrrolidinone O-methyloxime as a mixture of E-/Z-isomers in 50% yield (96.8% purity by HPLC).

Oil; $^1$H NMR (300 MHz, CDCl$_3$): 1.19 (m, 2H, CH$_2$), 2.14–2.70 (m, 8H, CH$_3$, CH$_2$), 2.89–3.25 (m, 4H, CH$_2$), 3.80 (s, 3H, NOCH$_3$), 4.20–4.55 (m, 2H, CH$_2$), 5.94 (m, 1H, CH), 7.33–7.58 (m, 9H, H arom.); MS(ESI$^+$): 460.43; MS(ESI$^-$): 458.24.

Example 15

General procedure for the solution-phase synthesis of pyrrolidine oxadiazole derivatives of general formula I, with B being a substituent of formula IIb (see Schemes 7,11): (3EZ,5S)-1-([1,1'-biphenyl]-4-ylcarbonyl)-5-[5-(phenoxymethyl)-1,2,4-oxadiazol-3-yl]-3-pyrrolidinone O-methyloxime

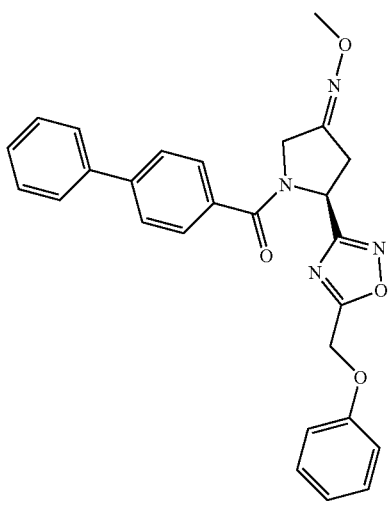

To a suspension of (2S,4EZ)-1-([1,1'-biphenyl]-4-ylcarbonyl)-N'-hydroxy-4-(methoxyimino)-2-pyrrolidinecarboximidamide (Intermediate 8, 100 mg, 0.28 mmol), DMAP (41 mg, 0.34 mmol), and phenoxyacetic acid (48 mg, 0.31 mmol) in DCM & DMF (1:1, 10 ml) was added EDC (59 mg, 0.31 mmol). After stirring overnight at ambient temperature, the solvent was evaporated in vacuo. The residue was dissolved in DCM (10 ml) and washed with citric acid(aq) (2×10 ml) followed by sodium bicarbonate(aq) (2×10 ml). After evaporating in vacuo, pyridine was added (15 ml) and the solution was refluxed overnight. The pyridine was removed in vacuo, and the residue was dissolved in DCM (10 ml), washed with citric acid(aq) (2×10 ml), dried over magnesium sulphate and evaporatedm, to afford the title compound in 80% purity by HPLC. MS(ESI$^+$): m/z=469.2.

Example 16

{3-[(2S,4EZ)-1-([1,1'-biphenyl]-4-ylcarbonyl)-4-(methoxyimino)pyrrolidinyl]-1,2,4-oxadiazol-5-yl}methylformamide

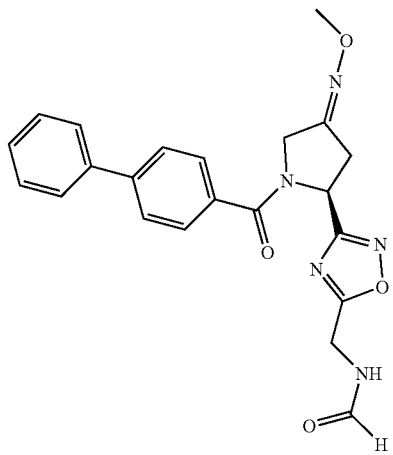

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (formylamino)acetic acid, the title compound was obtained in 72% purity by HPLC.

$^1$H-NMR (400 MHz, CDCl$_3$): 2.9–3.2 (m, 2H), 3.8 (m, 3H), 4.2–4.4 (m, 2H0, 4.6 (m, 2H), 5.9 (m, 1H), 7.0 (m, 1H), 7.3–7.7 (m, 9H), 8.2 (s, 1H). MS(ESI$^+$): m/z=420.1.

Example 17

(3EZ,5S)-1-([1,1'-biphenyl]-4-ylcarbonyl)-5-[5-(methoxymethyl)-1,2,4-oxadiazol-3-yl]-3-pyrrolidinone O-methyloxime

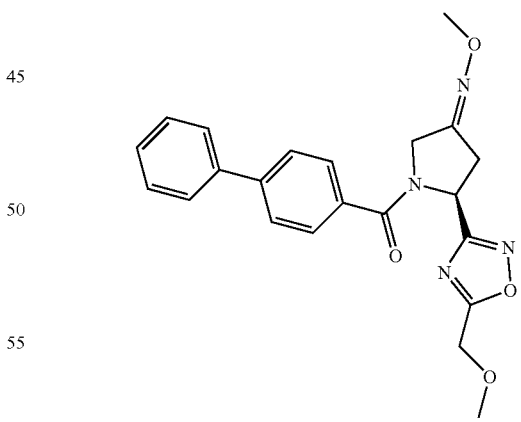

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and methoxyacetic acid, the title compound was obtained in 91% purity by HPLC.

$^1$H-NMR (400 MHz, CDCl$_3$): 2.9–3.2 (m, 2H), 3.4 (s, 3H), 3.75 (m, 3H), 4.2–4.5 (m, 2H), 4.6 (s, 2H), 6.0 (m, 1H0, 7.4–7.6 (m, 9H). MS(ESI$^+$): m/z=407.2.

Example 18

(3EZ,5S)-1-([1,1'-biphenyl]-4-ylcarbonyl)-5-(5-phenyl-1,2,4-oxadiazol-3-yl)-3-pyrrolidinone O-methyloxime

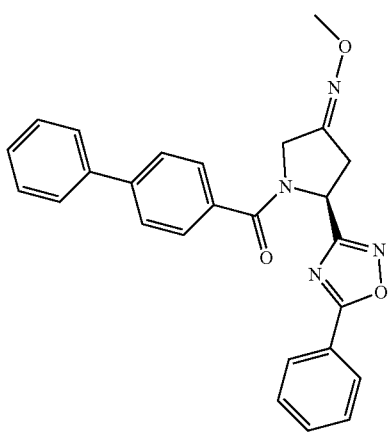

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and benzoic acid, the title compound was obtained in 85% purity by HPLC. MS(ESI$^+$): m/z=439.2.

Example 19

N-({3-[(2S,4EZ)-1-([1,1'-biphenyl]-4-ylcarbonyl)-4-(methoxyimino)pyrrolidinyl]-1,2,4-oxadiazol-5-yl}methyl)acetamide

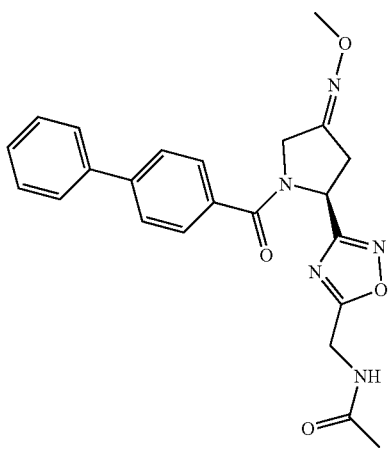

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (acetylamino)acetic acid, the title compound was obtained in 72% purity by HPLC. MS(ESI$^+$): m/z=434.2.

Example 20

(3EZ,5S)-1-([1,1'-biphenyl]-4-ylcarbonyl)-5-{5-[4-(hydroxymethyl)phenyl]-1,2,4-oxadiazol-3-yl}-3-pyrrolidinone O-methyloxime

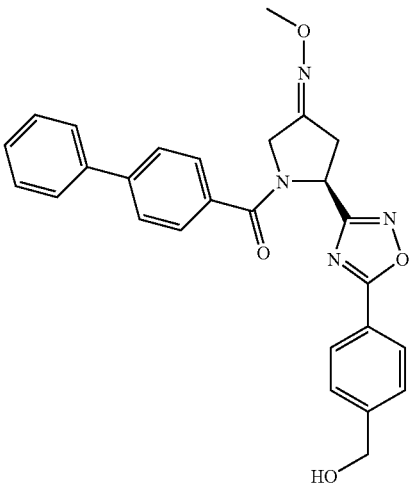

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 4-(hydroxymethyl)benzoic acid, the title compound was obtained in 54% purity by HPLC. MS(ESI$^+$): m/z=469.4.

Example 21

(3EZ,5S)-1-([1,1'-biphenyl]-4-ylcarbonyl)-5-[5-(2-hydroxyethyl)-1,2,4-oxadiazol-3-yl]-3-pyrrolidinone O-methyloxime

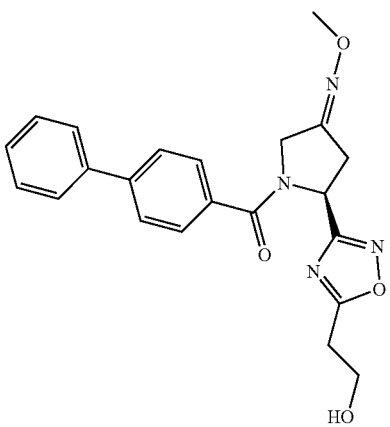

Following the general method as outlined in Example 15, starting from (2S,4EZ)-1-([1,1'-biphenyl]-4-ylcarbonyl)-N'-hydroxy(methoxyimino)-2-pyrrolidinecarboximidamide (Intermediate 8) and 3-hydroxypropanoic acid, the title compound was obtained in 61% purity by HPLC. MS(ESI$^+$): m/z=407.2.

Example 22

(3EZ,5S)-1-([1,1'-biphenyl]-4-ylcarbonyl)-5-{5-[(2S)-2-hydroxy-2-phenylethyl]-1,2,4-oxadiazol-3-yl}-3-pyrrolidinone O-methyloxime

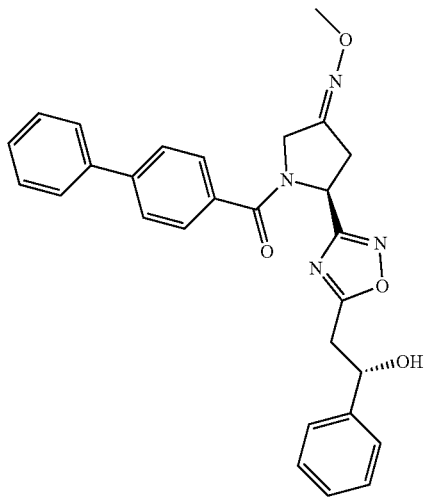

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (3S)-3-hydroxy-3-phenylpropanoic acid, the title compound was obtained in 89% purity by HPLC. MS(ESI$^+$): m/z=483.3.

Example 23

(3EZ,5S)-1-([1,1'-biphenyl]-4-ylcarbonyl)-5-[5-(2-phenoxyethyl)-1,2,4-oxadiazol-3-yl]-3-pyrrolidinone O-methyloxime

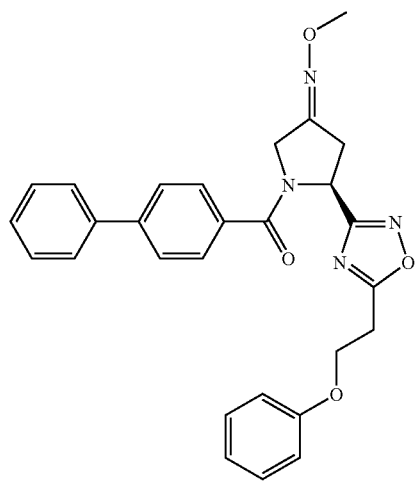

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 3-phenoxypropanoic acid, the title compound was obtained in 84% purity by HPLC. MS(ESI$^+$): m/z=483.3.

Example 24

(3EZ,5S)-1-([1,1'-biphenyl]-4-ylcarbonyl)-5-[5-(2-methoxyethyl)-1,2,4-oxadiazol-3-yl]-3-pyrrolidinone O-methyloxime

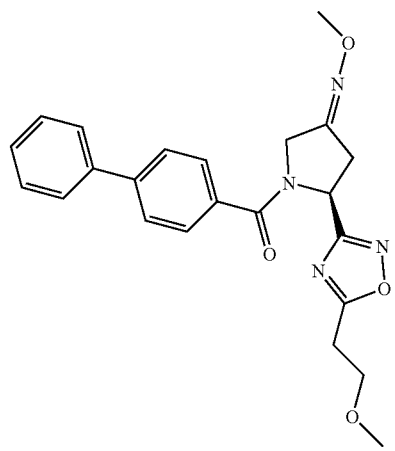

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 3-methoxypropanoic acid, the title compound was obtained in 80% purity by HPLC. MS(ESI$^+$): m/z=421.1.

Example 25

(3EZ,5S)-5-[5-(1-acetyl-4-piperidinyl)-1,2,4-oxadiazol-3-yl]-1-([1,1'-biphenyl]-4-ylcarbonyl)-3-pyrrolidinone O-methyloxime

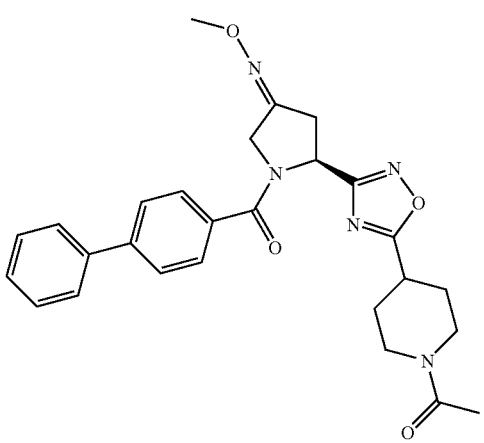

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 1-acetyl-4-piperidinecarboxylic acid, the title compound was obtained in 87% purity by HPLC. MS(ESI+): m/z=488.4.

Example 26

(3EZ,5S)-1-([1,1'-biphenyl]-4-ylcarbonyl)-5-[5-(2-pyridinyl)-1,2,4-oxadiazol-3-yl]-3-pyrrolidinone O-methyloxime

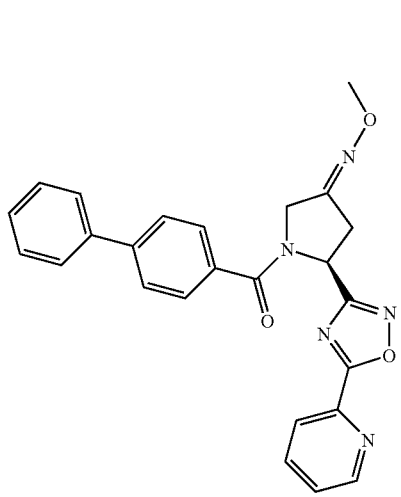

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 2-pyridinecarboxylic acid, the title compound was obtained in 82% purity by HPLC. MS(ESI+): m/z=440.2.

Example 27

(3EZ,5S)-1-([1,1'-biphenyl]-4-ylcarbonyl)-5-[5-(3-thienyl)-1,2,4-oxadiazol-3-yl]-3-pyrrolidinone O-methyloxime

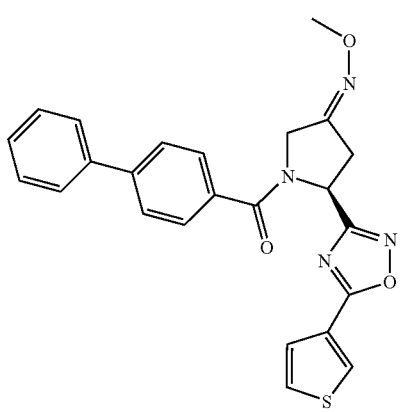

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 3-thiophenecarboxylic acid, the title compound was obtained in 64% purity by HPLC. MS(ESI+): m/z=445.2.

Example 28

(3EZ,5S)-1-([1,1'-biphenyl]-4-ylcarbonyl)-5-(5-ethyl-1,2,4-oxadiazol-3-yl)-3-pyrrolidinone O-methyloxime

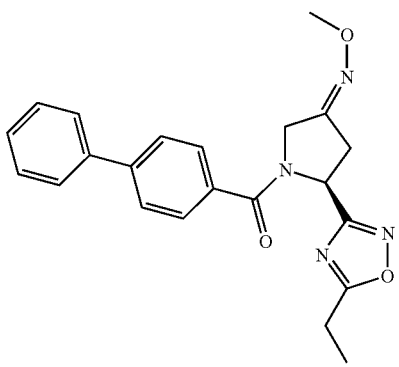

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and propionic acid, the title compound was obtained in 47% purity by HPLC. MS(ESI+): m/z=391.1.

Example 29

(3EZ,5S)-1-([1,1'-biphenyl]-4-ylcarbonyl)-5-(5-cyclopentyl-1,2,4-oxadiazol-3-yl)-3-pyrrolidinone O-methyloxime

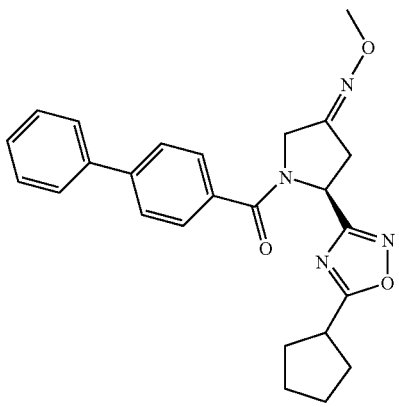

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and cyclopentanecarboxylic acid, the title compound was obtained in 62% purity by HPLC. MS(ESI+): m/z=431.1.

Example 30

(3EZ,5S)-1-([1,1'-biphenyl]-4-ylcarbonyl)-5-(5-methyl-1,2,4-oxadiazol-3-yl)-3-pyrrolidinone O-methyloxime

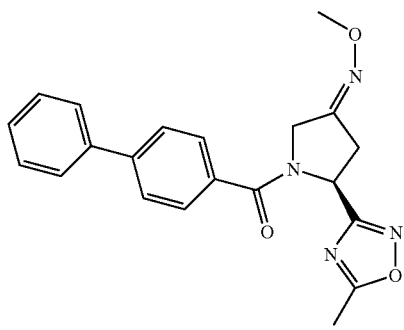

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and acetic acid, the title compound was obtained in 76% purity by HPLC. MS(ESI$^+$): m/z=377.0.

Example 31

(3EZ,5S)-1-([1,1'-biphenyl]-4-ylcarbonyl)-5-{5-[(RS)-hydroxy(phenyl)methyl]-1,2,4-oxadiazol-3-yl}-3-pyrrolidinone O-methyloxime

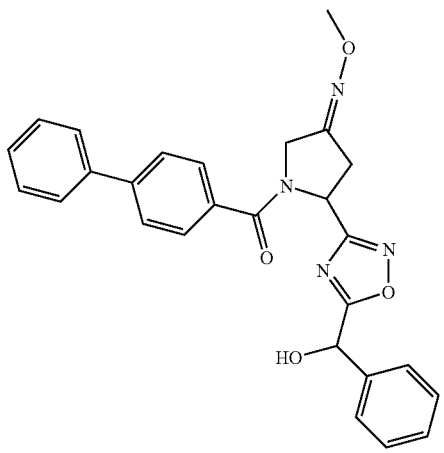

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2RS)-hydroxy(phenyl)ethanoic acid, the title compound was obtained in 73% purity by HPLC. MS(ESI$^+$): m/z=469.3.

Example 32

(3EZ,5S)-1-([1,1'-biphenyl]-4-ylcarbonyl)-5-{5-[(1RS)-1-hydroxy-2-phenylethyl]-1,2,4-oxadiazol-3-yl}-3-pyrrolidinone O-methyloxime

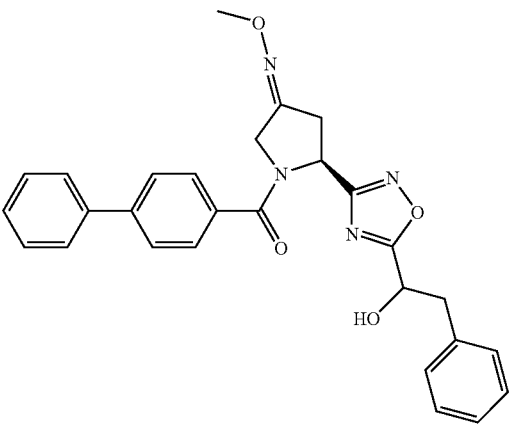

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2RS)-2-hydroxy-3-phenylpropanoic acid, the title compound was obtained in 78% purity by HPLC. MS(ESI$^+$): m/z=483.3.

Example 33

(3EZ,5S)-1-([1,1'-biphenyl]-4-ylcarbonyl)-5-{5-[(1R)-1-(dimethylamino)-2-phenylethyl]-1,2,4-oxadiazol-3-yl}-3-pyrrolidinone O-methyloxime

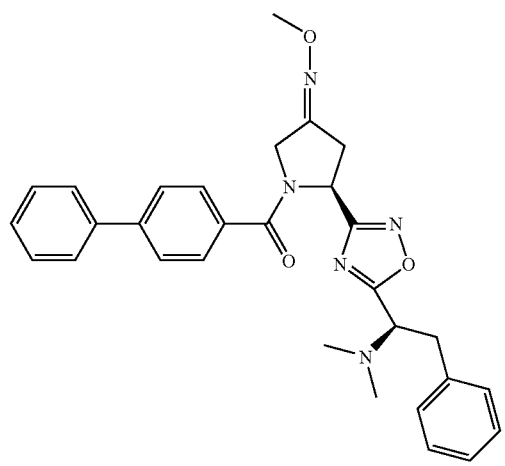

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2R)-2-(dimethylamino)-3-phenylpropanoic acid, the title compound was obtained in 54% purity by HPLC. MS(ESI$^+$): m/z=510.6.

Example 34

(3EZ,5S)-1-([1,1'-biphenyl]-4-ylcarbonyl)-5-[5-(3-pyridinyl-1,2,4-oxadiazol-3-yl]-3-pyrrolidinone O-methyloxime

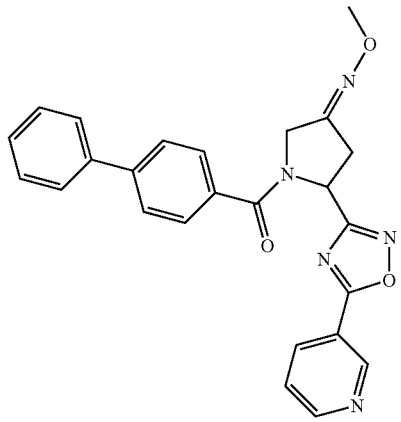

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 3-pyridinecarboxylic acid, the tide compound was obtained in 78% purity by HPLC. MS(ESI$^+$): m/z=440.2.

Example 35

(3EZ,5S)-1-([1,1'-biphenyl]-4-ylcarbonyl)-5-[5-(6-hydroxy-3-pyridinyl)-1,2,4-oxadiazol-3-yl]-3-pyrrolidinone O-methyloxime

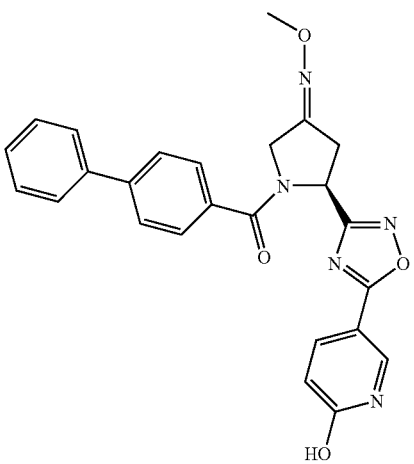

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 6-hydroxynicotinic-acid, the title compound was obtained in 50% yield (90% purity by HPLC).

$^1$H NMR (300 MHz, CDCl$_3$): 2.90–3.30 (m, 2H, CH$_2$), 3.86 (s, 3H, NOCH$_3$), 4.30–4.60 (m, 2H, CH$_2$), 6.04 (m, 1H, CH), 6.70 (d, 1H, H arom), 7.40–7.70 (m, 9H, H arom.); 8.10 (d, 1H, H arom), 8.40 (d, 1H, H arom); MS(ESI$^+$): 456.4; MS(ESI$^-$): 454.2.

Example 36

(3EZ,5S)-1-([1,1'-biphenyl]-4-ylcarbonyl)-5-{5-[(dimethylamino)methyl]-1,2,4-oxadiazol-3-yl}-3-pyrrolidinone O-methyloxime; (3Z,5S)-1-([1,1'-biphenyl]-4-ylcarbonyl)-5-{5-[(dimethylamino)methyl]-1,2,4-oxadiazol-3-yl}-3-pyrrolidinone O-methyloxime; (3E,5S)-1-([1,1'-biphenyl]-4-ylcarbonyl)-5-{5-[(dimethylamino)methyl]-1,2,4-oxadiazol-3-yl}-3-pyrrolidinone O-methyloxime

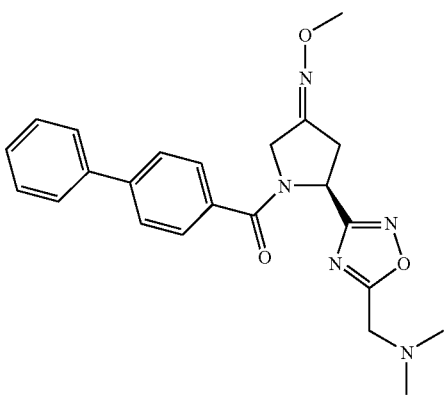

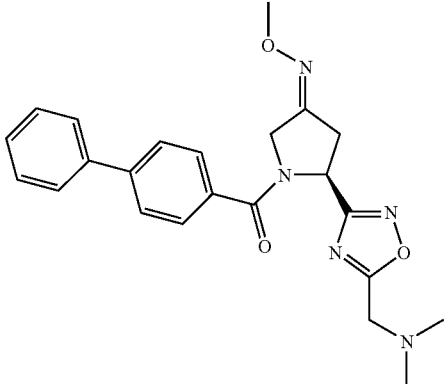

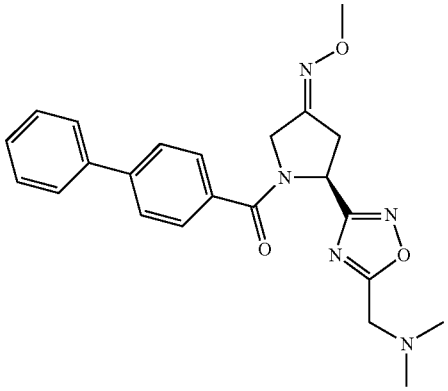

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (dimethylamino)acetic acid, the title compound was obtained in 50% overall yield (96% purity by HPLC) as a micture of E- and Z-isomers. Flash-chromatographic separation afforded the pure Z-isomer in a 23% yield (98.5% purity by HPLC), and the pure E-isomer in 20% yield (98.2% purity by HPLC).

(3EZ,5S)-1-([1,1'-biphenyl]-4-ylcarbonyl)-5-{5-[(dimethylamino)methyl]-1,2,4-oxadiazol-3-yl}-3-pyrrolidinone O-methyloxime: $^1$H NMR (300 MHz, CDCl$_3$): 2.42 (s, 6H, CH$_3$), 2.90–3.30 (m, 2H, CH$_2$), 3.86 (s, 3H, NOCH$_3$), 4.30–4.60 (m, 2H, CH$_2$), 6.01 (m, 1H, CH), 7.40–7.70 (m, 9H, H arom.); MS(ESI$^+$): 420.4.

(3Z,5S)-1-([1,1'-biphenyl]-4-ylcarbonyl)-5-{5-[(dimethylamino)methyl]-1,2,4-oxadiazol-3-yl}-3-pyrrolidinone O-methyloxime: $^1$H NMR (300 MHz, CDCl$_3$): 2.42 (s, 6H, CH$_3$), 2.90–3.30 (m, 2H, CH$_2$), 3.86 (s, 3H, NOCH$_3$), 4.30–4.60 (m, 2H, CH$_2$), 6.01 (m, 1H, CH), 7.40–7.70 (m, 9H, H arom.); MS(ESI$^+$): 420.4.

(3E,5S)-1-([1,1'-biphenyl]-4-ylcarbonyl)-5-{5-[(dimethylamino)methyl]-1,2,4-oxadiazol-3-yl}-3-pyrrolidinone O-methyloxime: $^1$H NMR (300 MHz, CDCl$_3$): 2.42 (s, 6H, CH$_3$), 2.90–3.30 (m, 2H, CH$_2$), 3.86 (s, 3H, NOCH$_3$), 4.30–4.60 (m, 2H, CH$_2$), 6.01 (m, 1H, CH), 7.40–7.70 (m, 9H, H arom.); MS(ESI$^+$): 420.4.

Example 37

4-({3-[(2S,4EZ)-1-([1,1'-biphenyl]-4-ylcarbonyl)-4-(methoxyimino)pyrrolidinyl]-1,2,4-oxadiazol-5-yl}methyl)-2,6-piperazinedione

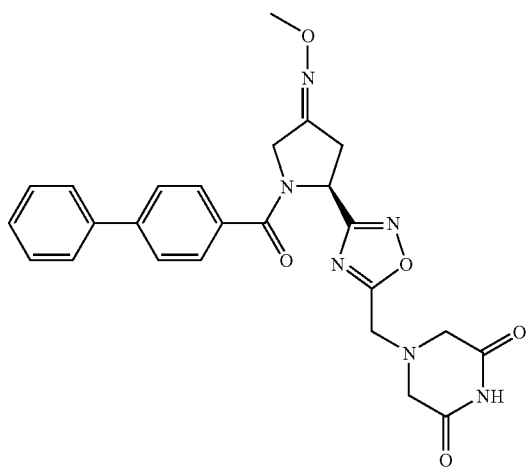

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (3,5-dioxo-1-piperazinyl)acetic acid, the title compound was obtained in 55% yield (99.0% purity by HPLC).

$^1$H NMR (300 MHz, CDCl$_3$): 2.80–3.30 (m, 2H, CH$_2$), 3.61 (s, 4H, CH$_2$), 3.86 (s, 3H, NOCH$_3$), 4.09 (m, 2H, CH$_2$), 4.30–4.60 (m, 2H, CH$_2$), 6.02 (m, 1H, CH), 7.42–7.75 (m, 9H, H arom), 8.56 (m, 1H, NH); MS(ESI$^+$): 489.20; MS(ESI$^-$): 487.17.

Example 38

(3EZ,5S)-([1,1'-biphenyl]-4-ylcarbonyl)-5-{5-[2-(dimethylamino)ethyl]-1,2,4-oxadiazol-3-yl}-3-pyrrolidinone O-methyloxime

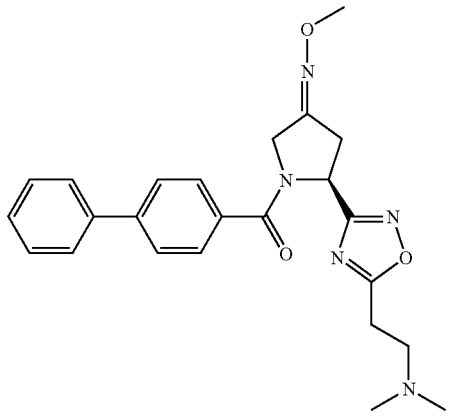

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and N,N-dimethyl-β-alanine, the title compound was obtained in 25% yield (91.5% purity by HPLC).

$^1$H NMR (300 MHz, CDCl$_3$): 2.31 (s, 6H, CH$_3$), 2.80–3.40 (m, 6H, CH$_2$), 3.88 (s, 3H, NOCH$_3$), 4.30–4.60 (m, 2H, CH$_2$), 6.03 (m, 1H, CH), 7.40–7.63 (m, 9H, H arom.); MS(ESI$^+$): 434.4.

Example 39 tert-butyl (4S)-4-{3-[(2S,4EZ)-1-([1,1'-biphenyl]-4-ylcarbonyl)-4-(methoxyimino)pyrrolidinyl]-1,2,4-oxadiazol-5-yl}-4-[(tert-butoxycarbonyl)amino]butanoate

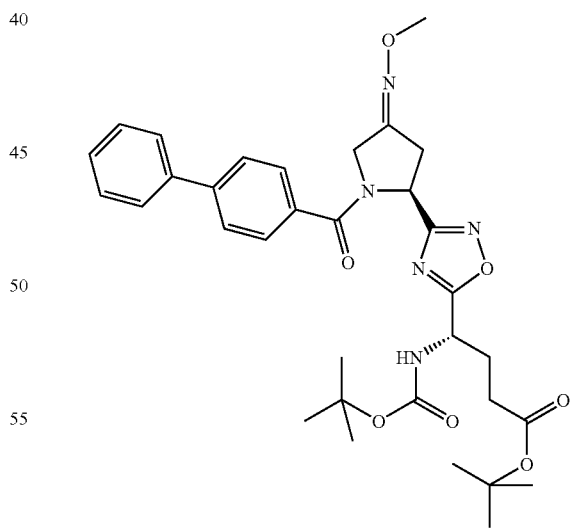

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2S)-5-tert-butoxy-2-[(tert-butoxycarbonyl)amino]-5-oxopentanoic acid, the title compound was obtained in 75% yield (78.9% purity by HPLC).

$^1$H NMR (300 MHz, CDCl$_3$): 1.31 (s, 18H, CH$_3$), 2.05–2.45 (m, 4H, CH$_2$), 2.70–2.95 (m, 2H, CH$_2$), 3.87 (s,

3H, NOCH₃), 4.30–4.55 (m, 2H, CH₂), 5.10 (m, 1H, CH), 6.03 (m, 1H, CH), 7.40–7.63 (m, 9H, H arom.); MS(ESI⁺): 620.3, MS(ESI⁻): 618.3.

Example 40

(3EZ,5RS)-1-([1,1'-biphenyl]-4-ylcarbonyl)-5-[5-(1-methyl-3-piperidinyl)-1,2,4-oxadiazol-3-yl]-3-pyrrolidinone O-methyloxime

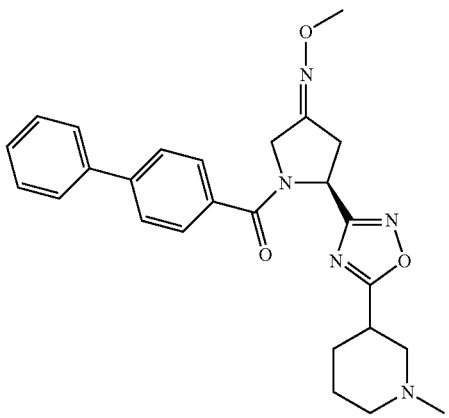

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 1-methyl-3-piperidinecarboxylic acid, the title compound was obtained in 72% yield (99.2% purity by HPLC).

¹H NMR (300 MHz, CDCl₃): 1.60–1.80 (m, 3H, CH, CH₂), 2.05–2.15 (m, 2H, CH₂), 2.33 (s, 3H, CH₃); 2.92–3.22 (m, 6H, CH₂), 3.84 (s, 3H, NOCH₃), 4.34–4.50 (m, 2H, CH₂), 6.01 (m, 1H, CH), 7.38–7.63 (m, 9H, H arom.); MS(ESI⁺): 460.5

Example 41

(3EZ,5S)-1-([1,1'-biphenyl]-4-ylcarbonyl)-5-[5-(1-methyl-4-piperidinyl)-1,2,4-oxadiazol-3-yl]-3-pyrrolidinone O-methyloxime

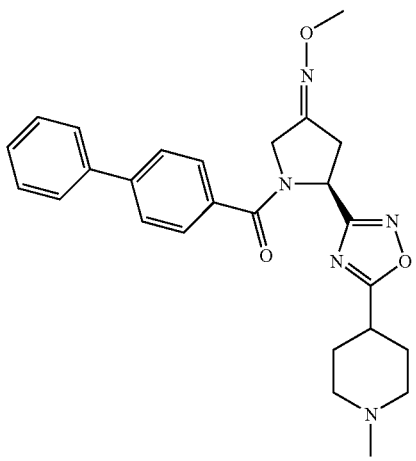

Following the general method as outlined in Example 15, starting from (2S,4EZ)-1-([1,1'-biphenyl]-4-ylcarbonyl)-1-hydroxy-4-(methoxyimino)-2-pyrrolidinecarboximidamide (Intermediate 8) and 1-methyl-4-piperidinecarboxylic acid, the title compound was obtained in 85% yield (96.9% purity by HPLC).

¹H NMR (300 MHz, CDCl₃): 1.98–2.14 (m, 5H, CH, CH₂), 2.32 (s, 3H, CH₃), 2.89–3.20 (m, 6H, CH₂), 3.86 (s, 3H, NOCH₃), 4.34–4.50 (m, 2H, CH₂), 6.02 (m, 1H, CH), 7.38–7.63 (m, 9H, H arom.); MS(ESI⁺): 460.4

Example 42

(3EZ,5S)-1-([1,1'-biphenyl]-4-ylcarbonyl)-5-(5-vinyl-1,2,4-oxadiazol-3-yl)-3-pyrrolidinone O-methyloxime

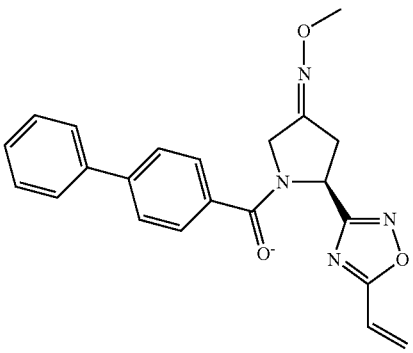

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and acrylic acid, this compound was obtained in 20% yield (89.4% purity by HPLC).

¹H NMR (300 MHz, CDCl₃): 2.85–3.15 (m, 2H, CH₂), 3.78 (s, 3H, NOCH₃), 4.28–4.44 (m, 2H, CH₂), 5.89 (m, 2H, CH), 6.45 (d, 1H, CH), 6.53 (d, 1H, CH), 7.30–7.56 (m, 9H, H arom.); MS(ESI⁺): 389.2.

Example 43 tert-butyl (3R)-3-{3-[(2S,4EZ)-1-([1,1'-biphenyl]-4-ylcarbonyl-4-(methoxyimino)pyrrolidinyl]-1,2,4-oxadiazol-5-yl}-1-piperidinecarboxylate; (3EZ,5S)-1-([1,1'-biphenyl]-4-ylcarbonyl)-5-{5-[(3R)-piperidinyl]-1,2,4-oxadiazol-3-yl}-3-pyrrolidinone O-methyloxime

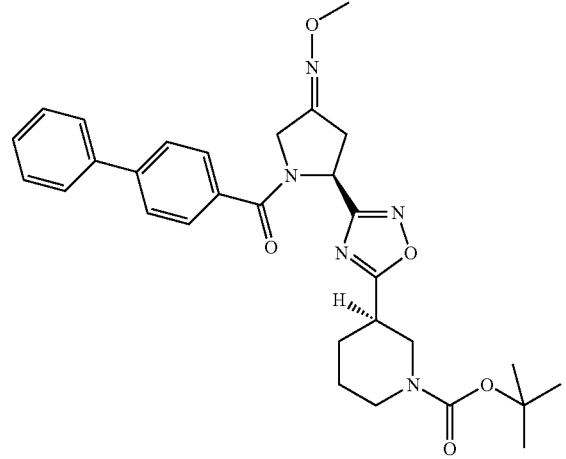

-continued

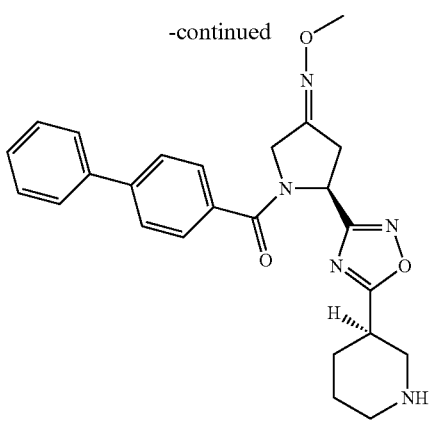

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (3R)-1-(tert-butoxycarbonyl)-3-piperidinecarboxylic acid, the title compound, tert-butyl (3R)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate, was obtained in 85% yield (96.5% purity by HPLC).

MS(ESI$^+$): 546.5.

tert-butyl (3R)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded a residue, which was purified by flash-chromatography using dichloromethane/methanol as eluent to give the desired product, (3EZ,5S)-1-([1,1'-biphenyl]-4-ylcarbonyl)-5-{5-[(3R)-piperidinyl]-1,2,4-oxadiazol-3-yl}-3-pyrrolidinone O-methyloxime, as a mixture of E-/Z-isomers in a 80% yield (95.7% purity by HPLC).

$^1$H NMR (300 MHz, CDCl$_3$): 1.62–1.92 (m, 3H, CH$_2$), 2.20–2.42 (m, 2H, CH$_2$), 2.75–3.41 (m, 7H, CH$_2$), 3.86 (s, 3H, NOCH$_3$), 4.36–4.51 (m, 2H, CH$_2$), 6.02 (m, 1H, CH), 7.40–7.64 (m, 9H, H arom); MS(ESI$^+$): 446.2.

Example 44

(3EZ,5S)-1-([1,1'-biphenyl]-4-ylcarbonyl)-5-{5-[(3)-1-methylpiperidinyl]-1,2,4-oxadiazol-3-yl}-3-pyrrolidinone O-methyloxime

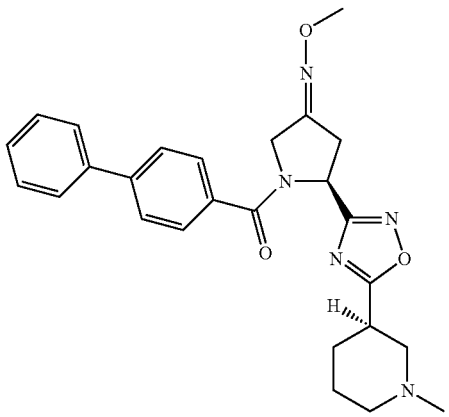

A solution containing 1 equivalent of (3EZ,5S)-1-([1,1'-biphenyl]-4-ylcarbonyl)-5-{5-[(3R)-piperidinyl]-1,2,4-oxadiazol-3-yl}-3-pyrrolidinone O-methyloxime (Example 43), dissolved in dry DCM at 0° C. in presence of 1.5 equivalent of triethyl amine, was reacted with 1 equivalent of methyl iodide. The reaction mixture was stirred at room temperature for 12 hours. The reaction was hydrolyzed and then made basic with sodium carbonate solution (10%) and extracted with DCM. The organic phase was then dried with magnesium sulfate, and concentrated in vacuo to give a residue which was purified by flash-chromatography using dichloromethane/methanol as eluent to give the expected product, (3EZ,5S)-1-([1,1'-biphenyl]-4-ylcarbonyl)-5-{5-[(3R)-1-methylpiperidinyl]-1,2,4-oxadiazol-3-yl}-3-pyrrolidinone O-methyloxime, as a mixture of E-/Z-isomers, in 45% yield (97.6% purity by HPLC).

$^1$H NMR (300 MHz, CDCl$_3$): 1.61–1.90 (m, 3H, CH$_2$), 2.01–2.20 (m, 3H, CH$_2$), 2.23 (m, 3H, CH$_3$), 2.70–3.30 (m, 5H, CH$_2$), 3.77 (s, 3H, NOCH$_3$), 4.30–4.52 (m, 2H, CH$_2$), 6.01 (m, 1H, CH), 7.38–7.70 (m, 9H, H arom.); MS(ESI$^+$): 460.2.

Example 45 tert-butyl (3S)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate; (3EZ,5S)-1-([1,1'-biphenyl]-4-ylcarbonyl)-5-{5-[(3S)-piperidinyl]-1,2,4-oxadiazol-3-yl}-3-pyrrolidinone O-methyloxime

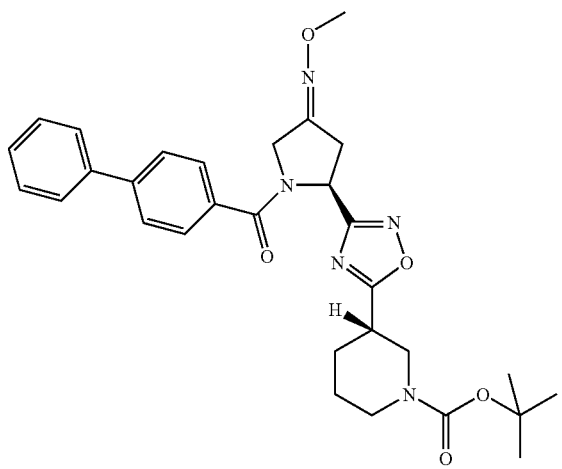

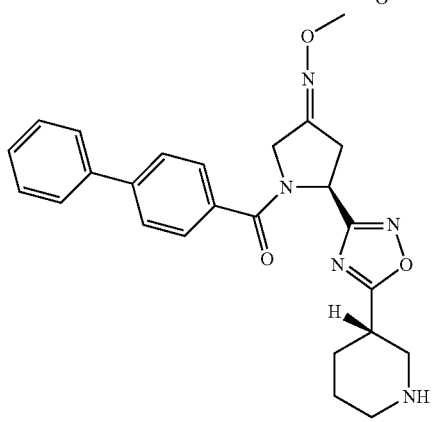

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (3S)-1-(tert-butoxycarbonyl)-3-piperidinecarboxylic acid, the title compound, tert-butyl (3S)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate, was obtained in 85% yield (97.20% purity by HPLC).

MS(ESI+): 546.5 tert-butyl (3S)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded a residue, which was purified by flash-chromatography using dichloromethane/methanol as eluent to give the desired product, (3EZ,5S)-1-([1,1'-biphenyl]-4-ylcarbonyl)-5-{5-[(3S)-piperidinyl]-1,2,4-oxadiazol-3-yl}-3-pyrrolidinone O-methyloxime, as a mixture of E-/Z-isomers in a 85% yield (95.1% purity by HPLC).

$^1$H NMR (300 MHz, CDCl$_3$): 1.62–1.92 (m, 3H, CH$_2$), 2.20–2.42 (m, 2H, CH$_2$), 2.75–3.41 (m, 7H, CH$_2$), 3.86 (s, 3H, NOCH$_3$), 4.36–4.51 (m, 2H, CH$_2$), 6.02 (m, 1H, CH), 7.40–7.64 (m, 9H, H arom); MS(ESI+): 446.2.

Example 46

(3EZ,5S)-1-([1,1'-biphenyl]-4-ylcarbonyl)-5-{5-[(3S)-1-methylpiperidinyl]-1,2,4-oxadiazol-3-yl}-3-pyrrolidinone O-methyloxime

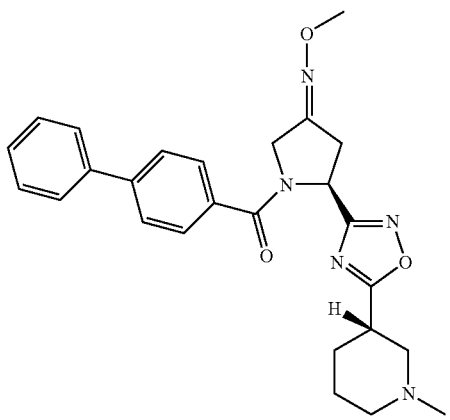

A solution containing 1 equivalent of (3EZ,5S)-1-([1,1'-biphenyl]-4-ylcarbonyl)-5-{5-[(3S)-piperidinyl]-1,2,4-oxadiazol-3-yl}-3-pyrrolidinone O-methyloxime (Example 45), dissolved in dry DCM at 0° C. in presence of 1.5 equivalent of triethyl amine, was reacted with 1 equivalent of methyl iodide. The reaction mixture was stirred at room temperature for 12 hours. The reaction was hydrolyzed and then made basic with sodium carbonate solution (10%) and extracted with DCM. The organic phase was then dried with magnesium sulfate, and concentrated in vacuo to give a residue which was purified by flash-chromatography using dichloromethane/methanol as eluent to give the expected product, (3EZ,5S)-1-([1,1'-biphenyl]-4-ylcarbonyl)-5-{5-[(3S)-1-methylpiperidinyl]-1,2,4-oxadiazol-3-yl}-3-pyrrolidinone O-methyloxime, as a mixture of E-/Z-isomers, in 55% yield (97.9% purity by HPLC).

$^1$H NMR (300 MHz, CDCl$_3$): 1.61–1.90 (m, 3H, CH$_2$), 2.01–2.20 (m, 3H, CH$_2$), 2.33 (m, 3H, CH$_3$), 2.70–3.30 (m, 5H, CH$_2$), 3.84 (s, 3H, NOCH$_3$), 4.30–4.52 (m, 2H, CH$_2$), 6.01 (m, 1H, CH), 7.38–7.70 (m, 9H, H arom.); MS(ESI+): 460.2.

Example 47 tert-butyl 4-(2-{3-[(2S,4EZ)-1-([1,1'-biphenyl]-4-ylcarbonyl)-4-(methoxyimino)pyrrolidinyl]-1,2,4-oxadiazol-5-yl}ethyl)-1-piperazinecarboxylate

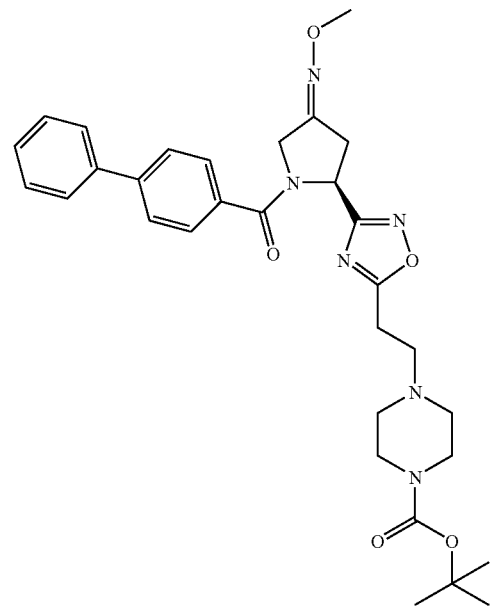

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and 3-[4-(tert-butoxycarbonyl)-1-piperazinyl]propanoic acid, the title compound was obtained in 70% yield (78% purity by HPLC).

$^1$H NMR (300 MHz, CDCl$_3$): 1.38 (s, 9H, CH$_3$), 2.38 (m, 4H, CH$_2$), 2.70–2.85 (m, 6H, CH$_2$), 3.34 (m, 4H, CH$_2$), 3.84 (s, 3H, NOCH$_3$), 4.23–4.42 (m, 2H, CH$_2$), 5.92 (m, 1H, CH), 7.19–7.53 (m, 9H, H arom.); MS(ESI+): 575.5.

Example 48 tert-butyl 4-({3-[(2S,4EZ)-1-([1,1'-biphenyl]-4-yl-carbonyl)-4-(methoxyimino)pyrrolidinyl]-1,2,4-oxa-diazol-5-yl}methyl)-1-piperazinecarboxylate; (3EZ, 5S)-1-([1,1'-biphenyl]-4-ylcarbonyl)-5-[5-(1-piperazinylmethyl)-1,2,4-oxadiazol-3-yl]-3-pyrrolidinone O-methyloxime

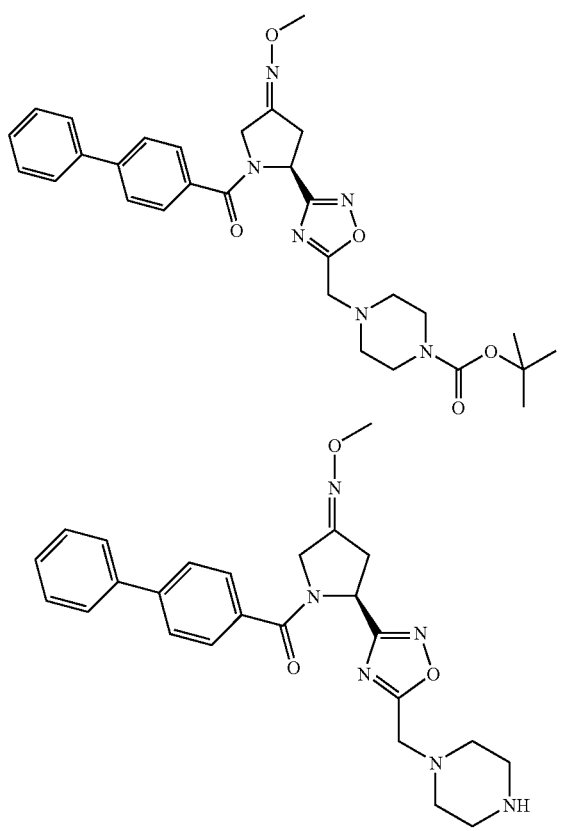

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and [4-(tert-butoxycarbonyl)-1-piperazinyl]acetic acid, the title compound, tert-butyl 4-({3-[(2S,4EZ)-1-([1,1'-biphenyl]-4-ylcarbonyl)-4-(methoxyimino)pyrrolidinyl]-1,2,4-oxadiazol-5-yl}methyl)-1-piperazinecarboxylate, was obtained in 75% yield (88% purity by HPLC).

$^1$H NMR (300 MHz, CDCl$_3$): 1.38 (s, 9H, CH$_3$), 2.38 (m, 4H, CH$_2$), 2.70–2.85 (m, 4H, CH$_2$), 3.34 (m, 4H, CH$_2$), 3.84 (s, 3H, NOCH$_3$), 4.23–4.42 (m, 2H, CH$_2$), 5.92 (m, 1H, CH), 7.19–7.53 (m, 9H, H arom.); MS(ESI$^+$): 561.5.

tert-butyl 4-({3-[(2S,4EZ)-1-([1,1'-biphenyl]-4-ylcarbonyl)-4-(methoxyimino)pyrrolidinyl]-1,2,4-oxadiazol-5-yl}methyl)-1-piperazinecarboxylate (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded a residue, which was purified by flash-chromatography using dichloromethane/methanol as eluent to give the desired product, (3EZ,5S)-1-([1,1'-biphenyl]-4-ylcarbonyl)-5-[5-(1-piperazinylmethyl)-1,2,4-oxadiazol-3-yl]-3-pyrrolidinone O-methyloxime, as a mixture of E-/Z-isomers in a 85% yield (94.3% purity by HPLC).

$^1$H NMR (300 MHz, CDCl$_3$): 2.50 (m, 4H, CH$_2$), 2.85–2.87 (m, 4H, CH$_2$), 3.04–3.19 (m, 2H, CH$_2$), 3.76 (s, 5H, CH$_2$, NOCH$_3$), 4.27–4.42 (m, 2H, CH$_2$), 5.94 (m, 1H, CH), 7.20–7.54 (m, 9H, H arom.); MS(ESI$^+$): 461.2.

Example 49

(3EZ,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime; (3Z,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime

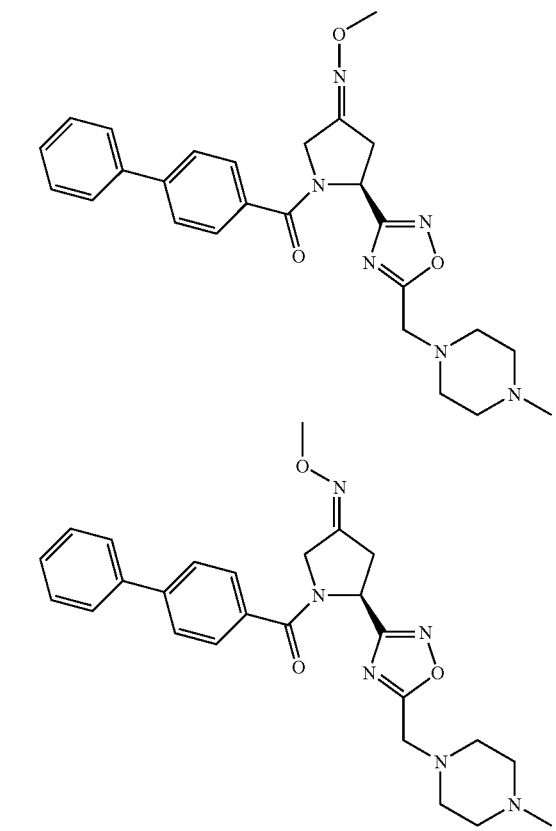

A solution containing 1 equivalent of (3EZ,5S)-1-([1,1'-biphenyl]-4-ylcarbonyl)-5-[5-(1-piperazinylmethyl)-1,2,4-oxadiazol-3-yl]-3-pyrrolidinone O-methyloxime (Example 48), dissolved in dry DCM at 0° C. in presence of 1.5 equivalent of triethyl amine, was reacted with 1 equivalent of methyl iodide. The reaction mixture was stirred at room temperature for 12 hours. The reaction was hydrolyzed and then made basic with sodium carbonate solution (10%) and extracted with DCM. The organic phase was then dried with magnesium sulfate, and concentrated in vacuo to give a residue which was purified by flash-chromatography using dichloromethane/methanol as eluent to give the expected product, (3EZ,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime, as a mixture of E-/Z-isomers, in 50% yield (99.9% purity by HPLC). The pure Z-isomer could be separated by flash-chromatography, and was obtained in 31% yield (98.9% purity by HPLC).

(3EZ,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime: $^1$H NMR (300 MHz, CDCl$_3$): 2.32 (s, 3H, CH$_3$), 2.50–3.20 (m, 10H, CH$_2$), 3.78–3.92 (m, 5H, CH$_2$; NOCH$_3$), 4.27–4.45 (m, 2H, CH$_2$); 5.95 (m, 1H, CH), 7.32–7.57 (m, 9H, H arom); MS(ESI$^+$): 475.2.

(3Z,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime: $^1$H NMR (300 MHz, CDCl$_3$): 2.32 (s, 3H, CH$_3$), 2.50–3.20 (m, 10H, CH$_2$), 3.78–3.92 (m, 5H, CH$_2$; NOCH$_3$), 4.27–4.45 (m, 2H, CH$_2$), 5.95 (m, 1H, CH), 7.32–7.57 (m, 9H, H arom); MS(ESI$^+$): 475.2.

Example 50

(3EZ,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime; (3Z,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime

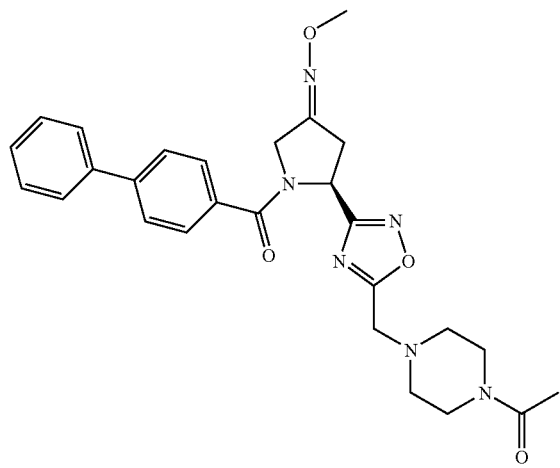

To a solution containing 1 equivalent of (3EZ,5S)-1-([1,1'-biphenyl]-4-ylcarbonyl)-5-[5-(1-piperazinylmethyl)-1,2,4-oxadiazol-3-yl]-3-pyrrolidinone O-methyloxime (Example 48) in dry DCM at 0° C. were added 1.5 equivalent of triethyl amine and 1 equivalent of acetyl chloride. The reaction mixture was stirred at this temperature for 30 minutes and then hydrolyzed with ice. The reaction was then made basic with a sodium carbonate solution (10%) and extracted with DCM. The organic phase was dried with magnesium sulfate and solvent removal afforded a residue which was purified by flash-chromatography to give the expected product, (3EZ,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime as a mixture of E-/Z-isomers, in 70% yield (94.4% purity by HPLC). The pure Z-isomer could be separated by flash-chromatography using cyclohexane/ethylacetate (1/1) as eluent, and was obtained in 40% yield (98.0% purity by HPLC).

(3EZ,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime: $^1$H NMR (300 MHz, CDCl$_3$): 2.09 (m, 3H, CH$_3$), 2.65 (s, 4H, CH$_2$), 2.90–3.20 (m, 2H, CH$_2$), 3.54 (m, 2H, CH$_2$), 3.71 (m, 2H, CH$_2$), 3.85–3.92 (m, 5H, CH$_2$; NOCH$_3$), 4.36–4.50 (m, 2H, CH$_2$), 6.02 (m, 1H, CH), 7.40–7.75 (m, 9H, H arom); MS(ESI$^+$): 503.2.

(3Z,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime: $^1$H NMR (300 MHz, CDCl$_3$): 2.09 (3H CH$_3$), 2.65 (s, 4H, CH$_2$), 2.90–3.20 (m, 2H, CH$_2$), 3.54 (m, 2H, CH$_2$), 3.71 (m, 2H, CH$_2$), 3.85–3.92 (m, 5H, CH$_2$; NOCH$_3$), 4.36–4.50 (m, 2H, CH$_2$), 6.02 (m, 1H, CH), 7.40–7.75 (m, 9H, H arom); MS(ESI$^+$): 503.2.

Example 50

4-{[(2S,4EZ)-2-(5-{[(tert-butoxycarbonyl)amino]methyl}-1,2,4-oxadiazol-3-yl)-4-(methoxyimino)pyrrolidinyl]carbonyl}-1,1'-biphenyl

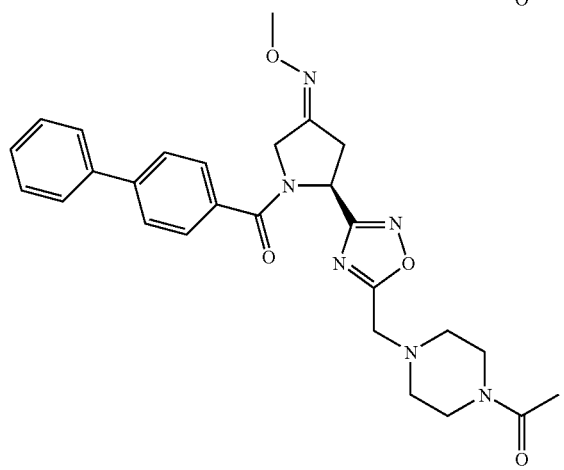

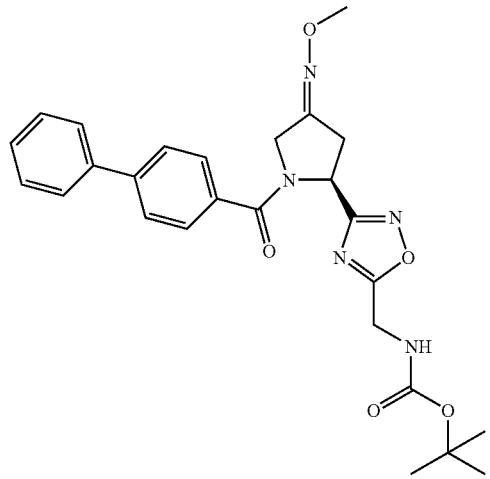

Following the general method as outlined in Example 15, starting from (2S,4EZ)-1-([1,1'-biphenyl]-4-ylcarbonyl)-N'- hydroxy-4-(methoxyimino)-2-pyrrolidinecarboximidamide (Intermediate 8) and [(tert-butoxycarbonyl)amino]acetic acid, the title compound was obtained in 80% yield (78.2% purity by HPLC).

¹H NMR (300 MHz, CDCl₃): 1.48 (s, 9H, CH₃), 1.58 (s, 2H, CH₂), 2.90–3.43 (m, 2H, CH₂), 3.85 (s, 3H, NOCH₃), 4.20–4.60 (m, 2H, CH₂), 6.03 (m, 1H, CH), 7.37–7.63 (m, 9H, H arom.); MS(ESI⁺): 492.20, MS(ESI⁻): 490.2.

Example 51

N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(1-piperidinyl)propanamide

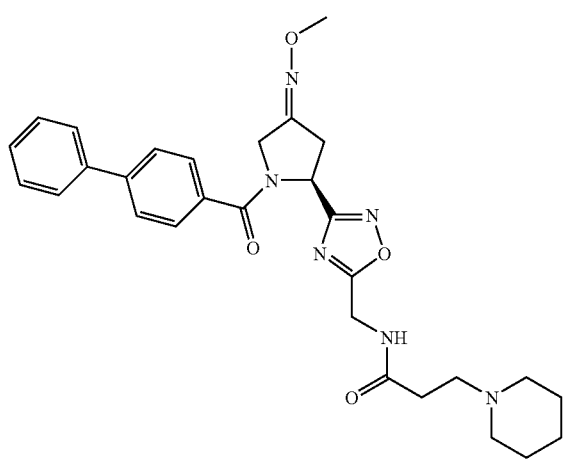

4-{[(2S,4EZ)-2-(5-{[(tert-butoxycarbonyl)amino]methyl}-1,2,4-oxadiazol-3-yl)-4-(methoxyimino)pyrrolidinyl]carbonyl}-1,1'-biphenyl (Example 50) was treated with a 25% TFA/DCM solution at 0° C. The reaction was monitored by LC/MS and stopped after completion. The reaction was then made basic with sodium carbonate solution (10%) and extracted with DCM. The combined organic phases were dried over magnesium sulfate. Solvent removal afforded a crude product, which was used without purification in the next step. The residue was dissolved in DCM at room temperature, DMAP (1.1 equivalent) and 3-(1-piperidinyl)propanoic acid (1 equivalent) were added. The reaction mixture was then cooled down to 0° C. and EDC (1.1 equivalent) was added portion-wise. After stirring for 1 hour at 0° C., the reaction mixture was allowed to warm to room temperature. The reaction was monitored by TLC and LC/MS. Usually after 12 hours stirring at RT, the reaction mixture was hydrolyzed, washed with sodium carbonate solution (10%), dried over MgSO₄, and evaporated in vacuo to give a crude product. Flash chromatography on silica gel, eluting with 60% EtOAc in hexane, gave the title compound as a mixture of E- and Z-isomers in 50% yield (87.4% purity by HPLC).

MS(ESI⁺): 531.5; MS(ESI⁻): 529.2.

Example 52

N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(dimethylamino)propanamide

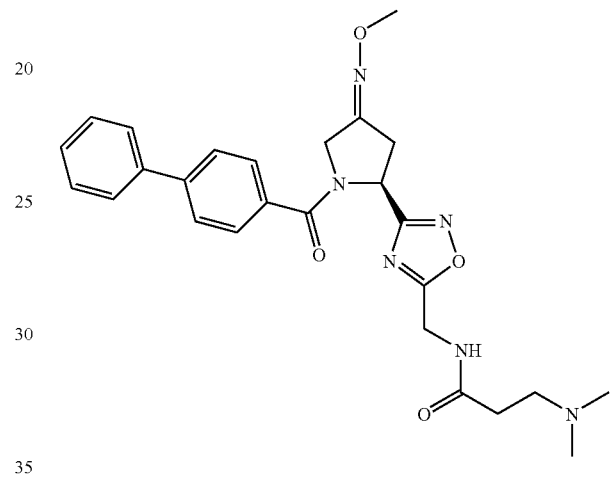

4-{[(2S,4EZ)-2-(5-{[(tert-butoxycarbonyl)amino]methyl}-1,2,4-oxadiazol-3-yl)-4-(methoxyimino)pyrrolidinyl]carbonyl}-1,1'-biphenyl (Example 50) was treated with a 25% TFA/DCM solution at 0° C. The reaction was monitored by LC/MS and stopped after completion. The reaction was then made basic with sodium carbonate solution (10%) and extracted with DCM. The combined organic phases were dried over magnesium sulfate. Solvent removal afforded a crude product, which was used without purification in the next step. The residue was dissolved in DCM at room temperature, DMAP (1.1 equivalent) and N,N-dimethyl-β-alanine (1 equivalent) were added. The reaction mixture was then cooled down to 0° C. and EDC (1.1 equivalent) was added portion-wise. After stirring for 1 hour at 0° C., the reaction mixture was allowed to warm to room temperature. The reaction was monitored by TLC and LC/MS. Usually after 12 hours stirring at RT, the reaction mixture was hydrolyzed, washed with sodium carbonate solution (10%), dried over MgSO₄, and evaporated in vacuo to give a crude product. Flash chromatography on silica gel, eluting with 60% EtOAc in hexane, gave the title compound as a mixture of E- and Z-isomers in 52% yield (82% purity by HPLC).

MS(ESI⁺): 491.2.

Example 53

N-({3-[(2S,4EZ)-1-([1,1'-biphenyl]-4-ylcarbonyl)-4-(methoxyimino)pyrrolidinyl]-1,2,4-oxadiazol-5-yl}methyl)-2-(dimethylamino)acetamide

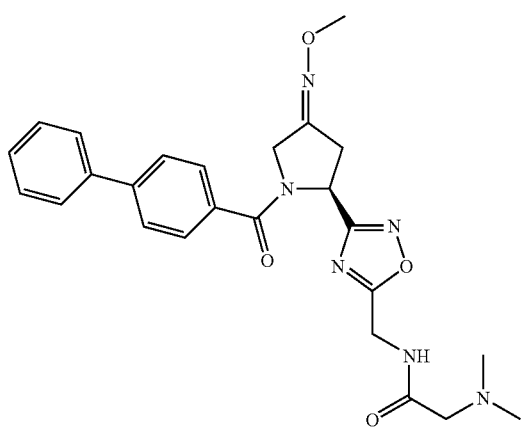

4-{[(2S,4EZ)-2-(5-{[(tert-butoxycarbonyl)amino]methyl}-1,2,4-oxadiazol-3-yl)-4-(methoxyimino)pyrrolidinyl]carbonyl}-1,1'-biphenyl (Example 50) was treated with a 25% TFA/DCM solution at 0° C. The reaction was monitored by LC/MS and stopped after completion. The reaction was then made basic with sodium carbonate solution (10%) and extracted with DCM. The combined organic phases were dried over magnesium sulfate. Solvent removal afforded a crude product, which was used without purification in the next step. The residue was dissolved in DCM at room temperature, DMAP (1.1 equivalent) and (dimethylamino)acetic acid (1 equivalent) were added. The reaction mixture was then cooled down to 0° C. and EDC (1.1 equivalent) was added portion-wise. After stirring for 1 hour at 0° C., the reaction mixture was allowed to warm to room temperature. The reaction was monitored by TLC and LC/MS. Usually after 12 hours stirring at RT, the reaction mixture was hydrolyzed, washed with sodium carbonate solution (10%), dried over MgSO$_4$, and evaporated in vacuo to give a crude product. Flash chromatography on silica gel, eluting with 60% EtOAc in hexane, gave the title compound as a mixture of E- and Z-isomers in 45% yield (88.1% purity by HPLC).

MS(ESI$^+$): 477.25: MS(ESI$^-$): 475.15.

Example 54

4-{[(2S,4EZ)-2-(5-{2-[(tert-butoxycarbonyl)amino]ethyl}-1,2,4-oxadiazol-3-yl)-4-(methoxyimino)pyrrolidinyl]carbonyl}-1,1'-biphenyl

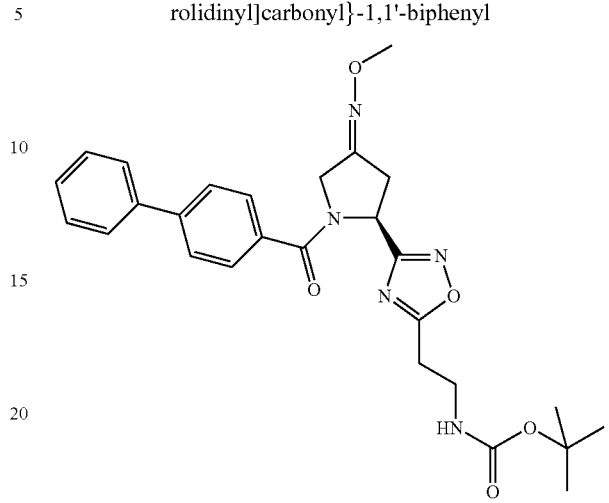

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and N-(tert-butoxycarbonyl)-β-alanine, this compound was obtained in 75% yield (91.9% purity by HPLC).

$^1$H NMR (300 MHz, CDCl$_3$): 1.36 (s, 9H, CH$_3$), 2.80–3.15 (m, 4H, CH$_2$), 3.51 (m, 2H, CH$_2$), 3.78 (s, 3H, NOCH$_3$), 4.27–4.42 (m, 2H, CH$_2$), 5.93 (m, 1H, CH), 7.39–7.56 (m, 9H, H arom.); MS(ESI$^+$): 506.20, MS(ESI$^-$): 504.2.

Example 55

4-{[(2S,4EZ)-2-(5-{(1S)-2-tert-butoxy-1-[(tert-butoxycarbonyl)amino]ethyl}-1,2,4-oxadiazol-3-yl)-4-(methoxyimino)pyrrolidinyl]carbonyl}-1,1'-biphenyl; (3EZ,5S)-5-{5-[(1S)-1-amino-2-tert-butoxyethyl]-1,2,4-oxadiazol-3-yl}-1-([1,1'-biphenyl]-4-ylcarbonyl)-3-pyrrolidinone O-methyloxime; (3EZ,5S)-5-{5-[(1S)-1-amino-2-hydroxyethyl]-1,2,4-oxadiazol-3-yl}-1-([1,1'-biphenyl]-4-ylcarbonyl)-3-pyrrolidinone O-methyloxime

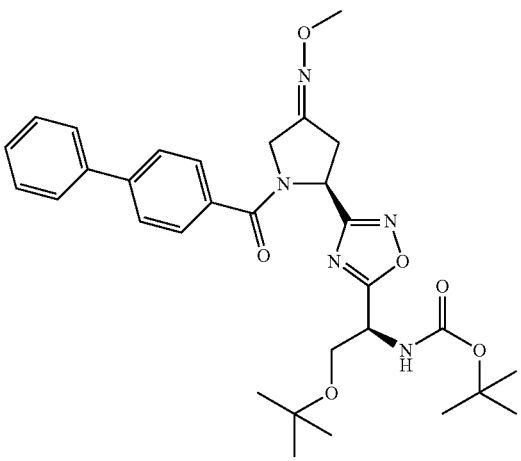

-continued

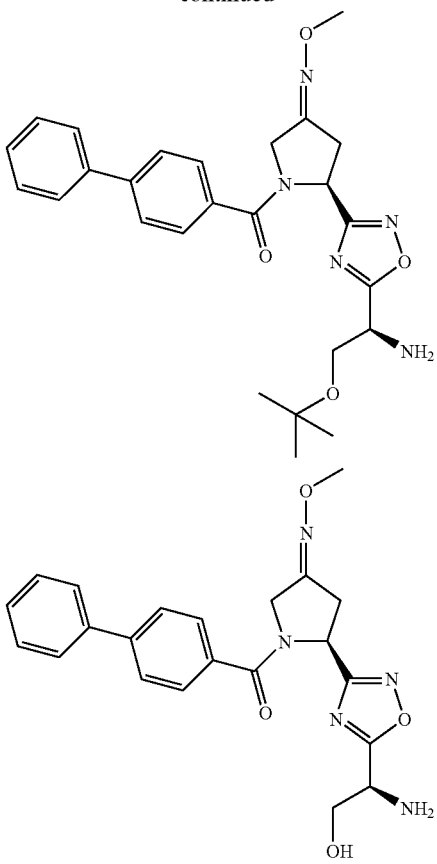

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2S)-3-tert-butoxy-2-[(tert-butoxycarbonyl)amino]propanoic acid, the title compound, 4-{[(2S,4EZ)-2-(5-{(1S)-2-tert-butoxy-1-[(tert-butoxycarbonyl)amino]ethyl}-1,2,4-oxadiazol-3-yl)-4-(methoxyimino)pyrrolidinyl]carboxyl}-1,1'-biphenyl, was obtained in 44% yield (89.4% purity by HPLC).

MS(ESI+): 578.5.

4-{[(2S,4EZ)-2-(5-{(1S)-2-tert-butoxy-1-[(tert-butoxycarbonyl)amino]ethyl}-1,2,4-oxadiazol-3-yl)-4-(methoxyimino)pyrrolidinyl]carbonyl}-1,1'-biphenyl (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded two products, which were separated and purified by flash-chromatography to give the desired products as mixtures of E-/Z-isomers, (3EZ,5S)-5-{5-[(1S)-1-amino-2-tert-butoxyethyl]-1,2,4-oxadiazol-3-yl}-1-([1,1'-biphenyl]-4-ylcarbonyl-3-pyrrolidinone O-methyloxime in 20% yield (80.8% purity by HPLC), and (3EZ,5S)-5-{5-[(1S)-1-amino-2-hydroxyethyl]-1,2,4-oxadiazol-3-yl}-1-([1,1'-biphenyl]-4-ylcarbonyl)-3-pyrrolidinone O-methyloxime in 30% yield (98.1% purity by HPLC).

(3EZ,5S)-5-{5-[(1S)-1-amino-2-tert-butoxyethyl]-1,2,4-oxadiazol-3-yl}-1-([1,1'-biphenyl]-4-ylcarbonyl)-3-pyrrolidinone O-methyloxime: $^1$H NMR (300 MHz, CDCl$_3$): 1.07 (s, 9H, CH$_3$), 1.96 (m, 2H, NH$_2$), 2.83–3.18 (m, 2H, CH$_2$), 3.64–3.78 (m, 5H, CH$_2$, NOCH$_3$), 4.23–4.43 (m, 2H, CH$_2$), 5.96 (m, 1H, CH), 7.30–7.56 (m, 9H, H arom); MS(ESI+): 478.0.

(3EZ,5S)-5-{5-[(1S)-1-amino-2-hydroxyethyl]-1,2,4-oxadiazol-3-yl}-1-([1,1'-biphenyl]-4-ylcarbonyl)-3-pyrrolidinone O-methyloxime: $^1$H NMR (300 MHz, CDCl$_3$): 2.90–3.15 (m, 2H, CH$_2$), 3.86 (s, 3H, NOCH$_3$), 4.05–4.42 (m, 4H, CH$_2$), 4.81 (m, 1H, CH), 5.89 (m, 1H, CH), 7.36–7.62 (m, 9H, H arom); MS(ESI+): 422.20; MS(ESI−): 420.1.

Example 56

4-{[(2S,4EZ)-2-(5-{(1S,2R)-2-tert-butoxy-1-[(tert-butoxycarbonyl)amino]propyl}-1,2,4-oxadiazol-3-yl)-4-(methoxyimino)pyrrolidinyl]carbonyl}-1,1'-biphenyl; (3EZ,5S)-5-{5-(1S,2R)-1-amino-2-hydroxypropyl-1,2,4-oxadiazol-3-yl}-1-([1,1'-biphenyl]-4-ylcarbonyl)-3-pyrrolidinone O-methyloxime

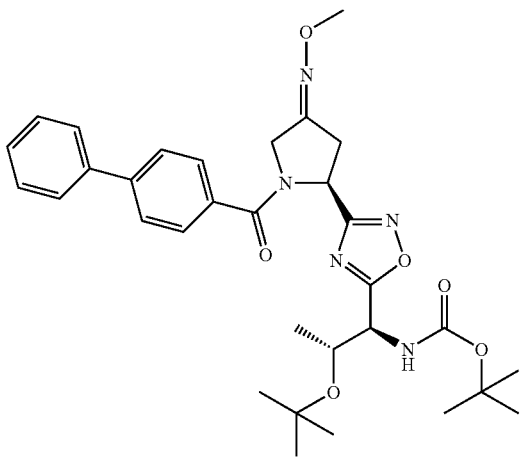

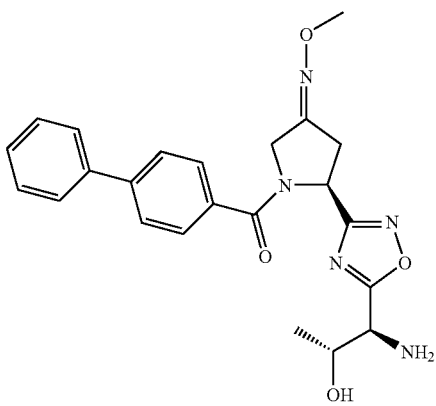

Following the general method as outlined in Example 15, starting from (2S,4EZ)-1-([1,1'-biphenyl]-4-ylcarbonyl)-N'-hydroxy-4-(methoxyimino)-2-pyrrolidinecarboximidamide (Intermediate 8) and (2S,3R)-3-tert-butoxy-2-[(tert-butoxycarbonyl)amino]butanoic acid, the title compound, 4-{[(2S,4EZ)-2-(5-{(1S,2R)-2-tert-butoxy-1-[(tert-butoxycarbonyl)

amino]propyl}-1,2,4-oxadiazol-3-yl)-4-(methoxyimino) pyrrolidinyl]carbonyl}-1,1'-biphenyl, was obtained in 48% yield (85.9% purity by HPLC).

MS(ESI+): 592.7

4-{[(2S,4EZ)-2-(5-{(1S,2R)-2-tert-butoxy-1-[(tert-butoxycarbonyl)amino]propyl}-1,2,4-oxadiazol-3-yl)-4-(methoxyimino)pyrrolidinyl]carbonyl}-1,1'-biphenyl (100 mg, 1.80 mmol) was treated with a 25% TFA/DCM solution at 0° C. for 1 hour. The reaction was then made basic with a sodium carbonate solution (10%) and extracted with DCM. The organic phases were combined and dried over magnesium sulfate and solvent removal afforded a residue, which was purified by flash-chromatography using dichloromethane/methanol as eluent to give the desired product, (3EZ,5S)-5-{5-[(1S,2R)-1-amino-2-hydroxypropyl]-1,2,4-oxadiazol-3-yl}-1-([1,1'-biphenyl]-4-ylcarbonyl)-3-pyrrolidinone O-methyloxime, as a mixture of E-/Z-isomers in 30% yield (90.3% purity by HPLC).

¹H NMR (300 MHz, CDCl₃): 1.24–1.35 (m, 4H, CH₃, CH), 2.94–3.25 (m, 2H, CH₂), 3.83 (s, 3H, NOCH₃), 4.22–4.50 (m, 3H, CH, CH₂), 6.01 (m, 1H, CH), 7.38–7.60 (m, 9H, H arom); MS(ESI+): 436.3.

Example 57 ethyl 5-[(2S,4EZ)-1-([1,1'-biphenyl]-4-ylcarbonyl)-4-(methoxyimino)pyrrolidinyl]-1,2,4-oxadiazole-3-carboxylate

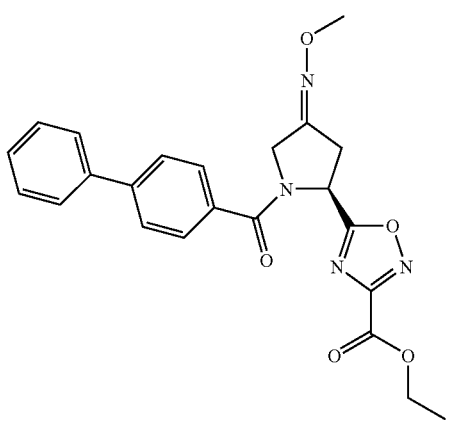

Following the general methods as outlined in Example 1 (Method B), starting from (2S,4EZ)-1-(tert-butoxycarbonyl)-4-(methoxyimino)-2-pyrrolidine-carboxylic acid (Intermediate 2), ethyl amino(hydroxyimino)ethanoate (Intermediate 7) and [1,1'-biphenyl]-4-carboxylic acid, the title compound was isolated, after flash-chromatography, as a mixture of E-/Z-isomers as an oil in 35% yield (96.1% purity by HPLC).

¹H NMR (300 MHz, CDCl₃): 1.35 (t, 3H), 2.9–3.3 (m, 2H), 3.8 (m, 3H), 4.2–4.60 (m, 4H), 6.01 (s, 1H), 7.25–7.60 (m, 9H); MS(ESI+): 435.3.

Example 58

5-[(2S,4EZ)-1-([1,1'-biphenyl]-4-ylcarbonyl)-4-(methoxyimino)pyrrolidinyl]-N-[3-(dimethylamino)propyl]-1,2,4-oxadiazole-3-carboxamide

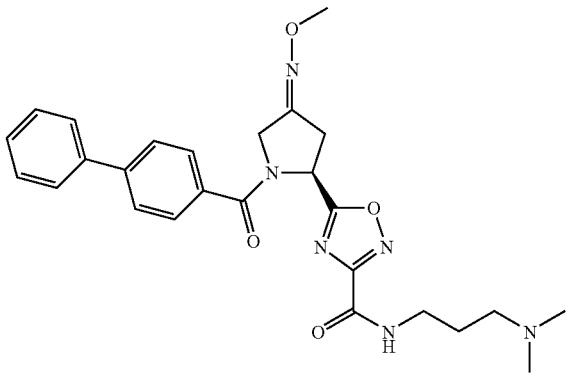

Ethyl 5-[(2S,4EZ)-1-([1,1'-biphenyl]-4-ylcarbonyl)-4-(methoxyimino)pyrrolidinyl]-1,2,4-oxadiazole-3-carboxylate (187 mg, 0.43 mmol, Example 57) was dissolved in 3:1 THF:water (10 mL) and stirred. LiOH (20 mg, 0.47 mmol, 1.1 eq) was added and the mixture stirred for 2 hours at room temperature. THF was removed in vacuo, the residue diluted in water and the solution acidified with 6N HCl (2 drops, pH=5). The aqueous phase was extracted with DCM (2×10 mL). The organic phase was dried with magnesium sulfate and the solvent removed in vacuo to give the acid derivative (165 mg, 94%) as a yellow oil. This crude intermediate (102 mg, 0.25 mmol) was dissolved in DCM (5 mL) and cooled to 0° C. EDC.HCl (53 mg, 0.28 mmol, 1.1 eq) was added in one portion and the mixture stirred for 10 minutes. N',N'-dimethyl-1,3-propanediamine (35 mg, 0.28 mmol, 1.1 eq) was added and the solution stirred at room temperature overnight. The mixture was then washed with 10% aqueous citric acid (2×5 mL). The separation was not good due to the partial solubility of the compound in water. Organic solvent was removed in vacuo and the residue was purified by semi-prep-LC to give the title compound in 56% yield (93% purity by HPLC).

¹H NMR (300 MHz, CDCl₃): 2.0–2.1 (m, 2H), 2.8 (s, 6H), 2.9–3.3 (m, 4H), 3.5 (m, 2H), 3.8 (m, 3H), 4.2–4.60 (m, 4H), 5.9 (s, 1H), 7.25–7.65 (m, 9H), 7.8 (m, 1H); MS(ESI+): 491.4.

Example 59

General Procedure for the Solid-Phase Synthesis of Pyrrolidine Oxadiazole Derivatives of General Formula I, with B Being a Substituent of Formula IIa (see Scheme 13)

a) Loading Step

A solution of (2S,4EZ)-1-(tert-butoxycarbonyl)-4-(methoxyimino)-2-pyrrolidine-carboxylic acid (Intermediate 2, 26 g, 100 mmol) in dry DCM (150 ml) was added to Kaiser oxime resin (34.97 g, 50 mmol) which was suspended in dry DCM (200 ml). Diisopropylcarbodiimide (7.83 ml, 50 mmol) was then added to the suspension and shaken overnight at ambient temperatures. The resin was then filtered at the pump and washed sequentially with DMF, DCM and finally diethyl ether before drying at 40° C. in vacuo.

b) N-deprotection Step

The resin obtained in the loading step was shaken with a 20% solution of trifluoroacetic acid in dichloromethane (200 ml) for 30 minutes prior to filtering at the pump and washing sequentially with aliquots of DMF, DCM and finally diethyl ether before drying at room temperature in vacuo.

c) N-capping Step

The resin from the previous step was transferred into a 96-well filter-plate (approx. 50 mg of dry resin/well) and each well treated with an N-reactive derivatising agent, e.g. with either of the following solutions:
a) an acid chloride (0.165 mmol) and diisopropylethylamine (0.165 mmol) in dry dichloromethane (1 ml), overnight
b) an acid (0.165 mmol) and DIC (0.165 mmol) in, depending on the solubility of the carboxylic acid, dry dichloromethane or NMP (1 ml) overnight
c) an isocyanate (0.165 mmol) in dry THF (1 ml), overnight
d) a sulfonyl chloride (0.165 mmol) and diisopropylethylamine (0.165 mmol) in NMP (1 ml), overnight.
e) a benzyl (alkyl) bromide (0.165 mmol) and diisopropylethylamine (0.165 mmol) in NMP (1 ml), overnight.

The plate was then sealed and shaken overnight at ambient temperature. The resins were then filtered, washing the resin sequentially with aliquots of DMF, DCM and finally diethyl ether before drying at room temperature in vacuo.

d) Cleavage Step

The amidoxime component (e.g., Intermediates 7, 0.27 mmol) was added to suspensions of the functionalised oxime resin batches from the previous step (50 mg, 0.05 mmol) in DCM (0.5–1 ml), the plates sealed and shaken over the weekend period (~66 hours) at ambient temperatures. After filtration, the resultant solvent was evaporated in vacuo. Pyridine (0.5–1 ml) was added to the residue and the solution was refluxed overnight. After cooling to ambient temperature, the solution was evaporated in vacuo and the residues re-dissolved in DCM (0.5–1 ml). After a wash with 2×0.5–1 ml 1M HCl$_{(aq)}$, the solutions were dried over magnesium sulphate and evaporated in vacuo to give the crude products, which were analyzed by HPLC and mass spectroscopy. In cases where an N-Boc-protecting group was present on the oxadiazole substituent (e.g. Examples 40, 46–48), a solution of 25% TFA in DCM (3 ml) was added to the crude compound (typically 0.15 mmol) and stirred at ambient temperatures for 40 min. The solvent was then removed in vacuo to give the N-deprotected products.

Example 60

(3EZ,5S)-5-(3-benzyl-1,2,4-oxadiazol-5-yl)-1-([1,1'-biphenyl]-4-ylcarbonyl)-3-pyrrolidinone O-methyloxime

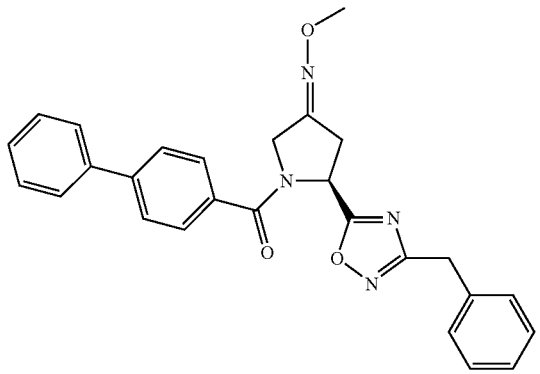

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxy-2-phenylethanimidamide, the title compound was obtained in 86% purity by HPLC. MS(ESI⁺): m/z=453.2.

Example 61

(3EZ,5S)-1-([1,1'-biphenyl]-4-ylcarbonyl)-5-(3-{[(2-furylmethyl)sulfanyl]methyl}-1,2,4-oxadiazol-5-yl)-3-pyrrolidinone O-methyloxime

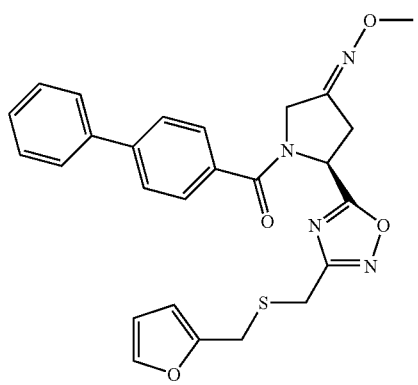

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and 2-[(2-furylmethyl)sulfanyl]-N'-hydroxyethanimidamide, the title compound was obtained in 53% purity by HPLC. MS(ESI⁺): m/z=489.6.

Example 62

(3EZ,5S)-1-([1,1'-biphenyl]-4-ylcarbonyl)-5-{3-[2-oxo-2-(1-pyrrolidinyl)ethyl]-1,2,4-oxadiazol-5-yl}-3-pyrrolidinone O-methyloxime

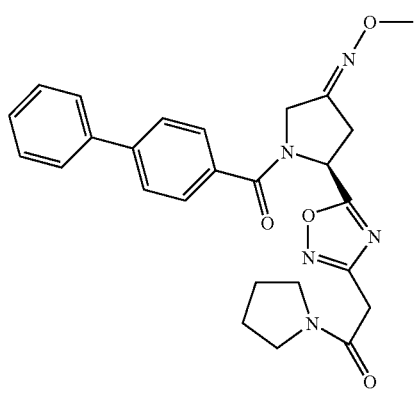

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and (1Z)-N'-hydroxy-3-oxo-3-(1-pyrrolidinyl)propanimidamide, the title compound was obtained in 89% purity by HPLC.
MS(ESI⁺): m/z=474.2.

Example 63

(3EZ,5S)-1-([1,1'-biphenyl]-4-ylcarbonyl)-5-{3-[(2-pyridinysulfanyl)methyl]-1,2,4-oxadiazol-5-yl}-3-pyrrolidinone O-methyloxime

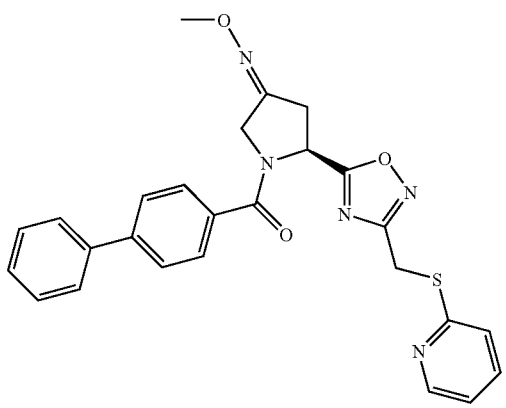

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxy-2-(2-pyridinylsulfanyl) ethanimidamide, the title compound was obtained in 66% purity by HPLC. MS(ESI+): m/z=486.2.

Example 64

(3EZ,5S)-1-([1,1'-biphenyl]-4-ylcarbonyl)-5-[3-(4-fluorophenyl)-1,2,4-oxadiazol-5-yl]-3-pyrrolidinone O-methyloxime

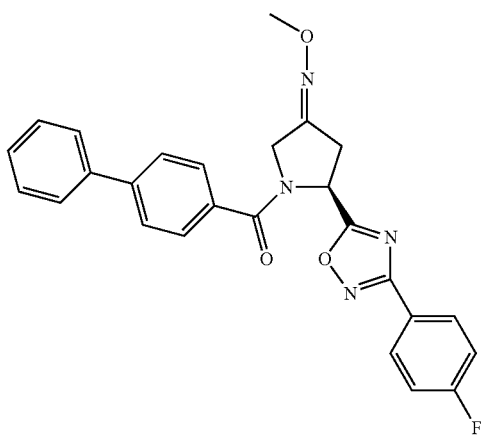

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and 4-fluoro-N'-hydroxybenzenecarboximidamide, the title compound was obtained in 79% purity by HPLC. MS(ESI+): m/z=457.2.

Example 65

(3EZ,5S)-1-([1,1'-biphenyl]-4-ylcarbonyl)-5-{3-[(2-thienylsulfanyl)methyl]-1,2,4-oxadiazol-5-yl}-3-pyrrolidinone O-methyloxime

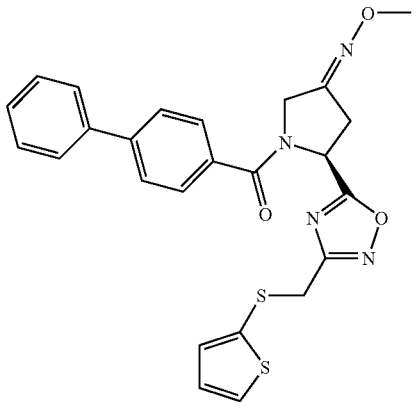

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxy-2-(2-thienylsulfanyl) ethanimidamide, the title compound was obtained in 81% purity by HPLC. MS(ESI+): m/z=491.4.

Example 66

(3EZ,5S)-1-([1,1'-biphenyl]-4-ylcarbonyl)-5-{3-[2-(3,5-dimethyl-1H-pyrazol-1-yl)ethyl]-1,2,4-oxadiazol-5-yl}-3-pyrrolidinone O-methyloxime

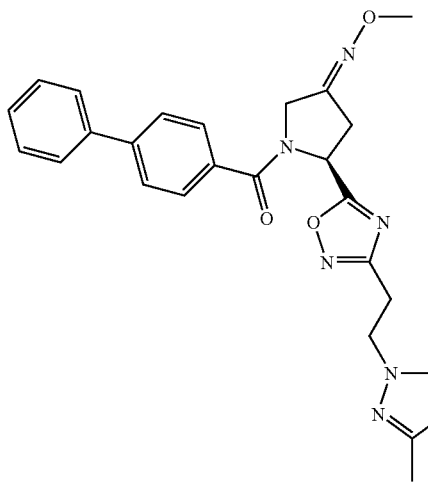

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and 3-(3,5-dimethyl-1H-pyrazol-1-yl)-N'-hydroxy-propanimidamide, the title compound was obtained in 79% purity by HPLC. MS(ESI+): m/z=485.3.

Example 67

(3EZ,5S)-1-([1,1'-biphenyl]-4-ylcarbonyl)-5-{3-[(methylsulfonyl)methyl]-1,2,4-oxadiazol-5-yl}-3-pyrrolidinone O-methyloxime

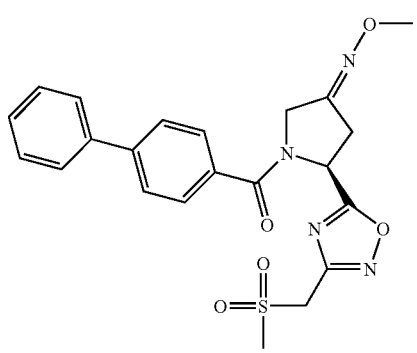

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N-hydroxy-2-(methylsulfonyl)ethanimidamide, the title compound was obtained in 87% purity by HPLC. MS(ESI$^+$): m/z=455.2.

Example 68

(3EZ,5S)-1-([1,1'-biphenyl]-4-ylcarbonyl)-5-[3-(5-methyl-3-isoxazolyl)-1,2,4-oxadiazol-5-yl]-3-pyrrolidinone O-methyloxime

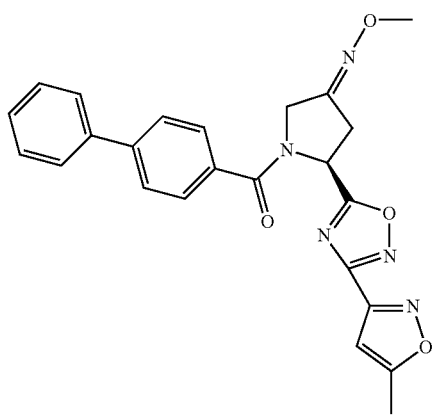

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxy-5-methyl-3-isoxazole-carboximidamide, the title compound was obtained in 78% purity by HPLC. MS(ESI$^+$): m/z=444.2.

Example 69

(3EZ,5S)-1-([1,1'-biphenyl]-4-ylcarbonyl)-5-[3-(2-thienylmethyl)-1,2,4-oxadiazol-5-yl]-3-pyrrolidinone O-methyloxime

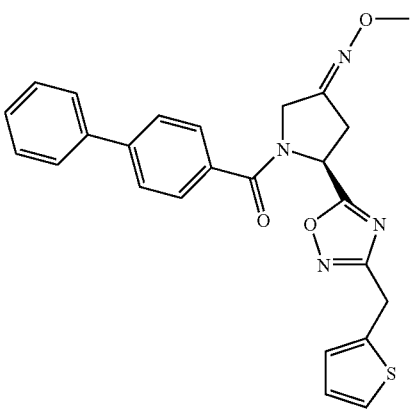

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxy-2-(2-thienyl)ethanimidamide, the title compound was obtained in 85% purity by HPLC. MS(ESI$^+$): m/z=459.2.

Example 70

(3EZ,5S)-1-([1,1'-biphenyl]-4-ylcarbonyl)-5-(3-phenyl-1,2,4-oxadiazol-5-yl)-3-pyrrolidinone O-methyloxime

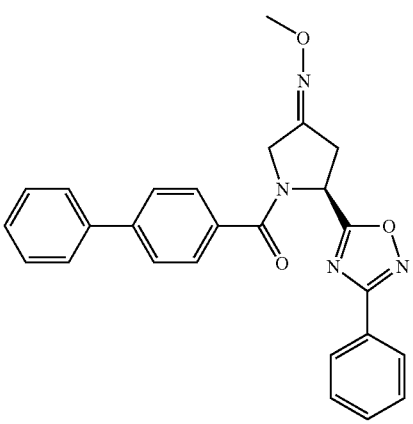

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N'-hydroxybenzenecarboximidamide, the title compound was obtained in 82% purity by TPLC. MS(ESI$^+$): m/z=439.2.

Example 71

(3EZ,5S)-([1,1'-biphenyl]-4-ylcarbonyl)-5-(3-{[(2-furylmethyl)sulfonyl]methyl}-1,2,4-oxadiazol-5-yl)-3-pyrrolidinone O-methyloxime

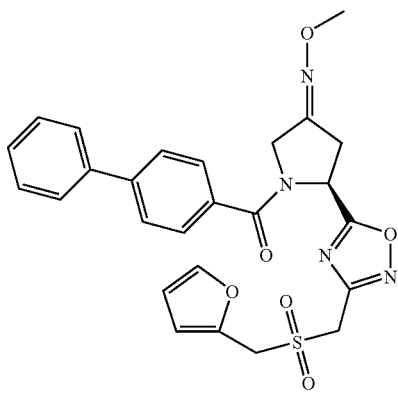

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and 2-[(2-furylmethyl)sulfonyl]-N'-hydroxy-ethanimidamide, the title compound was obtained in 88% purity by HPLC. MS(ESI$^+$): m/z=521.4.

Example 72

(3EZ,5S)-5-[3-(aminomethyl)-1,2,4-oxadiazol-5-yl]-1-([1,1'-biphenyl]-4-ylcarbonyl)-3-pyrrolidinone O-methyloxime

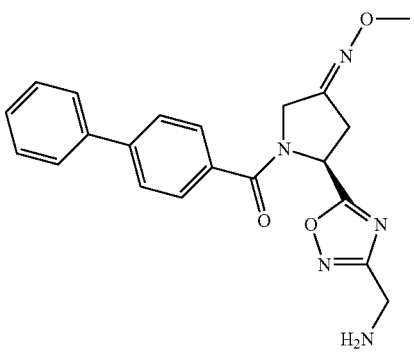

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and tert-butyl (2Z)-2-amino-2-(hydroxyimino)ethylcarbamate (an Intermediate 7), the title compound was obtained in 85% purity by HPLC. MS(ESI$^+$): m/z=392.0.

Example 73

(3EZ,5S)-1-([1,1'-biphenyl]-4-ylcarbonyl)-5-{3-[(RS)-hydroxy(phenyl)methyl]-1,2,4-oxadiazol-5-yl}-3-pyrrolidinone O-methyloxime

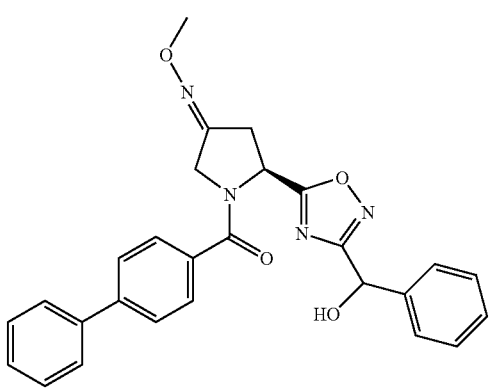

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and (2RS)-N',2-dihydroxy-2-phenylethanimidamide (an Intermediate 7), the title compound was obtained in 75% purity by HPLC. MS(ESI$^+$): m/z=469.3.

Example 74

(3EZ,5S)-1-([1,1'-biphenyl]-4-ylcarbonyl)-5-{3-[(1RS)-1-hydroxypropyl]-1,2,4-oxadiazol-5-yl}-3-pyrrolidinone O-methyloxime

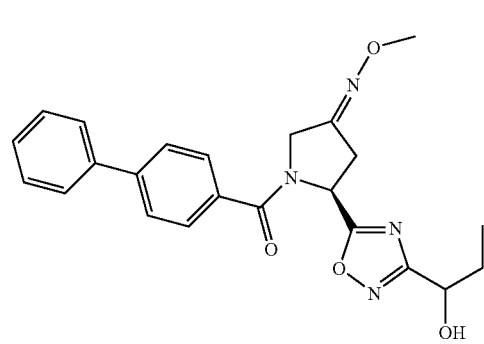

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and (2RS)-N',2-dihydroxybutanimidamide (an Intermediate 7), the title compound was obtained in 79% purity by HPLC. MS(ESI$^+$): m/z=421.2.

Example 75

(3EZ,5S)-1-([1,1'-biphenyl]-4-ylcarbonyl)-5-[3-hydroxymethyl)-1,2,4-oxadiazol-5-yl]-3-pyrrolidinone O-methyloxime

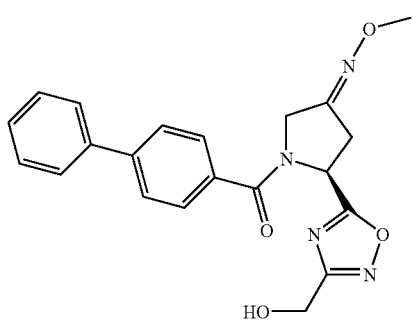

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and N',2-dihydroxyethanimidamide (an Intermediate 7), the title compound was obtained in 85% purity by HPLC. MS(ESI+): m/z=393.0.

Example 76

(3EZ,5S)-1-([1,1'-biphenyl]-4-ylcarbonyl)-5-{3-[(1S,2R)-2-hydroxycyclohexyl]-1,2,4-oxadiazol-5-yl}-3-pyrrolidinone O-methyloxime

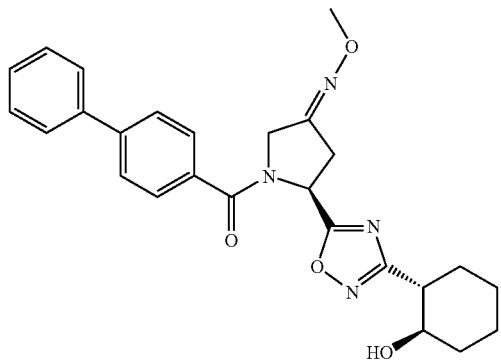

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and (1S,2R)-N',2-dihydroxycyclohexane-carboximidamide (an Intermediate 7), the title compound was obtained in 85% purity by HPLC. MS(ESI+): m/z=461.2.

Example 77

(3EZ,5S)-1-([1,1'-biphenyl]-4-ylcarbonyl)-5-{3-[(3RS)-piperidinyl]-1,2,4-oxadiazol-5-yl}-3-pyrrolidinone O-methyloxime

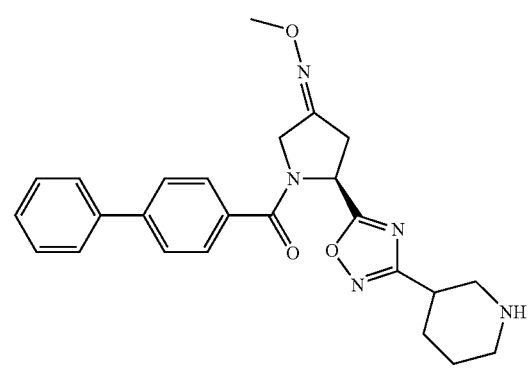

Following the general method as outlined in Example 59, starting from (2S,4EZ)-1-(tert-butoxycarbonyl)-4-(methoxyimino)-2-pyrrolidine-carboxylic acid (Intermediate 2), [1,1'-biphenyl]-4-carbonyl chloride, and tert-butyl (3RS)-3-[amino(hydroxyimino)methyl]-1-piperidinecarboxylate (an Intermediate 7), the title compound was obtained in 77% purity by HPLC. MS(ESI+): m/z=446.2.

Example 78

(3EZ,5S)-1-([1,1'-biphenyl]-4-ylcarbonyl)-5-{3-[(2RS)-piperidinyl]-1,2,4-oxadiazol-5-yl}-3-pyrrolidinone O-methyloxime

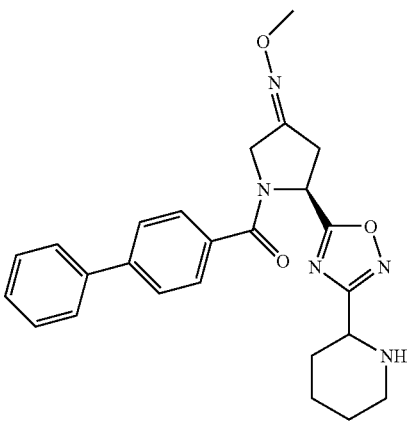

Following the general method as outlined in Example 59, starting from (2S,4EZ)-1-(tert-butoxycarbonyl)-4-(methoxyimino)-2-pyrrolidine-carboxylic acid (Inter-mediate 2), [1,1'-biphenyl]-4-carbonyl chloride, and tert-butyl (2RS)-2-[aminohydroxyimino)methyl]-1-piperidinecarboxylate (an Intermediate 7), the title compound was obtained in 78% purity by HPLC. MS(ESI+): m/z=446.2.

Example 79

General procedure for the solution-phase synthesis of pyrrolidine oxadiazole derivatives of general formula I, with B being a substituent of formula III, X=S (Schemes 9,11): (3EZ,5S)-1-([1,1'-biphenyl]-4-ylcarbonyl)-5-(5-thioxo-4,5-dihydro-1,3,4-oxadiazol-2-yl)-3-pyrrolidinone O-methyloxime

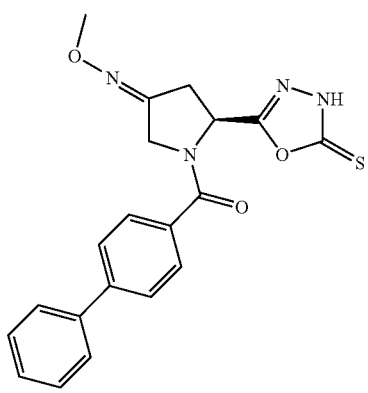

To a solution of tert-butyl (2S,4EZ)-2-(hydrazinocarbonyl)-4-(methoxyimino)-1-pyrrolidinecarboxylate (Intermediate 9, 2.86 mmoles; 780 mg) in ethanol (25 mL) at 0° C. was added carbon disulfide (6.86 mmoles; 522 mg) and potassium hydroxide (3 mmoles; 168 mg). The mixture was refluxed for 7 h. The solvent was evaporated and the residue re-dissolved in EtOAc and washed with NH$_4$Cl sat and 10% NaHCO$_3$ and brine. The organic layer was dried over Na$_2$SO$_4$ and evaporated to give the desired N-protected intermediate, tert-butyl (2S,4EZ)-4-(methoxyimino)-2-(5-thioxo-4,5-dihydro-1,3,4-oxadiazol-2-yl)-1-pyrrolidine-carboxylate, as a yellowish oil (200 mg, 23%).

$^1$H-NMR (CDCl$_3$): 1.46 (m, 9H, CH3), 2.7–3.3 (m, 2H, CH2), 3.88 (s, 3H, CH3-O), 4.05–4.35 (m, 2H, CH2), 5.29 (m, 1H, CH—N). MS(APCI$^-$): 313.0.

The N-protected intermediate from the previous step, tert-butyl (2S,4EZ)-1-(methoxyimino)-2-(5-thioxo-4,5-dihydro-1,3,4-oxadiazol-2-yl)-1-pyrrolidinecarboxylate (0.64 mmoles; 200 mg), was dissolved in dry DCM (25 mL) at 0° C. and HCl gas was bubbled into the solution for 20 min. The solvent was evaporated and the residue re-dissolved in DCM and evaporated. The residue was again re-dissolved in dried DCM (20 mL) and triethylamine (5.12 mmoles; 518 mg) was added, followed by slow addition of the N-capping agent, e.g. of [1,1'-biphenyl]-4-carbonyl chloride (0.64 mmoles; 139 mg), previously dissolved in DCM at 0° C.; the reaction mixture was stirred at r.t. overnight. To the mixture was then added 200 mg of Pol-trisamine (3.45 mmol/g) to scavenge the acyl chloride and the reaction was agitated for an additional 5 h, then filtered and the filtrate was washed with NH$_4$Clsat and brine, dried over Na$_2$SO$_4$ and the solvent evaporated The crude product was purified by FC using a linear gradient 40:60 (EtOAc:Cyclohexane) to 90:10 (EtOAc:MeOH) on the flash master for 37 minutes, to afford the title compound, (3EZ,5S)-1-([1,1'-biphenyl]-4-ylcarbonyl)-5-(5-thioxo-4,5-dihydro-1,3,4-oxadiazol-2-yl)-3-pyrrolidinone O-methyloxime (40 mg, 16%).

$^1$H-NMR (CDCl$_3$): 2.8–3.2 (m, 2H, CH2), 3.9 (s, 3H, CH3-O), 4.2–4.5 (m, 2H, CH2), 5.95 (m, 1H, CH—N), 7.3–7.7 (m, 9H, Ar). MS(APCI$^+$): 395.0; MS(APCI$^-$): 393.0.

Example 80

General procedure for the solution-phase synthesis of pyrrolidine oxadiazole derivatives of general formula I, with B=III, X=O (Schemes 9,11): 5-[(2S,4EZ)-1-([1,1'-biphenyl]-4-ylcarbonyl)-4-(methoxyimino)pyrrolidinyl]-1,3,4-oxadiazol-2(3H)-one

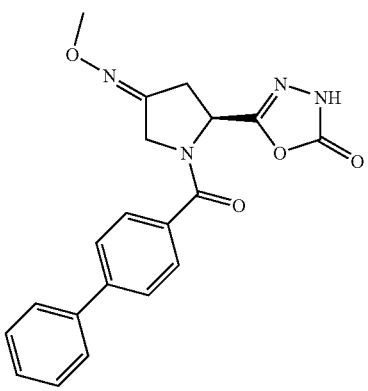

To a stirring solution of tert-butyl (2S,4EZ)-2-(hydrazinocarbonyl)-4-(methoxyimino)-1-pyrrolidinecarboxylate (Intermediate 9, 1.84 mmoles; 500 mg) and triethylamine (2.76 mmoles; 27 mg) in THF (25 mL) at 0° C. was added 1,1'-carbonyldiimidazole (2.76 mmoles, 448 mg). The stirring was continued for 5 hours. Another portion of triethylamine and 1,1'-carbonyldiimidazole were added and stirring was continued at room temperature overnight. The solvent was evaporated and the residue was dissolved in EtOAc and washed with NH$_4$Clsat., and 10% NaHCO$_3$, and brine. The organic layer was dried over Na$_2$SO$_4$ and evaporated to dryness to give the desired N-protected intermediate, tert-butyl (2S,4E)-4-(methoxyimino)-2-(5-oxo-4,5-dihydro-1,3,4-oxadiazol-2-yl)-1-pyrrolidinecarboxylate, as a white foam (460 mg, 84%).

$^1$H-NMR (CDCl$_3$): 1.46 (s, 9H, CH3), 2.8–3.25 (m, 2H, CH2), 3.88 (s, 3H, CH3-O), 4.05–4.35 (m, 2H, CH2), 5.06 (m, 1H, CH—N). MS(APCI$^-$): 297.0.

The N-protected intermediate from the previous step, tert-butyl (2S,4E)-4-(methoxyimino)-2-(5-oxo-4,5-dihydro-1,3,4-oxadiazol-2-yl)-1-pyrrolidinecarboxylate was subjected to identical conditions for N-deprotection and subsequent N-acylation, as described in Example 49, affording, after flash-chromatographic purification, the title compound, (5-[(2S,4EZ)-1-([1,1'-biphenyl]-4-ylcarbonyl)-4-(methoxyimino)-pyrrolidinyl]-1,3,4-oxadiazol-2(3H)-one (130 mg, 26%).

$^1$H-NMR (CDCl$_3$): 2.8–3.1 (m, 2H, CH2), 3.84 (s, 3H, CH3-O), 4.2–4.5 (m, 2H, CH2), 5.75 (m, 1H, CH—N), 7.35–7.7 (m, 9H, Ar). MS(APCI$^+$): 379.0; MS(APCI$^-$): 377.0.

Example 81

General procedure for the solution-phase synthesis of pyrrolidine oxadiazole derivatives of general formula I, with B being a substituent of formula IV, X=bond, $R^8$=H (Schemes 9,11): (3EZ,5S)-1-([1,1'-biphenyl]-4-ylcarbonyl)-5-(1,3,4-oxadiazol-2-yl)-3-pyrrolidinone O-methyloxime

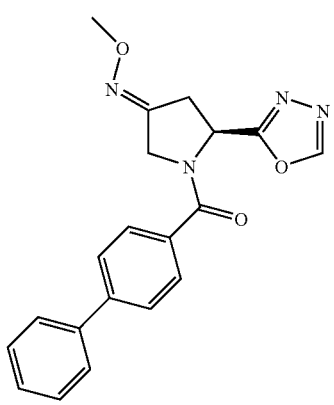

To a solution of tert-butyl (2S,4EZ)-2-(hydrazinocarbonyl)-4-(methoxyimino)-1-pyrrolidinecarboxylate (Intermediate 9, 2.86 mmoles; 780 mg) in TMOF (8 mL) were added 3 drops of acetic acid, and the reaction mixture was heated to 80° C. for 4 h, then at room temperature overnight. The solvent was evaporated to dryness to give a yellowish foam (610 mg). The residue was redissolved in toluene and $P_2O_5$ was added. The reaction mixture was heated to reflux for 2.5 h, after which time the solvent was evaporated. To the residue was added water, and the solution was extracted with EtOAc. The organic layer was washed with $NH_4Cl$sat and brine to give the desired N-protected intermediate, tert-butyl (2S,4E)-4-(methoxyimino)-2-(1,3,4-oxadiazol-2-yl)-1-pyrrolidinecarboxylate, as a yellow oil (330 mg, 63%). $^1$H-NMR-analysis revealed that the product was present in >90% purity. The compound was considered pure enough to be used for the subsequent steps without further purification (only 2 spots on TLC, Pancaldi revealation, corresponding to the E- and Z-isomers, $R_f$=0.35 and 0.47, eluting with EtOAc:Hexane 1:1).

$^1$H-NMR (CDCl$_3$): 1.46 (broad m, 9H, CH3), 2.8–3.3 (m, 2H, CH2), 3.89 (s, 3H, CH3-O), 4.05–4.3 (m, 2H, CH2), 5.4 (m, 1H, CH—N). MS(APCI$^+$): 283.0.

The N-protected intermediate from the previous step, tert-butyl (2S,4E)-4-(methoxyimino)-2-(1,3,4-oxadiazol-2-yl)-1-pyrrolidinecarboxylate was subjected to identical conditions for N-deprotection and subsequent N-acylation, as described in Example 49, affording, after flash-chromatographic purification, the title compound, (3EZ,5S)-1-([1,1'-biphenyl]-4-ylcarbonyl)-5-(1,3,4-oxadiazol-2-yl)-3-pyrrolidinone O-methyloxime (80 mg, 10%).

$^1$H-NMR (CDCl$_3$): 2.8–3.2 (m, 2H, CH2), 3.65 (s, 3H, CH3-O), 4.2–4.45 (m, 2H, CH2), 5.95 (m, 1H, CH—N), 7.3–7.6 (m, 9H, Ar), 8.2 (s, 1H, CH hetero). MS(APCI$^+$): 363.4.

Example 82

General procedure for the solution-phase synthesis of pyrrolidine oxadiazole derivatives of general formula I, with B being a substituent of formula IIb, $R^7$=H: (3EZ,5S)-1-([1,1'-biphenyl]-4-ylcarbonyl)-5-(1,2,4-oxadiazol-3-yl)-3-pyrrolidinone O-methyloxime

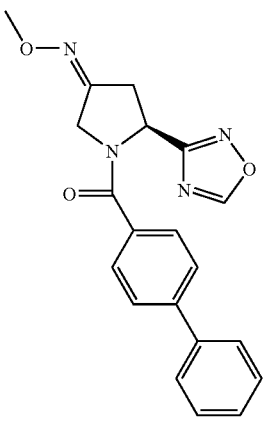

To a suspension of (2S,4EZ)-1-([1,1'-biphenyl]-4-ylcarbonyl)-N'-hydroxy-4-(methoxyimino)-2-pyrrolidinecarboximidamide (Intermediate 8, 170 mg, 0.48 mmol) in TMOF (20 ml), a catalytic amount of p-toluenesulfonic acid was added and the reaction mixture was heated to reflux for 16 h. TMOF was then evaporated in vacuo and the residue dissolved in DCM (15 mls). This was washed with NaHCO$_3$ (aq) (2×15 ml), dried over MgSO$_4$ and evaporated in vacuo. Silica gel chromatography eluting with 15% EtOAc in hexanes gave the desired product, (3EZ,5S)-1-([1,1'-biphenyl]-4-ylcarbonyl)-5-(1,2,4-oxadiazol-3-yl)-3-pyrrolidinone O-methyloxime (59 mg).

$^1$H-NMR (400 MHz, CDCl$_3$): 2.9 (m, 1H), 3.2 (m, 1H), 3.9 (m, 3H), 4.3–4.6 (m, 2H), 6.1 (m, 1H), 7.3–7.7 (m, 9H), 8.7 (s, 1H). MS(APCI$^+$): 363.2.

Example 83

Preparation of a Pharmaceutical Formulation

Formulation 1—Tablets

A pyrrolidine oxadiazole compound of formula I is admixed as a dry powder with a dry gelatin binder in an approximate 11:2 weight ration. A minor amount of magnesium stearate is added as a lubricant. The mixture is formed into 240–270 mg tablets (80–90 mg of active pyrrolidine oxadiazole compound per tablet) in a tablet press.

Formulation 2—Capsules

A pyrrolidine oxadiazole compound of formula I is admixed as a dry powder with a starch diluent in an approximate 1:1 weight ratio. The mixture is filled into 250 mg capsules (125 mg of active pyrrolidine oxadiazole compound per capsule).

Formulation 3—Liquid

A pyrrolidine oxadiazole compound of formula I, sucrose and xanthan gum are blended, passed through a No. 10 mesh U.S. sieve, and then mixed with a previously prepared solution of microcrystalline cellulose and sodium carboxymethyl cellulose (11:89) in water. Sodium benzoate, flavor, and color are diluted with water and added with stirring. Sufficient water is then added.

Formulation 4—Tablets

A pyrrolidine oxadiazole compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active pyrrolidine oxadiazole compound) in a tablet press.

Formulation 5—Injection

A pyrrolidine oxadiazole compound of formula I is dissolved in a buffered sterile saline injectable aqueous medium to provide a satisfactory concentration.

Example 84

Biological Assays

The compounds according to formula I may be subjected to the following assays:

a) In Vitro Competition Binding Assay with Scintillating Proximity Assay (Pharmaceutical Manufacturing International, 1992, p. 49–53 by Cook, N. D. et al)

This assays allows to determine the affinity of the test compounds for the OT receptor. Membranes from HEK293EBNA cells expressing the hOT receptor were resuspended in buffer containing 50 mM Tris-HCl, pH 7.4, 5 mM MgCl2 and 0.1% BSA (w/v). The membranes (2–4 μg) were mixed with 0.1 mg wheat-germ aglutinin (WGA) SPA bead (type A) and 0.2 nM of the radiolabel [$^{125}$I]-OVTA (OVTA being Ornithin Vasoactive and is an analogue of OT for competition binding experiments). Non-specific binding was determined in the presence of 1 μM Oxytocin. The total assay volume was 100 μl. The plates (Corning® NBS plate) were incubated at room temperature for 30 min and counted on a Mibrobeta plate counter. The tests compounds were used in concentrations of 30 μM, 10 μM, 1 μM, 300 nM, 100 nM, 10 nM, 1 nM, 100 pM, 10 pM. The competition binding data were analysed using the iterative, non-linear, curve-fitting program, "Prism".

The binding affinities to the oxytocin receptor of the pyrrolidine derivatives claimed in the formula I were assessed using the above described in vitro biological assay. Representative values for some example compounds are given in Table I below. The values refer to the binding affinity (IC$_{50}$; μM) of the example compounds according to formula I to the Oxytocin receptor.

TABLE 1

| Structure | IUPAC-Name | Binding affinity human OT-R IC$_{50}$ (μM) |
|---|---|---|
| 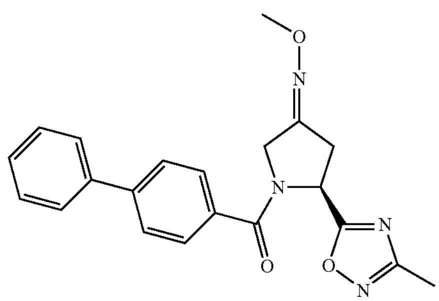 | (3EZ,5S)-1-([1,1'-biphenyl]-4-ylcarbonyl)-5-(3-methyl-1,2,4-oxadiazol-5-yl)-3-pyrrolidinone O-methyloxime | 0.088 |
| 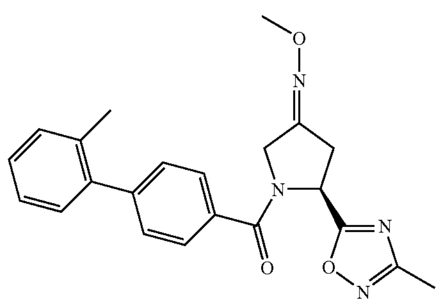 | (3EZ,5S)-1-[(2'-methyl[1,1'-biphenyl]-4-yl)carbonyl]-5-(3-methyl-1,2,4-oxadiazol-5-yl)-3-pyrrolidinone O-methyloxime | 0.021 |

TABLE 1-continued

| Structure | IUPAC-Name | Binding affinity human OT-R IC$_{50}$ (μM) |
|---|---|---|
| | (3EZ,5S)-1-([1,1'-biphenyl]-4-ylcarbonyl)-5-(1,3,4-oxa-diazol-2-yl)-3-pyrrolidinone O-methyl-oxime | 0.211 |
| | (3E,5S)-1-[(2'-methyl[1,1'-biphenyl]-4-yl)car-bonyl]-5-(3-methyl-1,2,4-oxadiazol-5-yl)-3-pyr-rolidinone O-methyloxime | 0.023 |
| | (3Z,5S)-1-[(2'-methyl[1,1'-biphenyl]-4-yl)car-bonyl]-5-(3-methyl-1,2,4-oxadiazol-5-yl)-3-pyr-rolidinone O-methyloxime | 0.009 |
| | (3EZ,5S)-1-([1,1'-biphenyl]-4-ylcarbonyl)-5-{3-[(1RS)-1-hy-droxypropyl]-1,2,4-oxadiazol-5-yl}-3-pyr-rolidinone O-methyloxime | 0.006 |

TABLE 1-continued

| Structure | IUPAC-Name | Binding affinity human OT-R IC$_{50}$ (μM) |
|---|---|---|
| | (3EZ,5S)-1-([1,1'-biphenyl]-4-ylcarbonyl)-5-{3-[2-oxo-2-(1-pyrrolidinyl)ethyl]-1,2,4-oxadiazol-5-yl}-3-pyrrolidinone O-methyloxime | 0.007 |
| 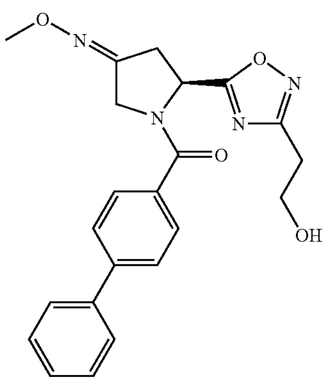 | (3EZ,5S)-1-([1,1'-biphenyl]-4-ylcarbonyl)-5-[3-(2-hydroxyethyl)-1,2,4-oxadiazol-5-yl]-3-pyrrolidinone O-methyloxime | 0.011 |
| 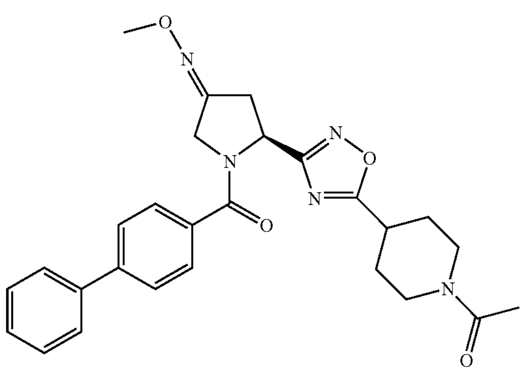 | (3EZ,5S)-5-[5-(1-acetyl-4-piperidinyl)-1,2,4-oxadiazol-3-yl]-1-([1,1'-biphenyl]-4-ylcarbonyl)-3-pyrrolidinone O-methyloxime | 0.002 |
| 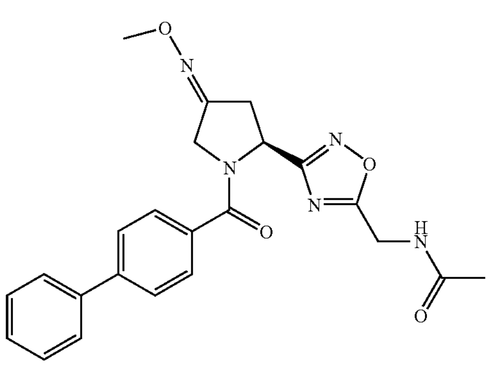 | N-({3-[(2S,4EZ)-1-([1,1'-biphenyl]-4-ylcarbonyl)-4-(methoxyimino)pyrrolidinyl]-1,2,4-oxadiazol-5-yl}methyl)acetamide | 0.003 |

According to a preferred embodiment, the compounds display binding affinities ($IC_{50}$ (μM)) of less 0.40 μM, more preferred of less than 0.1 μM.

b) Functional Assay No. 1: Inhibition of $Ca^{2+}$-mobilization by FLIPR (Fluorescent Imaging Plate Reader)

FLIPR is a machine for fluorescence imaging using a laser that is capable of illuminating a 96-well plate and a means of simultaneously reading each well thus enabling rapid measurements on a large number of samples.

This assay intends to show the inhibition of the OT/OT-R mediated calcium mobilisation—being necessary to cause uterine contractions—by using test compounds of formula (I).

Preparing the plates: FLIPR-plates were pre-coated with PLL (Poly-L-Lysine) 10 μg/ml+0.1% gelatine to attach the HEK (Human Embryonic Kidney) cells for 30 min up to 2 days at 37° C. The cells were plated out into 96-well plates (60000 cells/well).

Labelling with fluo-4: 50 μg fluo-4 (fluorescent marker) were dissolved in 20 μl pluronic acid (20% in DMSO). The dissolved fluo-4 was then diluted in 10 ml DMEM (Dubecco's Minimal Essential Medium-F12 medium without FCS (Fetal Calf Serum). The medium was removed from the plates, followed by one wash with DMEM-F12 medium.

Now, 100 μl of the DMEM-F12 medium containing fluo-4 were added and the cells incubated for 1–1.5 h (CHO-cells), and 1.5–2 h (HEK-cells). The cells now contain the fluorescent marker.

Buffer: 145 mM NaCl, 5 mM KCl, 1 mM $MgCl_2$, 10 mM Hepes, 10 mM Glucose, EGTA (Ethylene-bis oxyethylene nitrilo tetraacetic acid). Adjust to pH 7.4.

Performance of the assay: A minimum of 80 μl/well of antagonists (5×) in the above buffer (1×) were prepared (96-well plates). The antagonists were added to the wellplates at different concentrations (30 μM, 10 μM, 1 μM, 300 nM, 100 nM, 10 nM, 1 nM, 100 pM, 10 pM).

OT is added at a concentration of 40 nM.

The fluorescent market being sensitive to the amount of $Ca^{2+}$ mobilized within the cell may be quantified by the FLIPR machine.

The activities of the pyrrolidine derivatives according to formula I were assessed using the above described in vitro biological assay. Representative values for some example compounds are given in Table 2 below. The values refer to the capacity of the example compounds according to formula I to effectively antagonize oxytocin-induced intracellular $Ca^{2+}$-mobilization mediated by the Oxytocin receptor.

TABLE 2

| Structure | IUPAC-Name | Inhibition of $Ca^{2+}$ mobilization, hOT-R $IC_{50}$ (μM) |
|---|---|---|
| 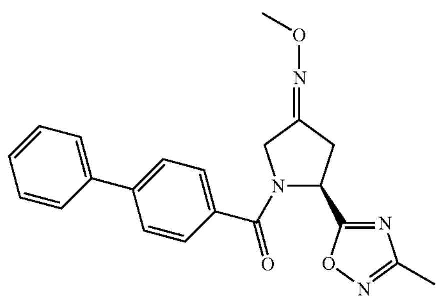 | (3EZ,5S)-1-([1,1'-biphenyl]-4-ylcarbonyl)-5-(3-methyl-1,2,4-oxadiazol-5-yl)-3-pyrrolidinone O-methyloxime | 0.004 |
| 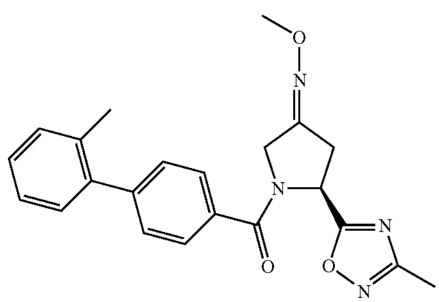 | (3EZ,5S)-1-[(2'-methyl[1,1'-biphenyl]-4-yl)carbonyl]-5-(3-methyl-1,2,4-oxadiazol-5-yl)-3-pyrrolidinone O-methyloxime | 0.012 |
| 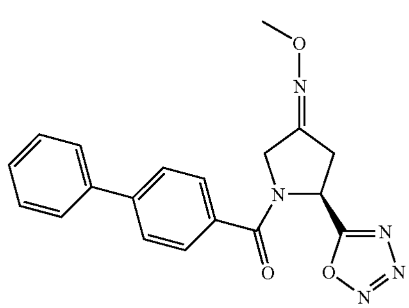 | (3EZ,5S)-1-([1,1'-biphenyl]-4-ylcarbonyl)-5-(1,3,4-oxadiazol-2-yl)-3-pyrrolidinone O-methyloxime | 0.220 |

TABLE 2-continued

| Structure | IUPAC-Name | Inhibition of Ca$^{2+}$ mobilization, hOT-R IC$_{50}$ (µM) |
|---|---|---|
| 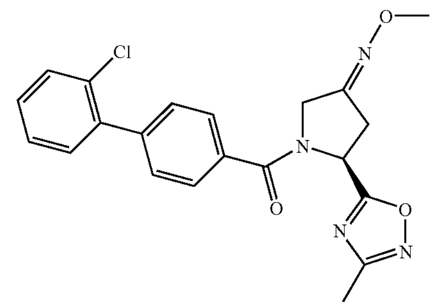 | (3EZ,5S)-1-[(2'-chloro[1,1'-biphenyl]-4-yl)carbonyl]-5-(3-methyl-1,2,4-oxadiazol-5-yl)-3-pyrrolidinone O-methyloxime | 0.001 |
| | (3Z,5S)-1-[(2'-methyl[1,1'-biphenyl]-4-yl)carbonyl]-5-(3-methyl-1,2,4-oxadiazol-5-yl)-3-pyrrolidinone O-methyloxime | 0.004 | c) Functional Assay No. 2: Inhibition of IP3 (Inositol Tri-Phosphate)-Synthesis in HEK/EBNA-OTR Cells This assay intends to show the inhibition of the OT/OT-R mediated IP3 synthesis—being necessary to cause uterine contractions—by using test compounds of formula (I).

Stimulation of the cells: HEK/EBNA OTR (rat or human) cells were plated out into costar 12-well plates, and equilibrated for 15–24 h with [$^3$H]-inositol radiolabel in medium without inositol supplement, with 1% FCS (0.5 ml/well). 4 µCi/ml were used. After this, the medium containing the label was aspirated. Then was added DMEM (without FCS, inositol), 20 mM Hepes (4-(2-hydroxyethyl)-1-piperazine-ethane-sulphonic acid), 1 mg/ml BSA containing 10 mM LiCl (freshly prepared), for 10–15 min at 37° C. The agonist (i.e. oxytocin used at a concentration of 10 nM) and the antagonists (i.e. the tests compounds of formula (I) used in a concentration of 10 µM, 1 µM, 300 nM, 100 nM, 10 nM, 1 nM, 100 pM, 10 pM, 3 pM) were added for the time required (15–45 min), followed by aspiration of the medium. Due to the antagonization of the OT receptor, the radiolabeled inositol is phosphorylated to yield IP3, the amount of the radiolabeled IP3 may be determined through the ensuing work-up. The reaction was stopped with 1 ml STOP-solution (i.e. 0.4 M perchloric acid), and let sit for 5–10 min at Room Temperature. Then, 0.8 ml were transferred into tubes containing 0.4 ml of neutralizing solution (0.72 M KOH/0.6M KHCO$_3$), and the tubes vortexed and kept in the cold at least for 2 h.

Separation of IP's: The samples were spun in a table top centrifuge at 3000–4000 rpm for 15 min. 1 ml of the supernatant was transferred to new tubes containing 2.5 ml H$_2$O. Packed resin (0.8 ml) was equilibrated with 20 ml H$_2$O, and the whole samples poured onto the chromatography columns, thus separating the mixture. To discard free inositol, two washes with 10 ml H$_2$O were carried out.

Elution of total IP's: The elution was achieved using 3 ml 1M ammonium formate/0.1M formic acid. The eluant was collected in scintillation counting tubes, followed by addition of 7 ml of scintillation liquid. The amount of IP3 is determined by a scintillating counter.

d) In Vivo Model for Inhibition of Uterine Contractions

The assay intends to show the biological effect of tested compounds in an in vivo model of preterm labor, premature birth.

Non-pregnant Charles River CD(SD) BR female rats (9–10 weeks old, 200–250 g) were treated at 18 and 24 hours before the experiment with 250 µg/kg, i.p. diethylstilbestrol (DES). For the assay, the animal was anaesthetised by urethane (1.75 g/kg, i.p.) and placed on an homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P231D Gould Statham pressure transducer, in, order to measure said pressure. For the i.v. route of administration of the test compounds, one jugular vein was isolated and cannulated with a PE60 tubing connected to a butterfly needle to allow the administration by a dispensing syringe. In the case of intraduodenal administration of the test compounds, the duodenum was isolated and similarly cannulated through a small incision in its wall. One carotid artery was also isolated and cannulated with PE60 catheter and connected to a suitable syringe for blood sample collection (see below). After a stabilization period, the same dose of oxytocin was repeatedly injected intravenously at 30-min intervals. When comparable contractile responses of the uterus to the selected dose of oxytocin were obtained, the test compound was administered at a concentration of 0.3; 1; 3; 10 mg/kg (5 ml/kg infusion; i.v) and 30 mg/kg (7.5 ml/kg infusion; iv), as well as concentrations of 3 and 10 mg/kg (5 ml/kg; per os), 30 mg/kg (7.5 ml/kg; per os) and also 60 mg/kg (10 ml/kg; per os.). Further injections of the same dose of oxytocin were then made for a suitable time after treatment to assess inhibitory effects of the compounds under study. The contractile response of the uterus to oxytocin was quantified by measuring the intrauterine pressure and the number of contractions.

A total of six animals is forming one group which is treated with a given test compound at a given concentration (see above).

The effect of the test compounds were evaluated by comparing pre- and post-treatment pressure values. In addition, at 2, 30, 90 and 210 minutes after test compound administration, a 0.5-ml blood sample was withdrawn from the cannulated carotid artery of each experimental animal. Plasma was obtained by standard laboratory procedure and the resulting samples were stored at −20° C.

The activities of the pyrrolidine derivatives claimed in the formula I were assessed using the above described in vivo biological assay. Representative values for one example compound are given in Table 3 below. The values refer to the capacity of the example compound according to formula I to effectively antagonize oxytocin-induced uterine contractions in the rat.

TABLE 3

| Structure | IUPAC-Name | Route of administration Vehicle | % Reduction of Uterine Contraction | Dose (mg/kg) |
|---|---|---|---|---|
| [structure] | (3Z,5S)-1-[(2'-methyl[1,1'-biphenyl]-4-yl)carbonyl]-5-(3-methyl-1,2,4-oxadiazol-5-yl)-3-pyrrolidinone O-methyloxime | Intravenous; NP3S 5 ml/kg infusion Intravenous; NP3S; 7.5 ml/kg infusion | −21.5 ± 7.3<br>−44.6 ± 7.1<br>−58.0 ±5.9<br>−67.2 ± 10.1<br>−80.3 ± 5.1 | 0.3<br>1<br>3<br>10<br>30 |
| [structure] | (3Z,5S)-1-([1,1'-biphenyl]-4-ylcarbonyl)-5-[3-(2-hydroxyethyl)-1,2,4-oxadiazol-5-yl]-3-pyrrolidinone O-methyloxime | subcutaneous; NP3S; 5 ml/kg | −13.2 ± 5.6<br>−30.2 ± 1.1<br>−39.7 ± 7.2<br>−57.5 ± 8.6 | 1<br>3<br>10<br>30 |
| [structure] | (3Z,5S)-1-([1,1'-biphenyl]-4-ylcarbonyl)-5-{5-[(dimethylamino)methyl]-1,2,4-oxadiazol-3-yl}-3-pyrrolidinone O-methyloxime | oral; NP3S; 5 ml/kg oral; NP3S; 6 ml/kg | −11.1 ± 1.3<br>−42.1 ± 2.9<br>−49.5 ± 6.1<br>−74.4 ± 4.2 | 1<br>3<br>10<br>30 |

The invention claimed is:

1. A compound according to formula I:

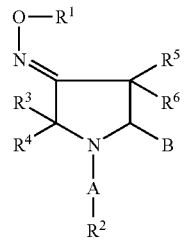

a geometrical isomer thereof, an optically active form thereof, an enantiomer thereof, a diastereomer thereof, a racemate thereof, or a pharmaceutically acceptable salt thereof, wherein:

A is selected from the group consisting of —(C=O)—, —(C=O)—O—, —SO$_2$—, —SO$_2$NH—, and —CH$_2$—;

B is an unsubstituted or substituted oxadiazole or unsubstituted or substituted thiadiazole ring;

R$^1$ is selected from the group consisting of C$_1$–C$_6$-alkyl, C$_2$–C$_6$-alkenyl, C$_2$–C$_6$-alkynyl, aryl, heteroaryl, C$_1$–C$_6$ alkyl aryl, and C$_1$–C$_6$ alkyl heteroaryl, wherein R$^1$ can form with the O atom to which it is attached a 3–8 membered, saturated or unsaturated heterocyclic ring which may contain 1–2 further heteroatoms selected from the group consisting of N, S and O and which is optionally fused with an aryl, heteroaryl or 3–8 membered saturated or unsaturated cycloalkyl ring;

R$^2$ is selected from the group consisting of C$_1$–C$_6$-alkyl, C$_2$–C$_6$-alkenyl, C$_2$–C$_6$-alkynyl, aryl, heteroaryl, heteroarylalkyl, 3–8-membered cycloalkyl, acyl, C$_1$–C$_6$-alkyl aryl, and C$_1$–C$_6$-alkyl heteroaryl, wherein said cycloalkyl or aryl or heteroaryl groups may be fused with 1–2 further cycloalkyl or aryl or heteroaryl groups;

R$^3$, R$^4$, R$^5$ and R$^6$ are independently selected from the group consisting of hydrogen, halogen, C$_1$–C$_6$-alkyl and C$_1$–C$_6$-alkoxy.

2. The compound according to claim 1, wherein R$^1$ is selected from the group consisting of H and a —C$_1$–C$_6$ alkyl group.

3. The compound according to claim 1, wherein A is —(C=O)—.

4. The compound according to claim 1, wherein R$^2$ is an aryl or a heteroaryl group.

5. The compound according to claim 4, wherein R$^2$ is a phenyl group.

6. The compound according to claim 5, wherein said phenyl group is substituted by a phenyl group.

7. The compound according to claim 1, wherein B is an oxadiazole of formula IIa or IIb:

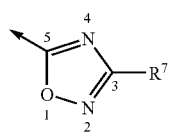

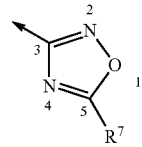

wherein R$^7$ is selected from the group comprising of hydrogen, sulfonyl, amino, C$_1$–C$_6$-alkyl, C$_2$–C$_6$-alkenyl, and C$_2$–C$_6$-alkynyl, wherein said alkyl, alkenyl, alkynyl chains may be interrupted by a heteroatom selected from N, O or S, aryl, heteroaryl, saturated 3–8-membered cycloalkyl, unsaturated 3–8-membered cycloalkyl, heterocycloalkyl, wherein said cycloalkyl, heterocycloalkyl, aryl or heteroaryl groups may be fused with 1–2 further cycloalkyl, heterocycloalkyl, aryl or heteroaryl group, an acyl moiety, C$_1$–C$_6$-alkyl aryl, C$_1$–C$_6$-alkyl heteroaryl, C$_1$–C$_6$-alkenyl aryl, C$_1$–C$_6$-alkenyl heteroaryl, C$_1$–C$_6$-alkynyl aryl, C$_1$–C$_6$-alkynyl heteroaryl, C$_1$–C$_6$-alkyl cycloalkyl, C$_1$–C$_6$-alkyl heterocycloalkyl, C$_1$–C$_6$-alkenyl cycloalkyl, C$_1$–C$_6$-alkenyl heterocycloalkyl, C$_1$–C$_6$-alkynyl cycloalkyl, C$_1$–C$_6$-alkynyl heterocycloalkyl, alkoxycarbonyl, aminocarbonyl, C$_1$–C$_6$-alkyl carboxy, C$_1$–C$_6$-alkyl acyl, aryl acyl, heteroaryl acyl, C$_3$–C$_8$-(hetero)cycloalkyl acyl, C$_1$–C$_6$-alkyl acyloxy, C$_1$–C$_6$-alkyl alkoxy, C$_1$–C$_6$-alkyl alkoxycarbonyl, C$_1$–C$_6$-alkyl aminocarbonyl, C$_1$–C$_6$-alkyl acylamino, acylamino, C$_1$–C$_6$-alkyl ureido, C$_1$–C$_6$-alkyl carbamate, C$_1$–C$_6$-alkyl amino, C$_1$–C$_6$-alkyl ammonium, C$_1$–C$_6$-alkyl sulfonyloxy, C$_1$–C$_6$-alkyl sulfonyl, C$_1$–C$_6$-alkyl sulfinyl, C$_1$–C$_6$-alkyl sulfanyl, C$_1$–C$_6$-alkyl sulfonylamino, C$_1$–C$_6$-alkyl aminosulfonyl, hydroxy and halogen.

8. The compound according to claim 7, wherein R$^7$ is selected from the group consisting of a sulfonyl moiety, an amino moiety, a C$_1$–C$_6$-alkyl group, C$_2$–C$_6$-alkenyl group, C$_2$–C$_6$-alkynyl group, aryl group, heteroaryl group, 3–8-membered cycloalkyl group, optionally containing at least one heteroatom selected from the group consisting of N, O, and S, C$_1$–C$_6$-alkyl aryl, C$_1$–C$_6$-alkyl heteroaryl, C$_1$–C$_6$-alkenyl aryl, C$_1$–C$_6$-alkenyl heteroaryl, alkoxycarbonyl, carboxylic amide, C$_1$–C$_6$-alkyl carbonyl, C$_1$–C$_6$-arylcarbonyl, C$_1$–C$_6$-heteroarylcarbonyl, and C$_4$–C$_8$-cycloalkylcarbonyl, said groups substituted by at least one sulfonyl moiety or amino moiety.

9. The compound according to claim 8, wherein R$^7$ is selected from the group consisting of a C$_1$–C$_6$-alkyl amino, heterocycloalkyl, C$_1$–C$_6$-alkyl heterocycloalkyl, aminocarbonyl, C$_1$–C$_6$-alkylamino carbonyl, C$_1$–C$_6$ alkyl acyl amino, C$_1$–C$_6$ alkyl sulfonyl and C$_1$–C$_6$-alkyl.

10. The compound according to claim 9, wherein R$^7$ is selected from the group consisting of dimethyl aminomethyl, 2-(dimethylamino)ethyl, 1-methyl-3-piperidinyl and 4-(acetyl-1-piperazinyl)methyl.

11. The compound according to claim 1, wherein B is an isoxadiazole of formula III or IV:

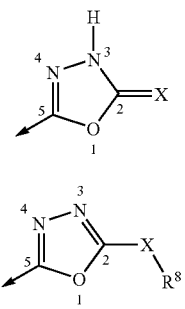

wherein X is O or S;

R⁸ is a hydrogen, C₁–C₆-alkyl, C₂–C₆-alkenyl, C₂–C₆-alkynyl, aryl, heteroaryl, saturated 3–8-membered cycloalkyl, unsaturated 3–8-membered cycloalkyl, optionally containing 1 to 3 heteroatoms selected from the group consisting of N, O and S, an acyl moiety, C₁–C₆-alkyl aryl, C₁–C₆-alkyl heteroaryl, C₁–C₆-alkenyl aryl, C₁–C₆-alkenyl heteroaryl, alkoxycarbonyl, carboxylic amide, C₁–C₆-alkoxy, aryloxy, heteroaryloxy, halogen, cyano, C₁–C₆-alkyl carbonyl, arylcarbonyl, of heteroarylcarbonyl, saturated C₄–C₈-cycloalkylcarbonyl, and unsaturated C₄–C₈-cycloalkylcarbonyl, wherein said cycloalkyl or aryl or heteroaryl groups may be fused with 1–2 further cycloalkyl or aryl or heteroaryl group and wherein said alkyl, alkenyl, alkynyl chain may be interrupted by an heteroatom selected from the group consisting of N, O and S.

12. The compound according to claim 1 wherein each of R³, R⁴, R⁵ and R⁶ is H.

13. The compound according to claim 1 wherein A is —(C═O)—, R¹ is a methyl group, R² is a biphenyl group, each of R³, R⁴, R⁵ and R⁶ is H and B is an oxadiazole ring of formulae IIa, IIb, III or IV.

14. The compound according to claim 13 wherein B is an oxadiazole ring of formula IIa or IIb.

15. The compound according to claim 1 selected from the group consisting of:

(3EZ,5S)-1-([1,1'-biphenyl]-4-ylcarbonyl)-5-(3-methyl-1,2,4-oxadiazol-5-yl)-3-pyrrolidinone O-methyloxime, (3EZ,5S)-1-[(2'-methyl[1,1'-biphenyl]-4-yl)carbonyl]-5-(3-methyl-1,2,4-oxadiazol-5-yl)-3-pyrrolidinone O-methyloxime, (3EZ,5S)-1-([1,1'-biphenyl]-4-ylcarbonyl)-5-(1,3,4-oxadiazol-2-yl)-3-pyrrolidinone O-methyloxime, (3EZ,5S)-1-([1,1'-biphenyl]-4-ylcarbonyl)-5-(3-methyl-1,2,4-oxadiazol-5-yl)-3-pyrrolidinone O-methyloxime, (3EZ,5S)-1-([1,1'-biphenyl]-4-ylcarbonyl)-5-(5-thioxo-4,5-dihydro-1,3,4-oxadiazol-2-yl)-3-pyrrolidinone O-methyloxime, (3EZ,5S)-5-(3-benzyl-1,2,4-oxadiazol-5-yl)-1-([1,1'-biphenyl]-4-ylcarbonyl)-3-pyrrolidinone O-methyloxime, (3EZ,5S)-1-([1,1'-biphenyl]-4-ylcarbonyl)-5-(3-{[(2-furylmethyl)sulfanyl]methyl}-1,2,4-oxadiazol-5-yl)-3-pyrrolidinone O-methyloxime, (3EZ,5S)-1-([1,1'-biphenyl]-4-ylcarbonyl)-5-{3-[2-oxo-2-(1-pyrrolidinyl)ethyl]-1,2,4-oxadiazol-5-yl}-3-pyrrolidinone O-methyloxime, (3EZ,5S)-1-([1,1'-biphenyl]-4-ylcarbonyl)-5-{3-[(2-pyridinylsulfanyl)methyl]-1,2,4-oxadiazol-5-yl}-3-pyrrolidinone O-methyloxime, (3EZ,5S)-1-([1,1'-biphenyl]-4-ylcarbonyl)-5-[3-(4-fluorophenyl)-1,2,4-oxadiazol-5-yl]-3-pyrrolidinone O-methyloxime, (3EZ,5S)-1-([1,1'-biphenyl]-4-ylcarbonyl)-5-{3-[(2-thienylsulfanyl)methyl]-1,2,4-oxadiazol-5-yl}-3-pyrrolidinone O-methyloxime, (3EZ,5S)-1-([1,1'-biphenyl]-4-ylcarbonyl)-5-{3-[2-(3,5-dimethyl-1H-pyrazol-1-yl)ethyl]-1,2,4-oxadiazol-5-yl}-3-pyrrolidinone O-methyloxime, (3EZ,5S)-1-([1,1'-biphenyl]-4-ylcarbonyl)-5-{3-[(methylsulfonyl)methyl]-1,2,4-oxadiazol-5-yl}-3-pyrrolidinone O-methyloxime, (3EZ,5S)-1-([1,1'-biphenyl]-4-ylcarbonyl)-5-[3-(5-methyl-3-isoxazolyl)-1,2,4-oxadiazol-5-yl]-3-pyrrolidinone O-methyloxime, (3EZ,5S)-1-([1,1'-biphenyl]-4-ylcarbonyl)-5-[3-(2-thienylmethyl)-1,2,4-oxadiazol-5-yl]-3-pyrrolidinone O-methyloxime, (3EZ,5S)-1-([1,1'-biphenyl]-4-ylcarbonyl)-5-(3-phenyl-1,2,4-oxadiazol-5-yl)-3-pyrrolidinone O-methyloxime, (3EZ,5S)-1-([1,1'-biphenyl]-4-ylcarbonyl)-5-(3-{[(2-furylmethyl)sulfonyl]methyl}-1,2,4-oxadiazol-5-yl)-3-pyrrolidinone O-methyloxime, (3EZ,5S)-5-[3-(aminomethyl)-1,2,4-oxadiazol-5-yl]-1-([1,1'-biphenyl]-4-ylcarbonyl)-3-pyrrolidinone O-methyloxime, (3EZ,5S)-1-([1,1'-biphenyl]-4-ylcarbonyl)-5-{3-[(RS)-hydroxy(phenyl)methyl]-1,2,4-oxadiazol-5-yl}-3-pyrrolidinone O-methyloxime, (3EZ,5S)-1-([1,1'-biphenyl]-4-ylcarbonyl)-5-{3-[(1RS)-1-hydroxypropyl]-1,2,4-oxadiazol-5-yl}-3-pyrrolidinone O-methyloxime, (3EZ,5S)-1-([1,1'-biphenyl]-4-ylcarbonyl)-5-[3-(hydroxymethyl)-1,2,4-oxadiazol-5-yl]-3-pyrrolidinone O-methyloxime, (3EZ,5S)-1-([1,1'-biphenyl]-4-ylcarbonyl)-5-{3-[(1S,2R)-2-hydroxycyclohexyl]-1,2,4-oxadiazol-5-yl}-3-pyrrolidinone O-methyloxime, (3EZ,5S)-1-([1,1'-biphenyl]-4-ylcarbonyl)-5-[3-(2-hydroxyethyl)-1,2,4-oxadiazol-5-yl]-3-pyrrolidinone O-methyloxime, (3EZ,5S)-1-([1,1'-biphenyl]-4-ylcarbonyl)-5-[3-(4-piperidinyl)-1,2,4-oxadiazol-5-yl]-3-pyrrolidinone O-methyloxime, (3EZ,5S)-1-([1,1'-biphenyl]-4-ylcarbonyl)-5-{3-[(3RS)-piperidinyl]-1,2,4-oxadiazol-5-yl}-3-pyrrolidinone O-methyloxime, (3EZ,5S)-1-([1,1'-biphenyl]-4-ylcarbonyl)-5-{3-[(2RS)-piperidinyl]-1,2,4-oxadiazol-5-yl}-3-pyrrolidinone O-methyloxime, (3EZ,5S)-1-[(2'-chloro[1,1'-biphenyl]-4-yl)carbonyl]-5-(3-methyl-1,2,4-oxadiazol-5-yl)-3-pyrrolidinone O-methyloxime, (3EZ,5S)-5-(3-methyl-1,2,4-oxadiazol-5-yl)-1-{[2'-(trifluoromethyl)[1,1'-biphenyl]-4-yl]carbonyl}-3-pyrrolidinone O-methyloxime, (3Z,5S)-1-[(2'-fluoro[1,1'-biphenyl]-4-yl)carbonyl]-5-(3-methyl-1,2,4-oxadiazol-5-yl)-3-pyrrolidinone O-methyloxime, (3EZ,5S)-1-[(4'-fluoro[1,1'-biphenyl]-4-yl)carbonyl]-5-(3-methyl-1,2,4-oxadiazol-5-yl)-3-pyrrolidinone O-methyloxime, (3EZ,5S)-1-([1,1'-biphenyl]-4-ylcarbonyl)-5-(1,2,4-oxadiazol-3-yl)-3-pyrrolidinone O-methyloxime, (3E,5S)-1-[(2'-fluoro[1,1'-biphenyl]-4-yl)carbonyl]-5-(3-methyl-1,2,4-oxadiazol-5-yl)-3-pyrrolidinone O-methyloxime, (3E,5S)-1-[(2'-methyl[1,1'-biphenyl]-4-yl)carbonyl]-5-(3-methyl-1,2,4-oxadiazol-5-yl)-3-pyrrolidinone O-methyloxime, (3Z,5S)-1-[(2'-methyl[1,1'-biphenyl]-4-yl)carbonyl]-5-(3-methyl-1,2,4-oxadiazol-5-yl)-3-pyrrolidinone O-methyloxime, (3EZ,5S)-1-([1,1'-biphenyl]-4-ylcarbonyl)-5-[5-(phenoxymethyl)-1,2,4-oxadiazol-3-yl]-3-pyrrolidinone O-methyloxime, (3EZ,5S)-1-([1,1'-biphenyl]-4-ylcarbonyl)-5-(5-phenyl-1,2,4-oxadiazol-3-yl)-3-pyrrolidinone O-methyloxime, N-({3-[(2S,4EZ)-1-([1,1'-biphenyl]-4-ylcarbonyl)-4-(methoxyimino)pyrrolidinyl]-1,2,4-oxadiazol-5-yl}methyl)acetamide, (3EZ,5S)-1-([1,1'-biphenyl]-4-ylcarbonyl)-5-{5-[4-(hydroxymethyl)phenyl]-1,2,4-oxadiazol-3-yl}-3-pyrrolidinone O-methyloxime, (3EZ,5S)-1-([1,1'-biphenyl]-4-ylcarbonyl)-5-[5-(2-hydroxyethyl)-1,2,4-oxadiazol-3-yl]-3-pyrrolidinone O-methyloxime, (3EZ,5S)-1-([1,1'-biphenyl]-4-ylcarbonyl)-5-{5-[(2S)-2-hydroxy-2-phenylethyl]-1,2,4-oxadiazol-3-yl}-3-pyrrolidinone O-methyloxime, {3-[(2S,4EZ)-1-([1,1'-biphenyl]-4-ylcarbonyl)-4-(methoxyimino)pyrrolidinyl]-1,2,4-oxadiazol-5-yl}methylformamide, (3EZ,5S)-1-([1,1'-biphenyl]-4-ylcarbonyl)-5-[5-(methoxymethyl)-1,2,4-oxadiazol-3-yl]-3-pyrrolidinone O-methyloxime, (3EZ,5S)-1-([1,1'-biphenyl]-4-ylcarbonyl)-5-[5-(2-phenoxyethyl)-1,2,4-oxadiazol-3-yl]-3-pyrrolidinone O-methyloxime, (3EZ,5S)-1-([1,1'-biphenyl]-4-ylcarbonyl)-5-[5-(2-methoxyethyl)-1,2,4-oxadiazol-3-yl]-3-pyrrolidinone O-methyloxime, (3EZ,5S)-5-[5-(1-acetyl-4-piperidinyl)-1,2,4-oxadiazol-3-yl]-1-([1,1'-biphenyl]-4-ylcarbonyl)-3-pyrrolidinone O-methyloxime, (3EZ,5S)-1-([1,1'-biphenyl]-4-ylcarbonyl)-5-[5-(2-pyridinyl)-1,2,4-oxadiazol-3-yl]-3-pyrrolidinone O-methyloxime, (3EZ,5S)-1-([1,1'-biphenyl]-4-ylcarbonyl)-5-[5-(3-thienyl)-1,2,4-oxadiazol-3-yl]-3-pyrrolidinone O-methyloxime, (3EZ,5S)-1-([1,1'-biphenyl]-4-ylcarbonyl)-5-(5-ethyl-1,2,4-oxadiazol-3-yl)-3-pyrrolidinone O-methyloxime, (3EZ,5S)-1-([1,1'-biphenyl]-4-ylcarbonyl)-5-(5-cyclopentyl-1,2,4-oxadiazol-3-yl)-3-pyrrolidinone O-methyloxime, (3EZ,5S)-1-([1,1'-biphenyl]-4-ylcarbonyl)-5-(5-methyl-1,2,4-oxadiazol-3-yl)-3-pyrrolidinone O-methyloxime, (3EZ,5S)-1-([1,1'-biphenyl]-4-ylcarbonyl)-5-{5-[(RS)-hydroxy(phenyl)methyl]-1,2,4-oxadiazol-3-yl}-3-pyrrolidinone O-methyloxime, (3EZ,5S)-1-([1,1'-biphenyl]-4-ylcarbonyl)-5-{5-[(1RS)-1-hydroxy-2-phenylethyl]-1,2,4-oxadiazol-3-yl}-3-pyrrolidinone O-methyloxime, (3EZ,5S)-1-([1,1'-biphenyl]-4-ylcarbonyl)-5-{5-[(1R)-1-(dimethylamino)-2-phenylethyl]-1,2,4-oxadiazol-3-yl}-3-pyrrolidinone O-methyloxime, (3EZ,5S)-1-([1,1'-biphenyl]-4-ylcarbonyl)-5-[5-(3-pyridinyl)-1,2,4-oxadiazol-3-yl]-3-pyrrolidinone O-methyloxime, (3EZ,5S)-1-([1,1'-biphenyl]-4-ylcarbonyl)-5-[5-(4-pyridinyl)-1,2,4-oxadiazol-3-yl]-3-pyrrolidinone O-methyloxime, (3Z,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime, (3EZ,5S)-5-[3-(1-acetyl-4-piperidinyl)-1,2,4-oxadiazol-5-yl]-1-([1,1'-biphenyl]-4-ylcarbonyl)-3-pyrrolidinone O-methyloxime, (3EZ,5S)-5-{5-[(4-acetyl-1-piperazinyl)methyl]-1,2,4-oxadiazol-3-yl}-1-([1,1'-biphenyl]-4-ylcarbonyl)-3-pyrrolidinone O-methyloxime, N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(1-piperidinyl)propanamide, (3EZ,5S)-1-([1,1'-biphenyl]-4-ylcarbonyl)-5-{5-[(3S)-1-methylpiperidinyl]-1,2,4-oxadiazol-3-yl}-3-pyrrolidinone O-methyloxime, (3EZ,5S)-1-([1,1'-biphenyl]-4-ylcarbonyl)-5-{5-[(3R)-1-methylpiperidinyl]-1,2,4-oxadiazol-3-yl}-3-pyrrolidinone O-methyloxime, (3EZ,5S)-1-([1,1'-biphenyl]-4-ylcarbonyl)-5-[5-(6-hydroxy-3-pyridinyl)-1,2,4-oxadiazol-3-yl]-3-pyrrolidinone O-methyloxime, (3Z,5S)-1-([1,1'-biphenyl]-4-ylcarbonyl)-5-{5-[(dimethylamino)methyl]-1,2,4-oxadiazol-3-yl}-3-pyrrolidinone O-methyloxime, (3EZ,5S)-5-{5-[(1S,2R)-1-amino-2-hydroxypropyl]-1,2,4-oxadiazol-3-yl}-1-([1,1'-biphenyl]-4-ylcarbonyl)-3-pyrrolidinone O-methyloxime, (3EZ,5S)-1-([1,1'-biphenyl]-4-ylcarbonyl)-5-{5-[(3S)-piperidinyl]-1,2,4-oxadiazol-3-yl}-3-pyrrolidinone O-methyloxime, (3EZ,5S)-1-([1,1'-biphenyl]-4-ylcarbonyl)-5-{5-[(3R)-piperidinyl]-1,2,4-oxadiazol-3-yl}-3-pyrrolidinone O-methyloxime, (3EZ,5RS)-1-([1,1'-biphenyl]-4-ylcarbonyl)-5-[5-(1-methyl-3-piperidinyl)-1,2,4-oxadiazol-3-yl]-3-pyrrolidinone O-methyloxime, tert-butyl (3R)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate, 4-({3-[(2S,4EZ)-1-([1,1'-biphenyl]-4-ylcarbonyl)-4-(methoxyimino)pyrrolidinyl]-1,2,4-oxadiazol-5-yl}methyl)-2,6-piperazinedione, (3Z,5S)-1-([1,1'-biphenyl]-4-ylcarbonyl)-5-[3-(2-hydroxyethyl)-1,2,4-oxadiazol-5-yl]-3-pyrrolidinone O-methyloxime, (3Z,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime, (3EZ,5S)-1-([1,1'-biphenyl]-4-ylcarbonyl)-5-[5-(1-methyl-4-piperidinyl)-1,2,4-oxadiazol-3-yl]-3-pyrrolidinone O-methyloxime, (3EZ,5S)-1-([1,1'-biphenyl]-4-ylcarbonyl)-5-{5-[(dimethylamino)methyl]-1,2,4-oxadiazol-3-yl}-3-pyrrolidinone O-methyloxime, (3EZ,5S)-1-([1,1'-biphenyl]-4-ylcarbonyl)-5-[3-(1-methyl-4-piperidinyl)-1,2,4-oxadiazol-5-yl]-3-pyrrolidinone O-methyloxime, (3EZ,5S)-5-{5-[(1S)-1-amino-2-hydroxyethyl]-1,2,4-oxadiazol-3-yl}-1-([1,1'-biphenyl]-4-ylcarbonyl)-3-pyrrolidinone O-methyloxime, 5-[(2S,4EZ)-1-([1,1'-biphenyl]-4-ylcarbonyl)-4-(methoxyimino)pyrrolidinyl]-N-[3-(dimethylamino)propyl]-1,2,4-oxadiazole-3-carboxamide, (3E,5S)-1-([1,1'-biphenyl]-4-ylcarbonyl)-5-{5-[(dimethylamino)methyl]-1,2,4-oxadiazol-3-yl}-3-pyrrolidinone O-methyloxime, tert-butyl (3S)-3-{3-[(2S,4EZ)-1-([1,1'-biphenyl]-4-ylcarbonyl)-4-(methoxyimino)pyrrolidinyl]-1,2,4-oxadiazol-5-yl}-1-piperidinecarboxylate, (3EZ,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime, (3Z,5S)-1-([1,1'-biphenyl]-4-ylcarbonyl)-5-{5-[(4-methyl-1-piperazinyl)methyl]-1,2,4-oxadiazol-3-yl}-3-pyrrolidinone O-methyloxime, ethyl 5-[(2S,4EZ)-1-([1,1'-biphenyl]-4-ylcarbonyl)-4-(methoxyimino)pyrrolidinyl]-1,2,4-oxadiazole-3-carboxylate, (3E,5S)-1-([1,1'-biphenyl]-4-ylcarbonyl)-5-[3-(2-hydroxyethyl)-1,2,4-oxadiazol-5-yl]-3-pyrrolidinone O-methyloxime, (3Z,5RS)-1-([1,1'-biphenyl]-4-ylcarbonyl)-5-[3-(2-hydroxyethyl)-1,2,4-oxadiazol-5-yl]-3-pyrrolidinone O-methyloxime, N-({3-[(2S,4EZ)-1-([1,1'-biphenyl]-4-ylcarbonyl)-4-(methoxyimino)pyrrolidinyl]-1,2,4-oxadiazol-5-yl}methyl)-3-(dimethylamino)propanamide, tert-butyl 4-(2-{3-[(2S,4EZ)-1-([1,1'-biphenyl]-4-ylcarbonyl)-4-(methoxyimino)pyrrolidinyl]-1,2,4-oxadiazol-5-yl}ethyl)-1-piperazinecarboxylate, (3EZ,5S)-1-[(2'-chloro-4'-fluoro[1,1'-biphenyl]-4-yl)carbonyl]-5-[3-(2-hydroxyethyl)-1,2,4-oxadiazol-5-yl]-3-pyrrolidinone O-methyloxime, (3EZ,5S)-1-[(4'-fluoro-2'-methyl[1,1'-biphenyl]-4-yl)carbonyl]-5-(3-methyl-1,2,4-oxadiazol-5-yl)-3-pyrrolidinone O-methyloxime, (3EZ,5S)-1-([1,1'-biphenyl]-4-ylcarbonyl)-5-{5-[2-(dimethylamino)ethyl]-1,2,4-oxadiazol-3-yl}-3-pyrrolidinone O-methyloxime, 2-{5-[(2S,4EZ)-1-([1,1'-biphenyl]-4-ylcarbonyl)-4-(methoxyimino)pyrrolidinyl]-1,2,4-oxadiazol-3-yl}ethyl[(tert-butoxycarbonyl)amino]acetate, N-({3-[(2S,4EZ)-1-([1,1'-biphenyl]-4-ylcarbonyl)-4-(methoxyimino)pyrrolidinyl]-1,2,4-oxadiazol-5-yl}methyl)-2-(dimethylamino)acetamide, (3EZ,5S)-1-[(2'-chloro-4'-fluoro[1,1'-biphenyl]-4-yl)carbonyl]-5-(3-methyl-1,2,4-oxadiazol-5-yl)-3-pyrrolidinone O-methyloxime, (3EZ,5S)-5-{5-[(1S)-1-amino-2-tert-butoxyethyl]-1,2,4-oxadiazol-3-yl}-1-([1,1'-biphenyl]-4-ylcarbonyl)-3-pyrrolidinone O-methyloxime, tert-butyl 4-{5-[(2S,4EZ)-1-([1,1'-biphenyl]-4-ylcarbonyl)-4-(methoxyimino)pyrrolidinyl]-1,2,4-oxadiazol-3-yl}-1-piperidinecarboxylate, (3EZ,5S)-1-([1,1'-biphenyl]-4-ylcarbonyl)-5-[5-(1-piperazinylmethyl)-1,2,4-oxadiazol-3-yl]-3-pyrrolidinone O-methyloxime, tert-butyl (4S)-4-{3-[(2S,4EZ)-1-([1,1'-biphenyl]-4-ylcarbonyl)-4-(methoxyimino)pyrrolidinyl]-1,2,4-oxadiazol-5-yl}-4-[(tert-butoxycarbonyl)amino]butanoate, 4-{[(2S,4EZ)-2-(5-{[(tert-butoxycarbonyl)amino]methyl}-1,2,4-oxadiazol-3-yl)-4-(methoxyimino)pyrrolidinyl]carbonyl}-1,1'-biphenyl, tert-butyl 2-{3-[(2S,4EZ)-1-([1,1'-biphenyl]-4-ylcarbonyl)-4-(methoxyimino)pyrrolidinyl]-1,2,4-oxadiazol-5-yl}ethylcarbamate, 2-{5-[(2S,4EZ)-1-([1,1'-biphenyl]-4-ylcarbonyl)-4-(methoxyimino)pyrrolidinyl]-1,2,4-oxadiazol-3-yl}ethyl aminoacetate, (3E,5S)-1-[(2',4'-difluoro[1,1'-biphenyl]-4-yl)carbonyl]-5-(3-methyl-1,2,4-oxadiazol-5-yl)-3-pyrrolidinone O-methyloxime, (3EZ,5S)-1-[(2',4'-difluoro[1,1'-biphenyl]-4-yl)carbonyl]-5-(3-methyl-1,2,4-oxadiazol-5-yl)-3-pyrrolidinone O-methyloxime, 4-{[(2S,4EZ)-2-(5-{(1S)-2-tert-butoxy-1-[(tert-butoxycarbonyl)amino]ethyl}-1,2,4-oxadiazol-3-yl)-4-(methoxyimino)pyrrolidinyl]carbonyl}-1,1'-biphenyl, (3EZ,5S)-1-([1,1'-biphenyl]-4-ylcarbonyl)-5-(5-vinyl-1,2,4-oxadiazol-3-yl)-3-pyrrolidinone O-methyloxime, 4-{[(2S,4EZ)-2-(5-{(1S,2R)-2-tert-butoxy-1-[(tert-butoxycarbonyl)amino]propyl}-1,2,4-oxadiazol-3-yl)-4-(methoxyimino)pyrrolidinyl]carbonyl}-1,1'-biphenyl, (3Z,5S)-1-[(2',4'-difluoro[1,1'-biphenyl]-4-yl)carbonyl]-5-(3-methyl-1,2,4-oxadiazol-5-yl)-3-pyrrolidinone O-methyloxime and tert-butyl 4-({3-[(2S,4EZ)-1-([1,1'-biphenyl]-4-ylcarbonyl)-4-(methoxyimino)pyrrolidinyl]-1,2,4-oxadiazol-5-yl}methyl)-1-piperazinecarboxylate.

16. A pharmaceutical composition comprising at least one compound according to claim 1 and a pharmaceutically acceptable carrier, diluent or excipient.

17. A method of preparing a compound of formula (I), as claimed in claim 1, wherein B is a 1,2,4-oxadiazole group of formula (IIb)

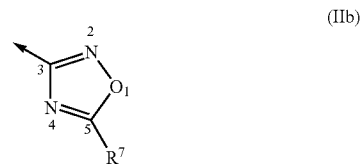

comprising:
reacting XV with VII

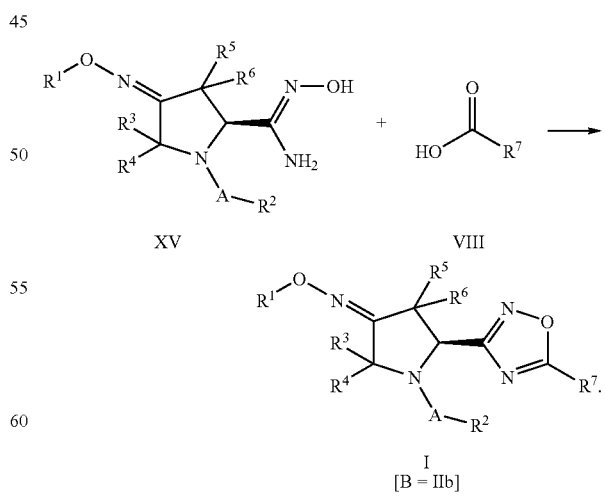

18. A method of preparing a compound of formula (I), as claimed in claim 1, wherein B is a 1,2,4-oxadiazole group of formula (IIa)

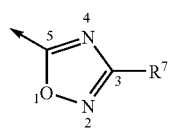
(IIa)
comprising:
reacting V with VI
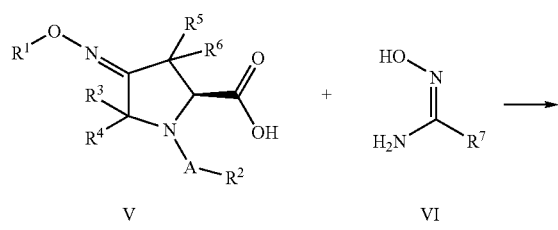
V          VI
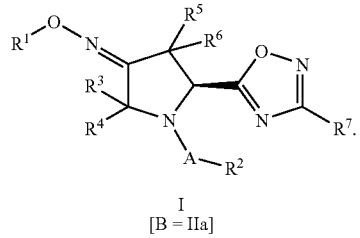
I
[B = IIa]
19. A method of preparing a compound of formula (I), as claimed in claim 1, wherein B is a 1,3,4-oxadiazole group of formula (III) or (IV) comprising either of:
reacting XVII with CDI or $CS_2$, or
reacting XVIII with Tmof and $P_2O_5$
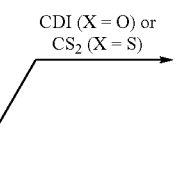
CDI (X = O) or
$CS_2$ (X = S)
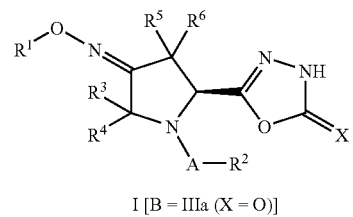
I [B = IIIa (X = O)]
I {B = IIIb (X = S)]
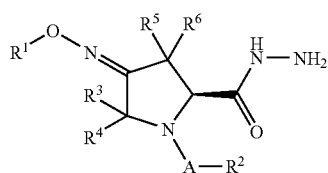
XVII
Tmof, $P_2O_5$
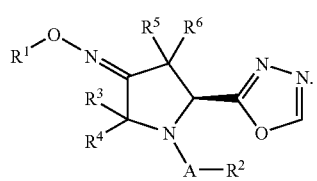
I {B = IV (X = bond, $R^8$ = H)]

20. The compound according to claim 1, wherein $R^1$ is —$CH_3$.

21. A method for treating preterm labor, premature birth or dysmenorrhea comprising
 administering an effective amount to a mammal in need thereof a pharmaceutical composition comprising the compound according to claim 1.

22. The method as claimed in claim 21, wherein the mammal is a human.

23. The method as claimed in claim 21, wherein the composition is administered in an amount effective for modulating an oxytocin receptor.

24. The method as claimed in claim 23, wherein modulating oxytocin receptor includes at least one of blocking the oxytocin receptor or antagonizing the binder of the oxytocin to a receptor.

25. The method as claimed in claim 21, wherein the composition is administered in an amount effective for the treatment or prevention of at least one disorder mediated by the oxytocin receptor.

26. The method as claimed in claim 21, wherein the administering is carried out orally.

* * * * *

UNITED STATES PATENT AND TRADEMARK OFFICE
CERTIFICATE OF CORRECTION

PATENT NO.       : 7,115,639 B2
APPLICATION NO.  : 10/480992
DATED            : October 3, 2006
INVENTOR(S)      : Matthias Schwarz et al.

It is certified that error appears in the above-identified patent and that said Letters Patent is hereby corrected as shown below:

On Title Page, Item (57) ABSTRACT, lines 15-16, "preparation. (I)B" should read --preparation. B--.

Column 3, line 61, "$C_2$-$C_6$-alkyl aryl" should read --$C_2$-$C_6$-alkynyl aryl--.

Column 6, line 12, "$CF_3$"" should read --$CF_3$--.

Column 10, line 34, "hetereocycloalkyl" should read --heterocycloalkyl--.

Column 11, line 21, "S" should read --S.--.

Column 14, line 22, "(3EZ,5S)-1-([1,1'-biphenyl]-4-ylcarbonyl)-5-{5-[(3)-1-me-" should read --(3EZ,5S)-1-([1,1'-biphenyl]-4-ylcarbonyl)-5-{5-[(3S)-1-me---;

Column 15, line 12, "5-yl)}-1-piperidinecarboxylate" should read --5-yl}-1-piperidinecarboxylate--.

Column 20, line 25, "  " should read --  --.

Column 20, line 45, "nitrites" should read --nitriles--.

Column 22, line 18, "practicioner" should read --practitioner--;

line 31, "I[B=IIa (X=0)]" should read --I[B=IIIa (X=0)]--.

Column 24, line 17, "performd" should read --performed--.

Column 25, line 37, "B' is moiety" should read --B' is B moiety--;

line 51, "Alkviation" should read --Alkylation--.

UNITED STATES PATENT AND TRADEMARK OFFICE
CERTIFICATE OF CORRECTION

PATENT NO.        : 7,115,639 B2
APPLICATION NO. : 10/480992
DATED             : October 3, 2006
INVENTOR(S)       : Matthias Schwarz et al.

It is certified that error appears in the above-identified patent and that said Letters Patent is hereby corrected as shown below:

Column 29, lines 11-21, " 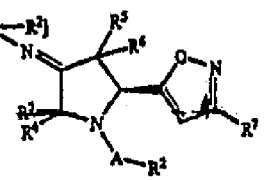

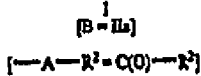

"

should read

-- 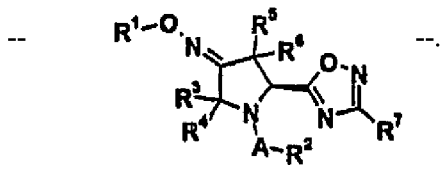

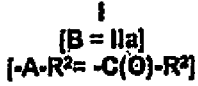 --.

Column 30, line 55, "provides; compounds" should read --provides compounds--.

Column 31, lines 44-45, "desintegrating" should read --disintegrating--;

line 62, "be" should read --by--.

Column 32, line 14, "nopyridine) DMF" should read --nopyridine), DMF--;

line 47, "(500 ml)" should read --(1500 ml)--.

Column 33, line 39, "magnesiom" should read --magnesium--;

line 62, "2S)-(tert-butoxycarbo-" should read --2S)-1-(tert-butoxycarbo---.

Column 34, line 4, "magnesiom" should read --magnesium--;

line 66, "(intermedi-" should read --(Intermedi---.

Column 36, line 22, "aminohy-" should read --amino(hy---.

Column 38, line 28, "sirred" should read --stirred--.

UNITED STATES PATENT AND TRADEMARK OFFICE
CERTIFICATE OF CORRECTION

PATENT NO. : 7,115,639 B2
APPLICATION NO. : 10/480992
DATED : October 3, 2006
INVENTOR(S) : Matthias Schwarz et al.

It is certified that error appears in the above-identified patent and that said Letters Patent is hereby corrected as shown below:

Column 41, line 29, "materiel" should read --material--;

line 36, "characterization" should read --characterization.--;

line 52, "19% yield)" should read --19% yield).--.

Column 46, line 2, "(m, 2H, $CH_2$);" should read --(m, 2H, $CH_2$),--;

line 9, "MS(ES" should read --MS($ESI^+$)--;

line 20, "O-methyloxime" should read --O-methyloxime.--.

Column 47, line 19, "MS($ESI^{-)}$:" should read --MS($ESI^-$):--.

Column 48, line 46 "deparated" should read --separated--;

line 55, "O-me" should read --O-me---.

Column 50, line 26, "dihydroxypropanidamide" should read

--dihydroxypropanimidamide--.

Column 51, line 29, "inter-" should read --Inter---.

Column 52, line 43, "(m, 9H), H arom.)" should read --(m, 9H,H arom.)--.

Column 53, line 65, "evaporatedm" should read --evaporated--.

Column 56, line 64, "hydroxy(methoxyimino)" should read

--hydroxy-4-(methoxyimino)--.

Column 63, line 29, "tide" should read --title--.

Column 65, line 1, "micture" should read --mixture--.

Column 67, line 36, "s, 3H, $CH_3$);" should read --(s, 3H, $CH_3$),--;

line 67, "-4-ylcarbonyl)-1-" should read ---4-ylcarbonyl)-N'---.

UNITED STATES PATENT AND TRADEMARK OFFICE
CERTIFICATE OF CORRECTION

PATENT NO. : 7,115,639 B2  Page 4 of 7
APPLICATION NO. : 10/480992
DATED : October 3, 2006
INVENTOR(S) : Matthias Schwarz et al.

It is certified that error appears in the above-identified patent and that said Letters Patent is hereby corrected as shown below:

Column 68, line 25,

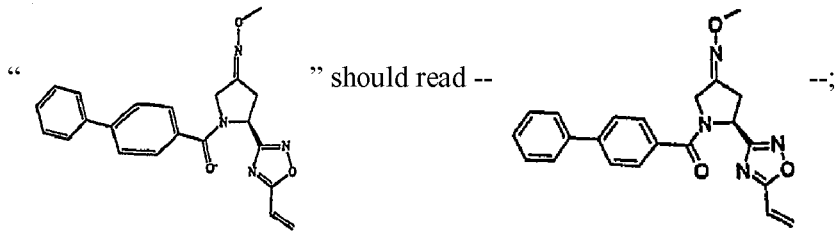

line 38, "6.53" shoud read --6.58--.

Column 69, line 47, "(3EZ,5S)-l-([l'-biphenyl]-4-ylcarbonyl)-5-{5-[(3)-" should read --(3EZ,5S)-1-([1,1'-biphenyl]-4-ylcarbonyl)-5-{5-[(3R)---.

Column 76, line 29, "3H CH$_3$)," should read --m, 3H, CH$_3$)--.

line 35, "Example 50" should read --Example 51--.

Column 77, line 11, "Example 51" should read --Example 52--.

Column 78, line 6, "Example 52" should read --Example 53--.

Column 79, line 2, "Example 53" should read --Example 54--.

Column 80, line 2, "Example 54" should read --Example 55--.

line 36, "Example 55" should read --Example 56--.

Column 82, line 13, "Example 56" should read --Example 57--;

line 19, "(3EZ,5S)-5-{5-{1S,2R)-l-amino-2-" should read

--(3EZ,5S)-5-{5-[(1S,2R)-1-amino-2---.

Column 83, line 27, "Example 57" should read --Example 58--.

Column 84, line 2, "Example 58" should read --Example 59--;

line 50, "Example 59" should read --Example 60--.

UNITED STATES PATENT AND TRADEMARK OFFICE
CERTIFICATE OF CORRECTION

PATENT NO. : 7,115,639 B2
APPLICATION NO. : 10/480992
DATED : October 3, 2006
INVENTOR(S) : Matthias Schwarz et al.

It is certified that error appears in the above-identified patent and that said Letters Patent is hereby corrected as shown below:

Column 85, line 46, "Example 60" should read --Example 61--;

Column 86, line 7, "Example 61" should read --Example 62--;

line 38, "Example 62" should read --Example 63--.

Column 87, line 2, "Example 63" should read --Example 64--;

line 33, "Example 64" should read --Example 65--.

Column 88, line 2, "Example 65" should read --Example 66--;

line 32, "Example 66" should read --Example 67--.

Column 89, line 2, "Example 67" should read --Example 68--;

line 29, "N-hydroxy-2-(me-" should read --N'-hydroxy-2-(me---.

line 35, "Example 68" should read --Example 69--.

Column 90, line 2, "Example 69" should read --Example 70--;

line 35, "Example 70" should read --Example 71--;

line 67, "TPLC" should read --HPLC--.

Column 91, line 2, "Example 71" should read --Example 72--;

line 35, "Example 72" should read --Example 73--.

Column 92, line 2, "Example 73" should read --Example 74--;

line 35, "Example 74" should read --Example 75--.

Column 93, line 2, "Example 75" should read --Example 76--;

line 35, "Example 76" should read --Example 77--.

UNITED STATES PATENT AND TRADEMARK OFFICE
CERTIFICATE OF CORRECTION

PATENT NO. : 7,115,639 B2
APPLICATION NO. : 10/480992
DATED : October 3, 2006
INVENTOR(S) : Matthias Schwarz et al.

It is certified that error appears in the above-identified patent and that said Letters Patent is hereby corrected as shown below:

Column 94, line 2, "Example 77" should read --Example 78--;

line 35, "Example 78" should read --Example 79--;

line 63, "(Inter-mediate 2)," should read --Intermediate--;

line 65, "[aminohydroxyimino" should read --amino(hydroxyimino)--.

Column 95, line 2, "Example 79" should read --Example 80--;

line 46, "(2S,4EZ)-l-methoxyimino)-2-(5-thioxo-4,5-di-" should read

--(2S,4EZ)-4-(methoxyimino)---.

Column 96, line 6, "Example 80" should read --Example 81--;

line 37, "27" should read --279--.

Column 97, line 2, "Example 81" should read --Example 82--.

Column 98, line 2, "Example 82" should read --Example 83--;

line 45, "Example 83" should read --Example 84--.

Column 99, line 18, "Example 84" should read --Example 85--.

Column 101, line 14,

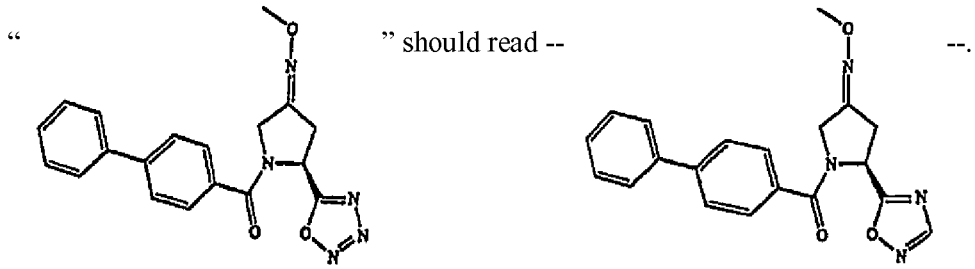

UNITED STATES PATENT AND TRADEMARK OFFICE
CERTIFICATE OF CORRECTION

PATENT NO. : 7,115,639 B2
APPLICATION NO. : 10/480992
DATED : October 3, 2006
INVENTOR(S) : Matthias Schwarz et al.

It is certified that error appears in the above-identified patent and that said Letters Patent is hereby corrected as shown below:

Column 105, line 65,

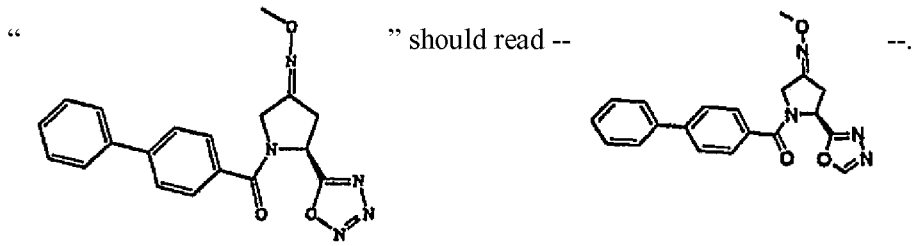

Column 109, line 48,

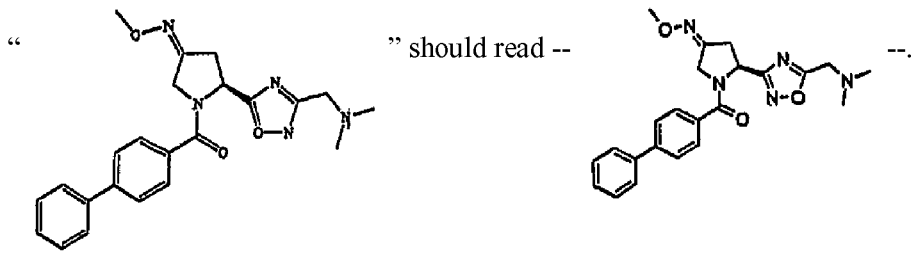

Column 110, line 21, "Intravenous" should read --intravenous--;

line 23, "Intravenous" should read --intravenous--.

Column 113, line 27, "of heteroarylcarbonyl" should read --heteroaryl carbonyl--.

Column 122, lines 6-7, "composition is administered in an amount effective for the treatment or prevention of at least one disorder" should read --treating preterm labor, the premature birth or the dysmenorrhea is--.

Signed and Sealed this

Fourth Day of March, 2008

JON W. DUDAS
*Director of the United States Patent and Trademark Office*